US007985764B2

(12) United States Patent
Kaku et al.

(10) Patent No.: US 7,985,764 B2
(45) Date of Patent: Jul. 26, 2011

(54) AMIDE DERIVATIVE OR SALT THEREOF

(75) Inventors: Hidetaka Kaku, Tokyo (JP); Hiroyoshi Yamada, Tokyo (JP); Daisuke Kaga, Tokyo (JP); Ryushi Seo, Tokyo (JP); Shinobu Akuzawa, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 357 days.

(21) Appl. No.: 12/279,221

(22) PCT Filed: Feb. 7, 2007

(86) PCT No.: PCT/JP2007/052109
§ 371 (c)(1),
(2), (4) Date: Aug. 13, 2008

(87) PCT Pub. No.: WO2007/097197
PCT Pub. Date: Aug. 30, 2007

(65) Prior Publication Data
US 2009/0062363 A1  Mar. 5, 2009

(30) Foreign Application Priority Data
Feb. 20, 2006  (JP) .................. P2006-041827

(51) Int. Cl.
*C07D 209/08* (2006.01)
*A61K 31/404* (2006.01)

(52) U.S. Cl. ......... 514/419; 548/469; 548/490; 548/491

(58) Field of Classification Search .................. 548/469, 548/490, 491; 514/419
See application file for complete search history.

(56) References Cited

U.S. PATENT DOCUMENTS

| | | | |
|---|---|---|---|
| 5,852,046 A | 12/1998 | Lang et al. | |
| 6,358,992 B1 | 3/2002 | Pamukcu et al. | |
| 6,440,988 B1 | 8/2002 | Craig | |
| 6,514,968 B1 | 2/2003 | TenBrink | |
| 6,534,535 B1 | 3/2003 | Zhu et al. | |
| 2008/0171788 A1 | 7/2008 | Akuzawa et al. | |
| 2010/0168096 A1 | 7/2010 | Yamada et al. | |

FOREIGN PATENT DOCUMENTS

| | | |
|---|---|---|
| AU | 68844/94 | 2/1995 |
| EP | 0 622 356 | 11/1994 |
| EP | 0 639 573 | 2/1995 |
| EP | 1 716 867 | 11/2006 |
| EP | 1 728 784 | 12/2006 |
| EP | 1 852 129 | 11/2007 |
| EP | 1 923 387 | 5/2008 |
| JP | 07-010839 | 1/1995 |
| JP | 07-145149 | 6/1995 |
| JP | 8-48671 | 2/1996 |
| JP | 10-67682 | 3/1998 |
| JP | 10-114654 | 5/1998 |
| JP | 2005-162657 | 6/2005 |
| JP | 2005162657 A * | 6/2005 |
| WO | 96/32379 | 10/1996 |
| WO | 99/20599 | 4/1999 |
| WO | 01/12600 | 2/2001 |
| WO | 2004/108688 | 12/2004 |

OTHER PUBLICATIONS

Kitano et al. Chemical and Pharmaceutical Bulletin (1999), 47(11), 1538-1548.*
Whorwell et al., "Bladder smooth muscle dysfunction in patients with irritable bowel syndrome", Gut, vol. 27 (1986) 1014-17.
Hoyer, et al., VII. International Union of Pharmacology Classification of Receptors for 5-Hydroxytryptamine (Serotonin); Pharmacological Reviews, vol. 46, No. 2 (1994) 157-203.
Bearcroft, et al., "Postprandial plasma 5-hydroxytryptamine in diarrhoea predominant irritable bowel syndrome: a pilot study", Gut, vol. 42 (1998) 42-6.
Kim, et al., "Serotonin: A Mediator of the Brain—Gut Connection", The American Journal of Gastroenterology, vol. 95, No. 10 (2000) 2698-709.
Talley, "Pharmacological Therapy for the Irritable Bowel Syndrome", The American Journal of Gastroenterology, vol. 98, No. 4 (2003) 750-58.
Wyatt, et al., "Indentification of Potent and Selective Oxytocin Antagonists. Part 1: Indole and Benzofuran Derivatives", Bioorganic & Medicinal Chemistry Letters, vol. 12, No. 10 (2002) 1399-1404.
DePonti, et al., "Irritable Bowel Syndrome, New Agents Targeting Serotonin Receptor Subtypes", Drugs, vol. 61, No. 3 (2001) 317-32.
Carter, et al., "Characterization of a postjunctional 5-HT receptor mediating relaxation of guinea-pig isolated ileum", European Journal of Pharmacology, vol. 280 (1995) 243-50.
Liu, et al., "Expression patterns of 5-HT7 receptor isoforms in the rat digestive tract", Life Sciences, vol. 69 (2001) 2467-75.
Borman, et al., "Functional evidence for a 5-HT2B receptor mediating contraction of longitudinal muscle in human small intestine", British Journal of Pharmacology, vol. 114 (1995) 1525-27.
Vourloumis, et al., "Solid-phase synthesis of benzimidazole libraries biased for RNA targets", Tetrahedron Letters, vol. 44, No. 14 (2003) 2807-11.

(Continued)

*Primary Examiner* — Kahsay T Habte
(74) *Attorney, Agent, or Firm* — Fitzpatrick, Cella, Harper & Scinto

(57) ABSTRACT

It was found that a compound according to the following formula:

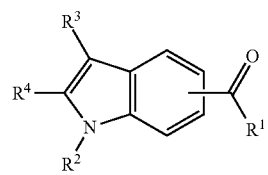

or a pharmaceutically acceptable salt thereof, has a strong antagonism for both the $5\text{-}HT_{2B}$ and $5\text{-}HT_7$ receptors. In addition, the compound shows good pharmacological action as compared to antagonists selective for only one of these receptors. Based on the above, the compound of the present invention is useful for the prevention and/or treatment of diseases in which $5\text{-}HT_{2B}$ receptor and $5\text{-}HT_7$ receptor are concerned, particularly for the treatment of irritable bowel syndrome (IBS).

8 Claims, 3 Drawing Sheets

OTHER PUBLICATIONS

Lopez-Rodriguez, et al., "Benzimidazole Derivatives. 3. 3D-QSAR/CoMFA Model and Computational Simulation for the Recognition of 5-HT4 Receptor Antagonists", J. Med. Chem., vol. 45, No. 22 (2002) 4806-15.

Kuroita, et al., "Design and Synthesis of 6-Chloro-3,4-dihydro-4-methyl-2H-1,4-benzoxazine-8-carboxamide Derivatives as Potent Serotonin-3 (5-HT3) Receptor Antagonist", Chem. Pharm. Bull., vol. 44, No. 4 (1996) 756-64.

Borman, et al., "5-HT2B receptors play a key role in mediating the excitatory effects of 5-HT in human colon in vitro", British Journal of Pharmacology, vol. 135 (2002) 1144-51.

CAS Registry No. 312604-61-8; Jul. 24, 2007.
CAS Registry No. 515828-64-5; Feb. 7, 2006.
CAS Registry No. 338984-26-2; Sep. 6, 2007.
CAS Registry No. 309727-87-5; Apr. 9, 2007.
CAS Registry No. 846563-08-4; Apr. 9, 2007.
CAS Registry No. 846563-01-7; Apr. 9, 2007.
CAS Registry No. 878688-87-0; Apr. 9, 2007.
CAS Registry No. 846563-24-4; Sep. 6, 2007.
CAS Registry No. 895121-54-7; Sep. 6, 2007.
CAS Registry No. 895117-17-6; Sep. 6, 2007.
CAS Registry No. 895097-35-5; Sep. 6, 2007.
CAS Registry No. 895122-22-2; Sep. 6, 2007.
CAS Registry No. 895122-18-6; Sep. 6, 2007.
CAS Registry No. 895122-14-2; Sep. 6, 2007.
CAS Registry No. 895122-06-2; Sep. 6, 2007.
CAS Registry No. 895119-58-1; Sep. 6, 2007.
CAS Registry No. 895119-53-6; Sep. 6, 2007.
CAS Registry No. 895119-48-9; Sep. 6, 2007.
CAS Registry No. 895119-38-7; Sep. 6, 2007.
CAS Registry No. 895119-23-0; Sep. 6, 2007.
CAS Registry No. 895119-18-3; Sep. 6, 2007.
CAS Registry No. 895119-08-1; Sep. 6, 2007.
CAS Registry No. 895100-05-7; Sep. 6, 2007.
CAS Registry No. 895099-04-4; Sep. 6, 2007.
CAS Registry No. 895098-99-4; Sep. 6, 2007.
CAS Registry No. 895098-94-9; Sep. 6, 2007.
CAS Registry No. 895098-89-2; Sep. 6, 2007.
CAS Registry No. 895121-82-1; Sep. 6, 2007.
CAS Registry No. 895121-66-1; Sep. 6, 2007.
CAS Registry No. 895121-14-9; Sep. 6, 2007.
CAS Registry No. 895119-83-2; Sep. 6, 2007.
CAS Registry No. 895118-43-1; Sep. 6, 2007.
CAS Registry No. 895118-03-3; Sep. 6, 2007.
CAS Registry No. 895117-98-3; Sep. 6, 2007.
CAS Registry No. 895117-93-8; Sep. 6, 2007.
CAS Registry No. 895117-88-1; Sep. 6, 2007.
CAS Registry No. 895117-83-6; Sep. 6, 2007.
CAS Registry No. 895117-59-6; Sep. 6, 2007.
CAS Registry No. 895116-57-1; Sep. 6, 2007.
CAS Registry No. 895099-84-0; Sep. 6, 2007.
CAS Registry No. 895099-24-8; Sep. 6, 2007.
CAS Registry No. 895098-39-2; Sep. 6, 2007.
CAS Registry No. 895098-30-3; Sep. 6, 2007.
CAS Registry No. 895098-26-7; Sep. 6, 2007.
CAS Registry No. 895098-13-2; Sep. 6, 2007.
CAS Registry No. 895098-08-5; Sep. 6, 2007.
CAS Registry No. 895098-04-1; Sep. 6, 2007.
CAS Registry No. 895098-00-7; Sep. 6, 2007.
CAS Registry No. 895097-96-8; Sep. 6, 2007.
CAS Registry No. 895097-88-8; Sep. 6, 2007.
CAS Registry No. 895097-84-4; Sep. 6, 2007.
CAS Registry No. 895097-63-9; Sep. 6, 2007.
CAS Registry No. 895096-80-7; Sep. 6, 2007.
CAS Registry No. 895120-70-4; Sep. 6, 2007.
CAS Registry No. 895098-21-2; Sep. 6, 2007.
CAS Registry No. 895098-17-6; Sep. 6, 2007.
CAS Registry No. 895097-92-4; Sep. 6, 2007.
CAS Registry No. 895096-32-9; Sep. 6, 2007.

Tuladhar, et al., "5-HT7 receptors mediate the inhibitory effect of 5-HT on peristalsis in the isolated guinea-pig ileum", British Journal of Pharmacology, vol. 138 (2003) 1210-14.

CAS Registry No. 895118-33-9; Sep. 6, 2007.
CAS Registry No. 895118-28-2; Sep. 6, 2007.
CAS Registry No. 895118-18-0; Sep. 6, 2007.
CAS Registry No. 895118-13-5; Sep. 6, 2007.
CAS Registry No. 895118-08-8; Sep. 6, 2007.

Patani, et al., "Bioisosterism: A Rational Approach in Drug Design", Chem. Rev., vol. 96 (1996) 3147-76.

Theoharides, et al., "Interstitial cystitis: bladder pain and beyond", Expert Opin. Pharmacother., vol. 9, No. 17 (2008) 2979-94.

* cited by examiner

AMIDE DERIVATIVE OR SALT THEREOF

TECHNICAL FIELD

The present invention relates to a pharmaceutical, particularly an amide derivative which is useful as an agent for treating irritable bowel syndrome.

BACKGROUND OF THE INVENTION

Serotonin (5-HT) is a monoamine neurotransmitter and exerts various physiological actions via the 5-HT receptor. The 5-HT receptor is classified into seven families of from $5\text{-}HT_1$ to $5\text{-}HT_7$. Particularly, the $5\text{-}HT_2$ receptor is known to have three subtypes, $5\text{-}HT_{2A}$, $5\text{-}HT_{2B}$ and $5\text{-}HT_{2C}$ (Non-patent Reference 1).

The irritable bowel syndrome (IBS) is a disease in which an abdominal pain or an abdominal unpleasantness continues for a prolonged period of time. Based on its symptoms, IBS is classified into a diarrhea type, a constipation type and a mixed type of diarrhea and constipation. In each case, it has been pointed out that there is a causal relation between the morbid state and the amount of 5-HT in blood. For example, there is a reference which points out that increase of blood 5-HT concentration after meal occurs in diarrhea type IBS patients and this is deeply concerned in the morbid state (Non-patent Reference 2).

Currently, though it is at the clinical trial in Japan, a 5-HT receptor antagonist or a 5-HT receptor agonist is used in Europe and America as an agent for treating IBS. As an agent for treating diarrhea type, alosetron ($5\text{-}HT_3$ receptor antagonist) is used in the clinical field, but side effects such as ischemic colitis, constipation and the like have been reported. In addition, as an agent for treating constipation type, tegaserod ($5\text{-}HT_4$ receptor agonist) is used in the clinical field in Europe and America, but side effects have also been reported (Non-patent References 3 and 4).

In recent years, pharmacological studies on other 5-HT receptor subtypes have also been carried out (Non-patent Reference 5). Regarding the $5\text{-}HT_{2B}$ receptor and $5\text{-}HT_7$ receptor, there are reports which pointed out roles of said receptors in digestive tracts. For example, there are reports stating that the $5\text{-}HT_{2B}$ receptor localizes in human ileum longitudinal muscle and a $5\text{-}HT_{2B}$ receptor antagonistic compound suppresses contraction by 5-HT (Non-patent Reference 6), and that the $5\text{-}HT_{2B}$ receptor localizing in human colon is concerned in the 5-HT-induced contraction at the time of electric stimulation and a $5\text{-}HT_{2B}$ receptor antagonistic compound suppresses it (Non-patent Reference 7).

In addition, there are reports stating that the $5\text{-}HT_7$ receptor localizes in guinea pig small intestines (Non-patent Reference 8) and rat small intestines (Non-patent Reference 9) and is concerned in the peristalsis of guinea pig ileum (Non-patent Reference 10). Also, in the Patent Reference 1 which was applied by the present applicant and laid open to public after priority date of the instant application, it is reported that a selective $5\text{-}HT_{2B}$ and $5\text{-}HT_7$ receptor dual antagonist is useful in treating IBS. Based on the above, it is expected that a compound having the antagonistic activity for $5\text{-}HT_{2B}$ and $5\text{-}HT_7$ receptors is useful as an IBS treating agent.

In addition, since there are reports stating that a selective $5\text{-}HT_{2B}$ and $5\text{-}HT_7$ receptor dual antagonist is useful in preventing migraine (Patent References 2 and 3), it is expected that a compound having the antagonistic activity for $5\text{-}HT_{2B}$ and $5\text{-}HT_7$ receptors is also useful as an agent for preventing migraine.

As the compound having the antagonistic activity for $5\text{-}HT_{2B}$ and $5\text{-}HT_7$ receptors, there are reports of the following Patent References 1 to 4.

It has been reported that a fluorene derivative represented by the following formula (A) has the antagonistic activity for $5\text{-}HT_{2B}$ and $5\text{-}HT_7$ receptors and is useful in preventing migraine (Patent References 2 and 3) and in treating IBS (Patent Reference 1).

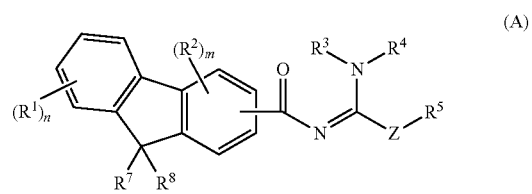

(A)

(See said official gazettes for symbols in the formula.)

In addition, as the amide derivatives having a nitrogen-containing bicyclic hetero ring (e.g., indole or the like), the following reports exist.

In the Patent Reference 4, it is reported that an indolylguanidine derivative represented by the following formula (B) has the sodium/proton antiporter system inhibitory action and is effective in treating and preventing high blood pressure, heart muscle ischemia, reperfusion injury and the like. However, there are no descriptions on its $5\text{-}HT_{2B}$ and $5\text{-}HT_7$ receptor antagonistic activities and its efficacy for IBS.

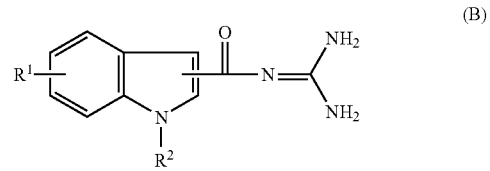

(B)

(See said official gazette for symbols in the formula.)

In the Patent Reference 5, it is reported that a benzo-condensed heterocyclic compound represented by the following formula (C) has the sodium/proton exchange inhibitory action and is useful as an agent for treating heart diseases such as arrhythmia and the like. However, there are no descriptions on its $5\text{-}HT_{2B}$ and $5\text{-}HT_7$ receptor antagonistic activities and its efficacy for IBS.

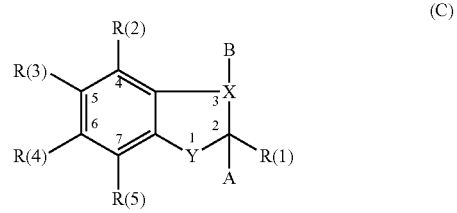

(C)

(See said official gazette for symbols in the formula.)

In the Patent Reference 6, it is reported that an indole derivative represented by the following formula (D) has the cannabinoid receptor-regulating action and is useful as an agent for preventing or treating or an agent for diagnosing cerebrovascular disorders, etc. However, there are no descriptions on its $5\text{-}HT_{2B}$ and $5\text{-}HT_7$ receptor antagonistic activities and its efficacy for IBS.

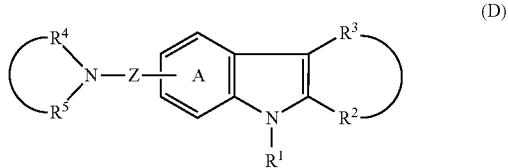

(See said official gazette for symbols in the formula.)

In the Patent Reference 7, it is reported that a benzimidazole derivative represented by the following formula (E) is useful for renal diseases. However, there are no descriptions on its 5-$HT_{2B}$ and 5-$HT_7$ receptor antagonistic activities and its efficacy for IBS.

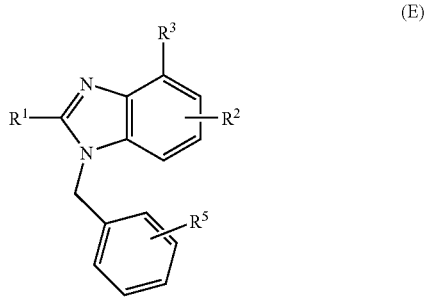

(See said official gazette for symbols in the formula.)

In Non-patent Reference 11, a solid phase synthesis method of a benzimidazole derivative represented by the following formula (F) is reported. However, there are no descriptions on its 5-$HT_{2B}$ and 5-$HT_7$ receptor antagonistic activities and its efficacy for IBS.

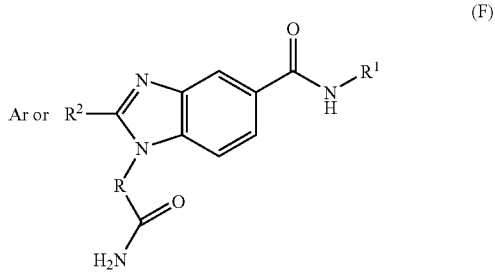

(See said official gazette for symbols in the formula.)

Also, 1-benzyl-N-[2-(dimethylamino)ethyl]-2,3-dimethyl-1H-indole-5-carboxamide (CAS Registry No. 312604-61-8), 1-benzyl-5-[(4-ethylpiperazin-1-yl)carbonyl]-2,3-dimethyl-1H-indole (CAS Registry No. 515828-64-5), 1-benzyl-5-[(4-benzylpiperazin-1-yl)carbonyl]-2,3-dimethyl-1H-indole (CAS Registry No. 338984-26-2), and 5-[(4-benzoylpiperazin-1-yl)carbonyl]-1-benzyl-2,3-dimethyl-1H-indole (CAS Registry No. 309727-87-5), N-(1-benzylpiperidin-4-yl)-1-(4-methoxybenzyl)-2-oxo-2,3-dihydro-1H-benzimidazole-5-carboxamide (CAS Registry No. 846563-08-4) and N-(1-benzylpiperidin-4-yl)-1-(4-fluorobenzyl)-2-oxo-2,3-dihydro-1H-benzimidazole-5-carboxamide (CAS Registry No. 846563-01-7) have been reported as catalog compounds. However, there are no reports on the 5-$HT_{2B}$ and 5-$HT_7$ receptor antagonistic activities of these compounds and their efficacy for IBS.

In addition, in a catalog "Aurora Screening Library" (STN data base, date of publication by CHEMCAT, May 10, 2006), published by Aurora fine Chemicals after the priority date of this application, N-(1-benzylpiperidin-4-yl)-1-(4-fluorobenzyl)-2,3-dimethyl-1H-indole-5-carboxamide (CAS Registry No. 895121-54-7), 1-benzyl-N-(1-benzylpiperidin-4-yl)-2,3-dimethyl-1H-indole-5-carboxamide (CAS Registry No. 895117-17-6), N-(1-benzylpiperidin-4-yl)-1-(4-chlorobenzyl)-2,3-dimethyl-1H-indole-5-carboxamide (CAS Registry No. 895097-35-5), 1-(4-fluorobenzyl)-5-{[4-(4-fluorophenyl)piperazin-1-yl]carbonyl}-2,3-dimethyl-1H-indole (CAS Registry No. 895122-22-2), 1-(4-fluorobenzyl)-2,3-dimethyl-5-[(4-pyridin-2-ylpiperazin-1-yl)carbonyl]-1H-indole (CAS Registry No. 895122-18-6), 1-(4-fluorobenzyl)-2,3-dimethyl-5-{[4-(4-nitrophenyl)piperazin-1-yl]carbonyl}-1H-indole (CAS Registry No. 895122-14-2), 5-{[4-(4-chlorophenyl)piperazin-1-yl]carbonyl}-1-(4-fluorobenzyl)-2,3-dimethyl-1H-indole (CAS Registry No. 895122-06-2), 1-benzyl-5-{[4-(2-fluorophenyl)piperazin-1-yl]carbonyl}-2,3-dimethyl-1H-indole (CAS Registry No. 895119-58-1), 1-benzyl-2,3-dimethyl-5-[(4-pyrimidin-2-ylpiperazin-1-yl)carbonyl]-1H-indole (CAS Registry No. 895119-53-6), 1-benzyl-5-{[4-(4-fluorophenyl)piperazin-1-yl]carbonyl}-2,3-dimethyl-1H-indole (CAS Registry No. 895119-48-9), 1-benzyl-2,3-dimethyl-5-[(4-pyridin-2-ylpiperazin-1-yl)carbonyl]-1H-indole (CAS Registry No. 895119-38-7), 1-benzyl-5-{[4-(2,5-dimethylphenyl)piperazin-1-yl]carbonyl}-2,3-dimethyl-1H-indole (CAS Registry No. 895119-23-0), 1-benzyl-5-{[4-(2,3-dimethylphenyl)piperazin-1-yl]carbonyl}2,3-dimethyl-1H-indole (CAS Registry No. CAS 895119-18-3), 1-benzyl-2,3-dimethyl-5-[(4-phenylpiperazin-1-yl)carbonyl]-1H-indole (CAS Registry No. 895119-08-1), 2,3-dimethyl-1-(3-methylbenzyl)-5-[(4-pyridin-2-ylpiperazin-1-yl)carbonyl]-1H-indole (CAS Registry No. 895100-05-7), 1-(4-chlorobenzyl)-5-{[4-(2-fluorophenyl)piperazin-1-yl]carbonyl}-2,3-dimethyl-1H-indole (CAS Registry No. 895099-04-4), 1-(chlorobenzyl)-2,3-dimethyl-5-[(4-pyrimidin-2-ylpiperazin-1-yl)carbonyl]-1H-indole (CAS Registry No. 895098-99-4), 1-(chlorobenzyl)-5-{[4-(2,5-dimethylphenyl)piperazin-1-yl]carbonyl}-2,3-dimethyl-1H-indole (CAS Registry No. 895098-94-9), 1-(chlorobenzyl)-5-{[4-(2,3-dimethylphenyl)piperazin-1-yl]carbonyl}-2,3-dimethyl-1H-indole (CAS Registry No. 895098-89-2), 1-(4-fluorobenzyl)-2,3-dimethyl-N-(3-pyrrolidin-1-ylpropyl)-1H-indole-5-carboxamide (CAS Registry No. 895121-82-1), 1-(4-fluorobenzyl)-2,3-dimethyl-N-(2-morpholin-4-ylethyl)-1H-indole-5-carboxamide (CAS Registry No. 895121-66-1), 1-(4-fluorobenzyl)-2,3-dimethyl-N-(3-morpholin-4-ylpropyl)-1H-indole-5-carboxamide (CAS Registry No. 895121-14-9), 1-benzyl-N-[4-(dimethylamino)benzyl]-2,3-dimethyl-1H-indole-5-carboxamide (CAS Registry No. 895121-14-9), 1-benzyl-2,3-dimethyl-N-[2-(4-methylpiperazin-1-yl)ethyl]-1H-indole-5-carboxamide (CAS Registry No. 895118-43-1), 1-benzyl-N-[3-(4-benzylpiperazin-1-yl)propyl]-2,3-dimethyl-1H-indole-5-carboxamide (CAS Registry No. 895118-33-9), 1-benzyl-N-[3-(4-benzylpiperazin-1-yl)propyl]-2,3-dimethyl-1H-indole-5-carboxamide (CAS Registry No. 895118-28-2), 1-benzyl-N-{3-[4-(2-fluorophenyl)piperazin-1-yl]propyl}-2,3-dimethyl-1H-indole-5-carboxamide (CAS Registry No. 895118-18-0), 1-benzyl-2,3-dimethyl-N-[2-(2-methylpiperidin-1-yl)ethyl]-1H-indole-5-carboxamide (CAS Registry No. 895118-13-5), 1-benzyl-2,3-dimethyl-N-(3-pyrrolidin-1-ylpropyl)-1H-indole-5-carboxamide (CAS Registry No. 895118-08-8), 1-benzyl-2,3-dimethyl-N-[3-(2-methylpiperidin-1-yl)propyl]-1H-indole-5-carboxamide (CAS Registry No. 895118-03-3), N-(3-azepin-1-ylpropyl)-1-benzyl-2,3-dimethyl-1H- indole-5-carboxamide (CAS Registry No. 895117-98-3), 1-benzyl-N-[3-(2-ethylpiperidin-1-yl)propyl]-2,3-dimethyl-1H-indole-5-carboxamide (CAS Registry No. 895117-98-3), 1-benzyl-2,3-dimethyl-N-(3-piperidin-1-ylpropyl)-1H-indole-5-carboxamide (CAS Registry No. 895117-88-1), 1-benzyl-2,3-dimethyl-N-[3-(4-methylpiperazin-1-yl)propyl]-1H-indole-5-carboxamide (CAS Registry No. 895117-83-6), 1-benzyl-2,3-dimethyl-N-(2-morpholin-4-ylethyl)-1H-indole-5-carboxamide (CAS Registry No. 895117-59-6), 1-benzyl-2,3-dimethyl-N-(3-morpholin-4-ylpropyl)-1H-indole-5-carboxamide (CAS Registry No. 895116-57-1), 2,3-dimethyl-1-(3-methylbenzyl)-N-(2-morpholin-4-ylethyl)-1H-indole-5-carboxamide (CAS Registry No. 895099-84-0), 1-(4-chlorobenzyl)-N-[4-(dimethylamino)benzyl]-2,3-dimethyl-1H-indole-5-carboxamide (CAS Registry No. 895099-24-8), 1-(4-chlorobenzyl)-2,3-dimethyl-N-[3-(4-propylpiperazin-1-yl)propyl]-1H-indole-5-carboxamide (CAS Registry No. 895098-39-2), 1-(4-chlorobenzyl)-2,3-dimethyl-N-[2-(2-methylpiperidin-1-yl)ethyl]-1H-indolyl-5-carboxamide (CAS Registry No. 895098-30-3), 1-(4-chlorobenzyl)-N-3-(4-ethylpiperazin-1-yl)propyl]-2,3-dimethyl-1H-indole-5-carboxamide (CAS Registry No. 895098-26-7), 1-(4-chlorobenzyl)-2,3-dimethyl-N-(2-pyrrolidin-1-ylethyl)-H-indole-5-carboxamide (CAS Registry No. 895098-13-2), N-(2-azepan-1-ylethyl)-1-(4-chlorobenzyl)-2,3-dimethyl-1H-indole-5-carboxamide (CAS Registry No. 895098-08-5), 1-(4-chlorobenzyl)-2,3-dimethyl-N-(3-pyrrolidin-1-ylpropyl)-1H-indole-5-carboxamide (CAS Registry No. 895098-04-1), 1-(4-chlorobenzyl)-2,3-dimethyl-N-[3-(2-methylpiperidin-1-yl)propyl]-1H-indole-5-carboxamide (CAS Registry No. 895098-00-7), N-(3-azepan-1-ylpropyl)-1-(4-chlorobenzyl)-2,3-dimethyl-1H-indole-5-carboxamide (CAS Registry No. 895097-96-8), 1-(4-chlorobenzyl)-2,3-dimethyl-N-(3-piperidin-1-ylpropyl)-1H-indole-5-carboxamide (CAS Registry No. 895097-88-8), 1-(4-chlorobenzyl)-2,3-dimethyl-N-[3-(4-methylpiperazin-1-yl)propyl]-H-indole-5-carboxamide (CAS Registry No. 895097-84-4), 1-(4-chlorobenzyl)-2,3-dimethyl-N-(2-morpholin-4-ylethyl)-1H-indole-5-carboxamide (CAS Registry No. 895097-63-9), 1-(4-chlorobenzyl)-2,3-dimethyl-N-(3-morpholin-4-ylpropyl)-1H-indole-5-carboxamide (CAS Registry No. 895096-80-7), N-[2-(dimethylamino)ethyl]-1-(4-fluorobenzyl)-2,3-dimethyl-1H-indole-5-carboxamide (CAS Registry No. 895120-70-4), N-{3-[benzyl(ethyl)amino]propyl}-1-(4-chlorobenzyl)-2,3-dimethyl-1H-indole-5-carboxamide (CAS Registry No. 895098-21-2), N-{3-[butyl(ethyl)amino]propyl}-1-(4-chlorobenzyl)-2,3-dimethyl-1H-indole-5-carboxamide (CAS Registry No. 895098-17-6), 1-(4-chlorobenzyl)-N-{3-[ethyl(3-methylphenyl)amino]propyl}-2,3-dimethyl-1H-indole-5-carboxamide (895097-92-4), and 1-(4-chlorobenzyl)-N-2-(dimethylamino)ethyl]-2,3-dimethyl-1H-indole-5-carboxamide (CAS Registry No. 895096-32-9), N-[(1-ethylpyrrolidin-2-yl)methyl]-1-(4-methoxybenzyl)-2-oxo-2,3-dihydro-1H-benzimidazole-5-carboxamide (CAS Registry No. 878688-87-0) and N-(1-benzylpiperidin-4-yl)-2-oxo-1-(2-phenylethyl)-2,3-dihydro-1H-benzimidazole-5-carboxamide (CAS Registry No. 846563-24-4) have been reported. However, there are no reports on the $5\text{-HT}_{2B}$ and $5\text{-HT}_7$ receptor antagonistic activities of these compounds and their efficacy for IBS.

Non-patent Reference 1: "Pharmacological Reviews", (USA), 1994, vol. 46, p. 157-203

Non-patent Reference 2: "Gut", (England), 1998, vol. 42. p. 42-46

Non-patent Reference 3: "The American Journal of Gastroenterology", (USA), 2000, vol. 95, p. 2698-2709

Non-patent Reference 4: "The American Journal of Gastroenterology", (USA), 2003, vol. 98, p. 750-758

Non-patent Reference 5: "Drugs", (New Zealand), 2001, vol. 61, no. 3, p. 317-332

Non-patent Reference 6: "British Journal of Pharmacology", (England), 1995, vol. 114, p. 1525-1527

Non-patent Reference 7: "British Journal of Pharmacology", (England), 2002, vol. 135, p. 1144-1151

Non-patent Reference 8: "European Journal of Pharmacology", (Holland), 1995, vol. 280, p. 243-250

Non-patent Reference 9: "Life Science", (Holland), 2001, vol. 69, p. 2467-2475

Non-patent Reference 10: "British Journal of Pharmacology", (England), 2003, vol. 138, p. 1210-1214

Non-patent Reference 11: "Tetrahedron Letters", (Holland), 2003, vol. 44, p. 2807-2811

Patent Reference 1: International Publication No. 2006/085510

Patent Reference 2: International Publication No. 2005/79845

Patent Reference 3: International Publication No. 2005/80322

Patent Reference 4: Published European Patent Application No. 622356

Patent Reference 5: U.S. Pat. No. 5,852,046

Patent Reference 6: JP-A-2005-162657

Patent Reference 7: JP-A-8-48671

DISCLOSURE OF THE INVENTION

Problems that the Invention is to Solve

As described in the above, the existing agents for treating IBS are not satisfactory from the viewpoints of the efficacy, safety and the like, so that great concern has been directed toward the provision of an IBS-treating agent having superior efficacy and safety.

Means for Solving the Problems

As described in the above, it is expected that a compound having the antagonistic activity for $5\text{-HT}_{2B}$ and $5\text{-HT}_7$ receptors becomes an IBS-treating agent having less side effects and excellent efficacy. Accordingly, with the aim of providing a compound useful as an IBS-treating agent, the present inventors have conducted intensive studies on a compound having the antagonistic activity for $5\text{-HT}_{2B}$ and $5\text{-HT}_7$ receptors. As a result, it was found that amide derivatives having a nitrogen-containing bicyclic hetero ring (e.g., indole or the like), represented by the following general formula (I), has excellent antagonism for both of the $5\text{-HT}_{2B}$ and $5\text{-HT}_7$ receptors. In addition, by finding that these amide derivatives have superior IBS treating effect in comparison with the conventional compounds which have the antagonistic activity for only one of the $5\text{-HT}_{2B}$ and $5\text{-HT}_7$ receptors, the present invention has been accomplished.

That is, the present invention relates to a pharmaceutical composition comprising an amide derivative represented by a general formula (I) or a pharmaceutically acceptable salt thereof and a pharmaceutically acceptable carrier, and a pharmaceutical comprising an amide derivative represented by the general formula (I) or a salt thereof as the active ingredient, particularly a $5\text{-HT}_{2B}$ receptor and $5\text{-HT}_7$ receptor dual antagonist.

(1) A pharmaceutical composition comprising an amide derivative represented by a general formula (I) or a pharmaceutically acceptable salt thereof and a pharmaceutically acceptable carrier:

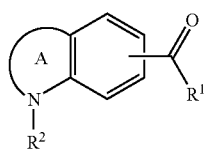
(I)

[symbols in the formula have the following meanings;
R$^1$: —N═C(NH$_2$)$_2$, —NR$^{11}$R$^{12}$ or R$^{13}$,

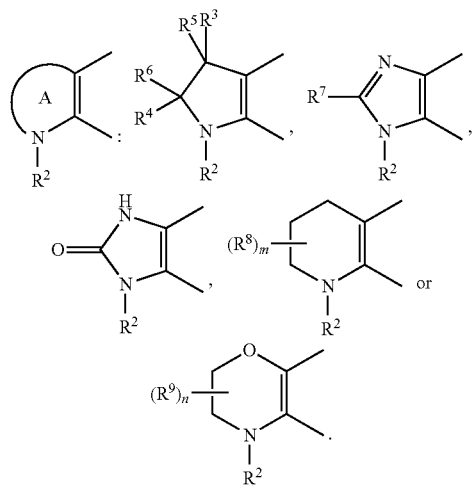

m and n: an integer of from 0 to 2,
R$^8$ and R$^9$: the same or different from each other and each represents lower alkyl,
R$^{11}$: —H, lower alkyl or lower alkylene-aryl,
wherein the aryl in R$^{11}$ may be substituted,
R$^{12}$: nitrogen-containing saturated heterocyclic group, lower alkylene-N(R$^{14}$)$_2$, lower alkylene-nitrogen-containing saturated heterocyclic group, lower alkylene-C(O)—R$^{13}$ or lower alkylene-R$^{15}$,
wherein the lower alkylene and nitrogen-containing saturated heterocyclic group in R$^{12}$ may be respectively substituted,
R$^{13}$: nitrogen-containing saturated hetero ring which has a linkage on a nitrogen atom as the ring atom and may be substituted,
with the proviso that when the nitrogen atom contained in the nitrogen-containing saturated hetero ring in R$^{13}$ is one, at least one is substituted with a group selected from a group G,
R$^{14}$: the same or different from each other, and each represents —H, lower alkyl, lower alkylene-OR$^0$, lower alkylene-aryl or aryl,
wherein the aryl in R$^{14}$ may be substituted,
R$^0$: each independently —H or lower alkyl,
R$^{15}$: cycloalkyl, aryl or heterocyclic group which is respectively substituted, with the proviso that at least one is substituted with a group selected from the group G,
group G: —N(R$^{14}$)$_2$, nitrogen-containing saturated heterocyclic group, -lower alkylene-N(R$^{14}$)$_2$ and -lower alkylene-nitrogen-containing saturated heterocyclic group, wherein the nitrogen-containing saturated heterocyclic group in the group G may be substituted, wherein
(I) when R$^1$ is —N═C(NH$_2$)$_2$,
[R$^2$: —H, lower alkyl, halogeno-lower alkyl, cycloalkyl, aryl, heterocyclic group, —CH(aryl)$_2$ or lower alkylene-R$^{21}$,
wherein the aryl and heterocyclic group in R$^2$ may be respectively substituted,
R$^{21}$: —OR$^0$, —O-aryl, —N(R$^0$)$_2$, —CH(OH)R$^0$, —C(O)R$^0$, —C(O)-aryl, —CO$_2$R$^0$, —C(O)N(R$^0$)$_2$, cycloalkyl, aryl, heterocyclic group or CH(aryl)$_2$,
wherein the aryl and heterocyclic group in R$^{21}$ may be respectively substituted],
R$^3$, R$^4$ and R$^7$: —H, lower alkyl, halogeno-lower alkyl, lower alkylene-OR$^0$, lower alkylene-N(R$^0$)$_2$, —O-lower alkyl, —S-lower alkyl, —S(O)-lower alkyl, —S(O)$_2$-lower alkyl, —C(O)R$^0$, —CO$_2$R$^0$ or —C(O)N(R$^0$)$_2$, and
R$^5$ and R$^6$: —H, or R$^5$ and R$^6$ may together form a bond,
wherein the substituting position of —C(O)R$^1$ may be any optional position on the benzene ring with which ring A is condensed], or
(II) when R$^1$ is —NR$^{11}$R$^{12}$ or R$^{13}$,
[R$^2$: lower alkylene-aryl or lower alkylene-heterocyclic group, wherein the aryl and heterocyclic group in R$^2$ may be respectively substituted,
R$^3$, R$^4$ and R$^7$; lower alkyl, lower alkylene-OR$^0$, —C(O)R$^0$, —S-lower alkyl, —S(O)-lower alkyl or —S(O)$_2$-lower alkyl,
R$^5$ and R$^6$: R$^5$ and R$^6$ together form a bond,
wherein the substituting position of —C(O)R$^1$ is at the para-position of N(R$^2$); the same shall apply hereinafter].

(2) The pharmaceutical composition described in (1), which is a 5-HT$_{2B}$ receptor and 5-HT$_7$ receptor dual antagonist.

(3) The pharmaceutical composition described in (1), which is an agent for treating irritable bowel syndrome.

(4) Use of the compound described in formula (I) or a pharmaceutically acceptable salt thereof for the manufacture of a 5-HT$_{2B}$ receptor and 5-HT$_7$ receptor dual antagonist or an agent for treating irritable bowel syndrome.

(5) A method for treating irritable bowel syndrome, which comprises administering a therapeutically effective amount of the compound described in (1) or a salt thereof to a patient.

In addition, the present invention relates to a novel compound, an amide derivative represented by a formula (I-a), or a pharmaceutically acceptable salt thereof:

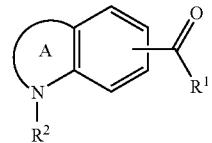
(I-a)

[symbols in the formula have the following meanings;
R$^1$: —N═C(NH$_2$)$_2$, —NR$^{11}$R$^{12}$ or R$^{13}$,

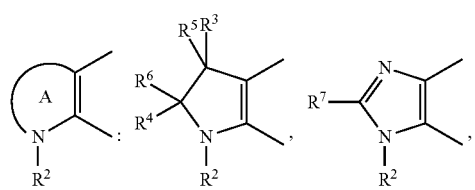

-continued

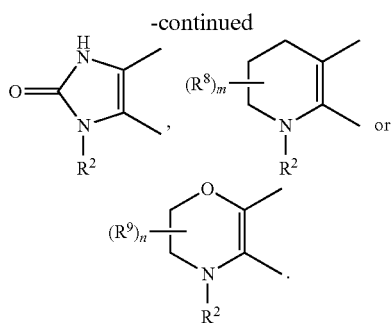

m and n: an integer of from 0 to 2,
$R^8$ and $R^9$: the same or different from each other and each represents lower alkyl,
$R^{11}$: —H, lower alkyl or lower alkylene-aryl,
wherein the aryl in $R^{11}$ may be substituted,
$R^{12}$: nitrogen-containing saturated heterocyclic group, lower alkylene-N$(R^{14})_2$, lower alkylene-nitrogen-containing saturated heterocyclic group, lower alkylene-C(O)—$R^{13}$ or lower alkylene-$R^{15}$,
wherein the lower alkylene and nitrogen-containing saturated heterocyclic group in $R^{12}$ may be respectively substituted,
$R^{13}$: nitrogen-containing saturated hetero ring which has a linkage on a nitrogen atom as the ring atom and may be substituted,
with the proviso that when the nitrogen atom contained in the nitrogen-containing saturated hetero ring in $R^{13}$ is one, at least one is substituted with a group selected from a group G,
$R^{14}$: the same or different from each other, and each represents —H, lower alkyl, lower alkylene-OR$^0$, lower alkylene-aryl or aryl,
wherein the aryl in $R^{14}$ may be substituted,
$R^0$: each independently —H or lower alkyl,
$R^{15}$: cycloalkyl, aryl or heterocyclic group which is respectively substituted, wherein at least one is substituted with a group selected from the group G,
group G: —N$(R^{14})_2$, nitrogen-containing saturated heterocyclic group, -lower alkylene-N$(R^{14})_2$ and -lower alkylene-nitrogen-containing saturated heterocyclic group, wherein the nitrogen-containing saturated heterocyclic group in the group G may be substituted, wherein
(I) when $R^1$ is —N═C(NH$_2$)$_2$,
[$R^2$: —H, lower alkyl, halogeno-lower alkyl, cycloalkyl, aryl, heterocyclic group, —CH(aryl)$_2$ or lower alkylene-$R^{21}$,
wherein the aryl and heterocyclic group in $R^2$ may be respectively substituted,
$R^{21}$: —OR$^0$, —O-aryl, —N$(R^0)_2$, —CH(OH)R$^0$, —C(O)R$^0$, —C(O)-aryl, —CO$_2$R$^0$, —C(O)N$(R^0)_2$, cycloalkyl, aryl, heterocyclic group or CH(aryl)$_2$,
wherein the aryl and heterocyclic group in $R^{21}$ may be respectively substituted],
$R^3$, $R^4$ and $R^7$: —H, lower alkyl, halogeno-lower alkyl, lower alkylene-OR$^0$, lower alkylene-N$(R^0)_2$, —O-lower alkyl, —S-lower alkyl, —S(O)-lower alkyl, —S(O)$_2$-lower alkyl, —C(O)R$^0$, —CO$_2$R$^0$ or —C(O)N$(R^0)_2$, and
$R^5$ and $R^6$: —H, or $R^5$ and $R^6$ may together form a bond,
wherein the substituting position of —C(O)R$^1$ may be any optional position on the benzene ring with which ring A is condensed,
with the proviso that, (1) when the bicyclic ring formed by the ring A and benzene ring is indole ring, and $R^2$ is —H, methyl, isopropyl or unsubstituted benzyl, at least one of $R^3$ and $R^4$ is not —H,
(2) when the bicyclic ring formed by the ring A and benzene ring is benzimidazole ring, and $R^2$ is —H, methyl, normal hexyl or 2-chlorobenzyl, $R^7$ is not —H, methyl or —S-methyl], or
(II) when $R^1$ is —NR$^{11}$R$^{12}$ or $R^{13}$,
[$R^2$: lower alkylene-aryl or lower alkylene-heterocyclic group, wherein the aryl and heterocyclic group in $R^2$ may be respectively substituted,
$R^3$, $R^4$ and $R^7$: lower alkyl, lower alkylene-OR$^0$, —C(O)R$^0$, —S-lower alkyl, —S(O)-lower alkyl or —S(O)$_2$-lower alkyl,
$R^5$ and $R^6$: $R^5$ and $R^6$ together form a bond,
with the proviso that the substituting position of —C(O)R$^1$ is at the para-position of N$(R^2)$,
with the proviso that when the bicyclic ring formed by the ring A and benzene ring is benzimidazole ring, $R^2$ is not 4-carbamoylbenzyl],
with the proviso that
  1-benzyl-N-[2-(dimethylamino)ethyl]-2,3-dimethyl-1H-indole-5-carboxamide,
  1-benzyl-5-[(4-ethylpiperazin-1-yl)carbonyl]-2,3-dimethyl-1H-indole,
  5-[(4-ethylpiperazin-1-yl)carbonyl]-1-(4-fluorobenzyl)-2,3-dimethyl-1H-indole,
  1-(3,4-dichlorobenzyl)-5-[(4-ethylpiperazin-1-yl)carbonyl]-2,3-dimethyl-1H-indole,
  1-benzyl-2-ethyl-5-[(4-ethylpiperazin-1-yl)carbonyl]-3-methyl-1H-indole,
  1-benzyl-5-[(4-benzylpiperazin-1-yl)carbonyl]-2,3-dimethyl-1H-indole,
  5-[(4-benzoylpiperazin-1-yl)carbonyl]-1-benzyl-2,3-dimethyl-1H-indole,
  1-(1-{[1-(4-fluorobenzyl)-2,3-dimethyl-1H-indol-5-yl]carbonyl}piperidin-2-yl)-N,N-dimethylmethanamine,
  4-{[2-butyl-5-(piperazin-1-ylcarbonyl)-1H-benzimidazol-1-yl]methyl}benzoic acid,
  N-[amino(imino)methyl]-1-(2-chlorobenzyl)-2-oxo-2,3-dihydro-1H-benzimidazole-5-carboxamide,
  N-[amino(imino)methyl]-1-hexyl-2-oxo-2,3-dihydro-1H-benzimidazole-5-carboxamide,
  N-[(1-ethylpyrrolidin-2-yl)methyl]-1-(4-methoxybenzyl)-2-oxo-2,3-dihydro-1H-benzimidazole-5-carboxamide,
  N-(1-benzylpiperidin-4-yl)-2-oxo-1-(2-phenylethyl)-2,3-dihydro-1H-benzimidazole-5-carboxamide,
  N-(1-benzylpiperidin-4-yl)-1-(4-methoxybenzyl)-2-oxo-2,3-dihydro-1H-benzimidazole-5-carboxamide and
  N-(1-benzylpiperidin-4-yl)-1-(4-fluorobenzyl)-2-oxo-2,3-dihydro-1H-benzimidazole-5-carboxamide
are excluded; the same shall apply hereinafter].

EFFECTS OF THE INVENTION

The compound of the present invention showed excellent antagonistic activity for both of the 5-HT$_{2B}$ and 5-HT$_7$ receptors. In addition, the compound of the present invention showed superior IBS-treating effect in comparison with the conventional compounds which have the antagonistic activity for only one of the 5-HT$_{2B}$ and 5-HT$_7$ receptors. Accordingly, the compound of the present invention is useful as an agent for treating IBS.

BEST MODE FOR CARRYING OUT THE INVENTION

Figure 1:
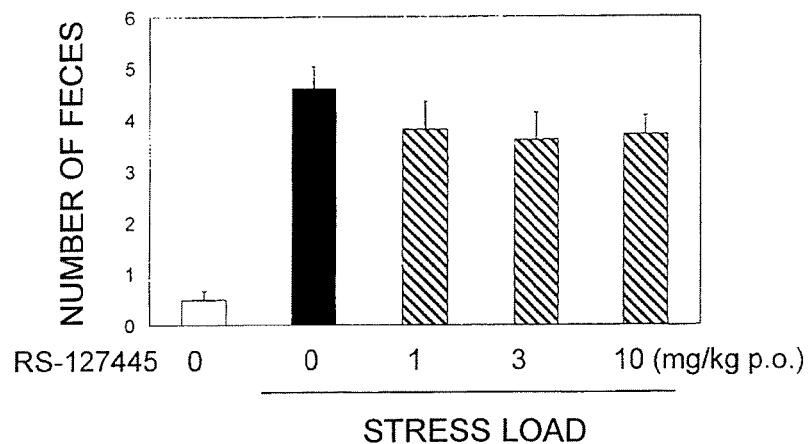
FIG. 1 is a graph showing a result of the measurement of the number of feces excreted at the time of RS-127445 administration, in the rat restraint stress defecation model of the test method (4). Significant difference was not found in the 1, 3 or 10 mg/kg administration group in comparison with the non-administration group (N=10).

Further detailed description of the present invention is as follows.

Unless otherwise noted, each of the terms "lower alkyl" and "lower alkylene" as used herein means a hydrocarbon chain having from 1 to 6 carbon atoms (to be referred sometimes to as $C_{1-6}$ hereinafter) which may be in a straight or branched form.

Thus, the "lower alkyl" means a $C_{1-6}$ alkyl, which is illustratively, for example, methyl, ethyl, propyl, butyl, pentyl or hexyl, or structural isomer thereof (e.g., isopropyl, isobutyl, tert-butyl or the like), preferably a $C_{1-4}$ alkyl, more preferably methyl, ethyl, propyl or isopropyl.

The "alkylene" means a divalent group in which one hydrogen at an optional position of alkyl is removed. The "lower alkylene" means a $C_{1-6}$ alkylene. Illustratively, it is methylene, ethylene, methylmethylene, dimethylmethylene, propylene, butylene, pentylene, hexylene and the like. Preferred is a $C_{1-3}$ alkylene, and more preferred is methylene, ethylene, methylmethylene, dimethylmethylene or propylene.

The "cycloalkyl" means a $C_{3-10}$ non-aromatic hydrocarbon ring, and it may form a bridged ring or spiro ring. In addition, it may partially have an unsaturated bond, and benzene ring may be condensed therewith. However, when benzene ring is condensed, the linkage is present on the non-aromatic ring. Illustratively, for example, cyclopropyl, cyclobutyl, cyclopentyl, cyclohexyl, cyclooctyl, cyclohexenyl, cyclooctanedienyl, adamantyl, norbornyl, indanyl having linkages at the 1- to 3-positions and the like may be cited, and preferred is cyclopropyl, cyclobutyl, cyclopentyl or cyclohexyl.

The "halogen" means a halogen atom, and for example, fluoro, chloro, bromo, iodo and the like may be illustratively cited, of which fluoro or chloro is preferable.

The "halogeno-lower alkyl" means a group in which one or more of optional hydrogen atoms of the aforementioned "lower alkyl" are substituted with the aforementioned "halogen" that are the same or different from each other. Illustratively, trifluoromethyl, pentafluoroethyl and the like may be exemplified. Preferred is trifluoromethyl.

The "aryl" means a monocyclic to tricyclic $C_{6-14}$ aromatic hydrocarbon ring, and for example, phenyl, naphthyl and the like may be illustratively cited, of which phenyl is preferable. In addition, a $C_{5-8}$ cycloalkyl ring may be condensed therewith. However, when the cycloalkyl ring is condensed, the linkage is present on the aromatic ring. For example, indanyl having linkages at the 4- to 7-positions or tetrahydronaphthyl having linkages at the 5- to 8-positions may be formed.

The "hetero ring" means a monocyclic 3- to 12-membered saturated, partially unsaturated or aromatic monocyclic hetero ring, a bicyclic hetero ring in which said monocyclic hetero rings are mutually condensed or said monocyclic hetero ring is condensed with cycloalkyl ring or benzene ring, or tricyclic hetero ring in which said bicyclic hetero ring is condensed with a monocyclic hetero ring, cycloalkyl ring or benzene ring, which contains 1 to 4 hetero atoms selected from O, S and N. The S or N as a ring atom may be oxidized to form an oxide or dioxide, or may form a bridged ring or spiro ring. As the monocyclic hetero ring, for example, pyrrolyl, furyl, thienyl, oxazolyl, isoxazolyl, oxadiazolyl, thiazolyl, thiadiazolyl, imidazolyl, triazolyl, tetrazolyl, pyridyl, pyridazinyl, pyrimidinyl, pyrazinyl, azolizinyl, azetidinyl, oxetanyl, pyrrolidinyl, piperidinyl, piperazinyl, morpholinyl, homopiperidinyl, homomorpholinyl, tetrahydrofuranyl, tetrahydropyranyl, tetrahydrothiopyranyl and the like may be cited. As the bicyclic hetero ring, for example, indolyl, benzofuranyl, benzothienyl, benzoxazolyl, benzoisoxazolyl, benzoimidazolyl, benzothiazolyl, quinolyl, isoquinolyl, quinazolinyl, quinoxalinyl, cinnolinyl, indolinyl, tetrahydroquinolinyl, tetrahydroisoquinolinyl, octahydropyrolo[1,2-a]pyrazinyl, octahydro-2H-pyrido[1,2-a]pyrazinyl and the like may be cited. As the tricyclic hetero ring, for example, carbazolyl, phenoxazinyl, fluorenyl and the like may be cited. As the bridged ring, quinuclidinyl, 3,8-diazabicyclo[3.2.1]octanyl and the like may be cited. Preferred is furyl, thienyl, pyridyl, azetidinyl, pyrrolidinyl, piperidinyl, piperazinyl, morpholinyl, tetrahydrofuranyl, tetrahydropyranyl or quinuclidinyl.

The "nitrogen-containing saturated hetero ring" means a saturated hetero ring among the aforementioned "hetero ring", which contains one or more nitrogen atoms.

For example, azetidinyl, pyrrolidinyl, piperidinyl, piperazinyl, morpholinyl, homopiperidinyl, homomorpholinyl, quinuclidinyl, 3,8-diazabicyclo[3.2.1]octanyl, octahydropyrolo-1,2-a]pyrazinyl, octahydro-2H-pyrido[1,2-a]pyrazinyl and the like may be cited. Preferred are azetidinyl, pyrrolidinyl, piperidinyl, piperazinyl, morpholinyl and quinuclidinyl.

The "may be substituted" means "not substituted" or "substituted with 1 to 5 substituent groups which may be the same or different from one another".

The acceptable substituent group of the term "may be substituted" as used herein may be any substituent group which is generally used in said technical field as the substituent group of respective groups. In addition, when there are two or more groups like the case of the $R^0$ of —C(O)N($R^0$)$_2$, the respective groups may be the same or different from each other.

A group selected from the following group $G^1$ may be exemplified as a preferred acceptable substituent group of the "aryl" which may be substituted in $R^{11}$, "aryl" which may be substituted in $R^{14}$ and "nitrogen-containing saturated heterocyclic group" which may be substituted in the group G.

Group $G^1$: halogen, lower alkyl, —OR$^0$, —O-halogeno-lower alkyl and oxo.

As the acceptable substituent group of the "lower alkylene" which may be substituted in $R^{12}$, a group selected from halogen and aryl may be preferably cited.

As the acceptable substituent group of the "nitrogen-containing saturated heterocyclic group" which may be substituted in $R^{12}$, a group selected from the following group $G^2$ may be preferably cited. More preferred is halogen, lower alkyl, —OR$^0$ or —O-halogeno-lower alkyl, and further preferred is lower alkyl. Group $G^2$: halogen, lower alkyl, —OR$^0$, —O-halogeno-lower alkyl, lower alkylene-OR$^0$, lower alkylene-N(R$^0$)$_2$, lower alkylene-cycloalkyl, lower alkylene-aryl, —CH(aryl)$_2$, lower alkylene-O-aryl, lower alkylene-hetero ring, cycloalkyl, aryl and hetero ring, wherein the aryl and heterocyclic group in the group $G^2$ may be substituted with a group selected from the aforementioned group $G^1$.

As the acceptable substituent group in the "nitrogen-containing saturated heterocyclic group" which may be substituted in $R^{13}$, and the "cycloalkyl", "aryl" and "heterocyclic group" which are respectively substituted in $R^{15}$, groups selected from the group G and the aforementioned group $G^2$ may be preferably exemplified. More preferred is halogen, lower alkyl, —OR$^0$ or —O-halogeno-lower alkyl, and further preferred is lower alkyl.

As the acceptable substituent group in the "aryl" and "heterocyclic group" which may be substituted in $R^2$ and the "aryl" and "heterocyclic group" which may be substituted in $R^{21}$, groups selected from the following group $G^3$ may be preferably exemplified. More preferred is halogen, lower alkyl, —OR$^0$ or —O-halogeno-lower alkyl, and further preferred is halogen.

Group $G^3$: halogen, nitro, cyano, lower alkyl, halogeno-lower alkyl, —OR$^0$, —O-halogeno-lower alkyl, —N(R$^0$)$_2$, —S(O)$_2$-lower alkyl, oxo, cycloalkyl, aryl and hetero ring, wherein the aryl and heterocyclic group in the group $G^3$ may be substituted with a group selected from the aforementioned group $G^1$.

Preferred embodiments of the present invention are shown in the following.

(1) Preferred as the nitrogen-containing bicyclic hetero ring formed by the condensation of ring A and benzene ring is indole ring or benzimidazole ring, more preferred is indole ring.

(2) Preferred as $R^1$ is —N═C(NH$_2$)$_2$, —N(R$^0$)-(nitrogen-containing saturated heterocyclic group which may be substituted), —N(R$^0$)-lower alkylene-N(lower alkyl)$_2$, —N(R$^0$)-lower alkylene-(nitrogen-containing saturated heterocyclic group which may be substituted), —N(R$^0$)-lower alkylene-(heterocyclic group substituted with —N(lower alkyl)$_2$) or —N(R$^0$)-lower alkylene-(cycloalkyl substituted with —N(lower alkyl)$_2$), more preferred is —N═C(NH$_2$)$_2$, —N(R$^0$)-(nitrogen-containing saturated heterocyclic group which may be substituted), —N(R$^0$)-lower alkylene-N(lower alkyl)$_2$ or —N(R$^0$)-lower alkylene-(nitrogen-containing saturated heterocyclic group which may be substituted), further preferred is —N═C(NH$_2$)$_2$, —N(R$^0$)-(nitrogen-containing saturated heterocyclic group which may be substituted with lower alkyl), —N(R$^0$)-lower alkylene-N(lower alkyl)$_2$ or —N(R$^0$)-lower alkylene-(nitrogen-containing saturated heterocyclic group which may be substituted with lower alkyl), further more preferred is —N═C(NH$_2$)$_2$, —NH-(nitrogen-containing saturated heterocyclic group which may be substituted with lower alkyl), —NH-lower alkylene-N(lower alkyl)$_2$ or —NH-lower alkylene-(nitrogen-containing saturated heterocyclic group which may be substituted with lower alkyl), and particularly preferred is —N═C(NH$_2$)$_2$ or —NH-(nitrogen-containing saturated heterocyclic group which may be substituted with lower alkyl).

(2) Preferred as $R^2$ is lower alkylene-(aryl which may be substituted) or lower alkylene-(heterocyclic group which may be substituted), more preferred is lower alkylene-(phenyl which may be substituted), further preferred is lower alkylene-(phenyl which may be substituted with halogen), further more preferred is —CH$_2$— (phenyl which may be substituted with halogen), and particularly preferred is —CH$_2$— (phenyl which is substituted with halogen).

(3) Preferred as $R^3$ is lower alkyl or —C(O)R$^0$, and more preferred is methyl, ethyl or acetyl.

(4) Preferred as $R^4$ is lower alkyl, and more preferred is methyl or ethyl.

(5) Preferred as $R^5$ and $R^6$ is a bond jointly formed by $R^5$ and $R^6$.

(6) Preferred as $R^7$ is lower alkyl, more preferred is methyl.

(7) Preferred as $R^8$ and $R^9$ is methyl.

(8) Preferred as m and n is 0.

(9) When $R^1$ is —N═C(NH$_2$)$_2$, the substituting position of —C(O)R$^1$ on the benzene ring is preferably at the para-position of N(R$^2$)

As other preferred embodiment, a compound consisting of a combination of the respective groups described in the above-mentioned (1) to (9) is desirable.

In addition, further other preferred embodiments are shown in the following.

(1) A compound described in the formula (I-a), which is represented by the following formula (I-b)

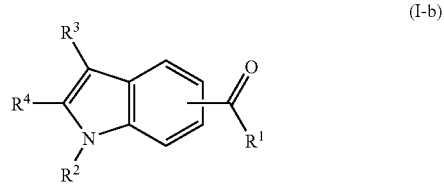

(I-b)

[the symbols $R^1$, $R^2$, $R^3$ and $R^4$ in the formula have the same meanings of the compound represented by the formula (I-a)].

(2) The compound described in (1), wherein $R^4$ is lower alkyl.

(3) The compound described in (2), wherein $R^3$ is lower alkyl or —C(O)R$^9$.

(4) The compound described in (3), wherein $R^2$ is lower alkylene-(phenyl which may be substituted with halogen).

(5) The compound described in (4), wherein $R^1$ is —N═C(NH$_2$)$_2$, —N(R$^0$)-(nitrogen-containing saturated heterocyclic group which may be substituted with lower alkyl), —N(R$^0$)-lower alkylene-N(lower alkyl)$_2$ or —N(R$^0$)-lower alkylene-(nitrogen-containing saturated heterocyclic group which may be substituted with lower alkyl).

(6) The compound described in (5), wherein $R^1$ is —N=C(NH$_2$)$_2$ or —NH-(nitrogen-containing saturated heterocyclic group which may be substituted with lower alkyl).

(7) A compound described in the formula (I-a), which is represented by the following formula (I-c)

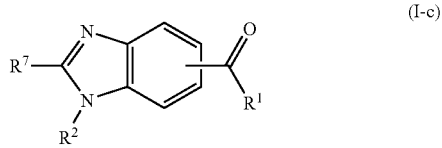

(I-c)

[the symbols $R^1$, $R^2$ and $R^7$ in the formula have the same meanings of the compound represented by the formula (I-a)].

(8) The compound described in (7), wherein $R^7$ is lower alkyl.

(9) The compound described in (8), wherein $R^2$ is lower alkylene-(phenyl which may be substituted with halogen).

(10) The compound described in (9), wherein $R^1$ is —N=C(NH$_2$)$_2$, —N(R$^0$)— (nitrogen-containing saturated heterocyclic group which may be substituted with lower alkyl), —N(R$^0$)-lower alkylene-N(lower alkyl)$_2$ or —N(R$^0$)-lower alkylene-(nitrogen-containing saturated heterocyclic group which may be substituted with lower alkyl).

(11) The compound described in (10), wherein $R^1$ is —N=C(NH$_2$)$_2$ or —NH-(nitrogen-containing saturated heterocyclic group which may be substituted with lower alkyl).

(12) A compound described in the formula (I-a), which is selected from the group consisting of
3-ethyl-1-(4-fluorobenzyl)-2-methyl-N-[(3S)-1-methylpyrrolidin-3-yl]-1H-indole-5-carboxamide,
N-(diaminomethylene)-3-ethyl-1-(4-fluorobenzyl)-2-methyl-1H-indole-5-carboxamide,
3-acetyl-N-(diaminomethylene)-1-(4-fluorobenzyl)-2-methyl-1H-indole-5-carboxamide and
N-(diaminomethylene)-1-(4-fluorobenzyl)-2-methyl-1H-benzimidazol-5-carboxamide, or a pharmaceutically acceptable salt thereof.

In addition, the "binding affinity" as used herein means the ability of a compound to be tested to bind to a part of a receptor, and evaluation of this is carried out by, as described in the test method, comparing the Ki value calculated by the in vitro receptor binding test or the IC$_{50}$ value of a receptor binding test carried out under the same conditions as occasion demands. In this connection, when a sufficient inhibitory action is not shown at a predetermined concentration in the receptor binding test so that the IC$_{50}$ value cannot be calculated, the IC$_{50}$ value of the compound is regarded in some cases as said concentration or more.

When binding affinity of the compound of the present invention for the 5-HT$_{2B}$ and 5-HT$_7$ receptors is "selective" in comparison with other receptors, it means that the binding affinity for said receptors is high in comparison with the binding affinity for "other receptors". According to the present invention, the "selective" means a case in which the Ki value or IC$_{50}$ value showing the binding affinity for said receptors is 1/10 or less in comparison with the value for "other receptors", and this value is more preferably 1/50 or less, further preferably 1/100 or less, more further preferably 1/500 or less, and particularly preferably 1/1000 or less.

In this connection, the "other receptors" are receptors other than the 5-HT$_{2B}$ and 5-HT$_7$ receptors, which have been reported in relation to the existing nonselective 5-HT receptor antagonists, and are receptors which are particularly concerned in undesirable actions. Thus, preferred as the compounds of the present invention are compounds whose binding affinity for 5-HT$_{2B}$ and 5-HT$_7$ receptors is selective in comparison with $\alpha_1$, M$_1$ and D$_2$ receptors, and more preferred are compounds whose binding affinity for 5-HT$_{2B}$ and 5-HT$_7$ receptors is selective in comparison with $\alpha_1$, M$_1$, D$_2$, 5-HT$_{1A}$, 5-HT$_{1B}$, 5-HT$_{2A}$, 5-HT$_{2C}$, 5-HT$_3$, 5-HT$_4$ and 5-HT$_6$ receptors.

There are cases in which geometrical isomers and tautomers are present in the compound (I) of the present invention. For example, the following tautomers are present.

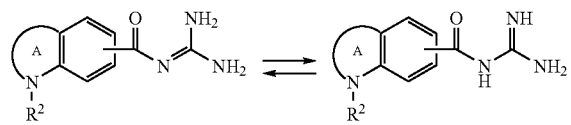

The present invention includes one of such tautomers or a mixture thereof. In addition, the compound of the present invention exists in isomer forms based on asymmetric carbon atom in some cases. The present invention includes mixtures of these optical isomers and isolated forms thereof.

In this connection, all of the compounds, so-called prodrugs, which are converted into compounds (I) or salts thereof in the living body by undergoing metabolism are also included in the compound (I) of the present invention. As the groups which form such prodrugs, the groups described in "Progress in Medicine", Lifescience Medica, 1985, vol. 5, p. 2157-2161, and the groups described in "Iyakuhin no Kaihatsu (Development of Medicines)", vol. 7, Bunshi Sekkei (Molecular Design), 163-198, published in 1990 by Hirokawa Shoten, may be exemplified.

As the pharmaceutically acceptable salt of the compound (I) of the present invention, illustratively, acid addition salts with inorganic acids (e.g., hydrochloric acid, hydrobromic acid, hydriodic acid, sulfuric acid, nitric acid, phosphoric acid and the like), organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like), and the like may be exemplified. Also, there is a case in which it forms a salt with a base depending on the kind of substituent groups, and for example, salts with inorganic bases including metals (e.g., sodium, potassium, magnesium, calcium, aluminum and the like) or with organic bases (e.g., methylamine, ethylamine, ethanolamine, lysine, ornithine and the like), ammonium salts, and the like may be exemplified.

In addition, the present invention also includes various hydrates and solvates and polymorphism of the compound (I) of the present invention or a salt thereof.
(Production Methods)

The compound (I) of the present invention and a pharmaceutically acceptable salt thereof may be produced by employing various known synthesis methods making use of the characteristics based on its basic skeleton or kind of the substituent groups. In that case, depending on the kind of functional group, there is an effective case from the production technology point of view to protect said functional group with an appropriate protecting group at the stage of starting materials to intermediates, or to replace it with a group which may be easily converted into said functional group. Examples of such a functional group include amino group, hydroxyl group, carboxyl group and the like, and as their protecting groups, the protecting groups described for example in "Protective Groups in Organic Synthesis" edited by T. W. Greene and P. G. M. Wuts, (USA), 3rd edition, John Wiley & Sons, 1999, may be cited, which may be optionally selected and used in response to the reaction conditions. By such a method, a desired compound may be obtained by introducing said protecting group and carrying out the reaction, and then removing the protecting group as occasion demands or converting it into a desired group.

The following describes typical production methods of the compounds of the present invention.

(First Production Method)

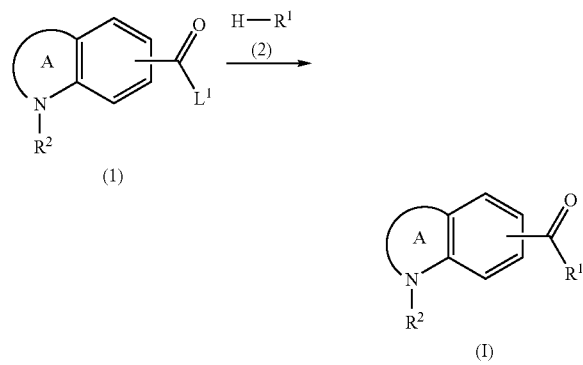

(In the formulae, $L^1$ represents —OH or a leaving group such as —O-lower alkyl, halogen, —O-methanesulfonyl, —O-p-toluenesulfonyl or the like. The same shall apply hereinafter.)

The compound (I) of the present invention may be produced by subjecting the compound represented by (1) which is a carboxylic acid or a reactive derivative thereof and an amine derivative (2) to amidation reaction.

When the starting compound (1) is used as a free carboxylic acid wherein $L^1$ is OH, a method in which the compound (1) and amine derivative (2) are dehydration-condensed in the presence of a condensing agent is used. As the condensing agent in this case, it is desirable to use N,N'-dicyclohexylcarbodiimide (DCC), 1-[3-(dimethylamino)propyl]-3-ethylcarbodiimide (WSC), 1,1'-carbonyldiimidazole (CDI), 2-(1H-benzotriazol-1-yl)-1,1,3,3-tetramethyluronium hexafluorophosphate (HBTU), diphenylphosphoryl azide (DPPA), phosphorus oxychloride, and further an additive agent as occasion demands (e.g., N-hydroxysuccinimide (HONSu), 1-hydroxybenzotriazole (HOBt) or the like).

The reaction is carried out using the compound (1) and amine derivative (2) in equivalent amount or one of them in excess amount, and using a condensing agent in equivalent amount or excess amount based on the carboxylic acid. It may be carried out under cooling to heating, preferably at from −20° C. to 60° C., in a reaction inert solvent such as aromatic hydrocarbons (e.g., benzene, toluene, xylene or the like), halogenated hydrocarbons (e.g., dichloromethane, 1,2-dichloroethane, chloroform or the like), ethers (e.g., diethyl ether, tetrahydrofuran (THF), dioxane, dimethoxyethane (DME) or the like), N,N-dimethylformamide (DMF), dimethyl sulfoxide (DMSO), ethyl acetate, acetonitrile, water or the like, or a mixture thereof.

When the starting compound (1) is used as a compound wherein $L^1$ is a leaving group, namely a reactive derivative of the carboxylic acid, an acid halide (acid chloride, acid bromide or the like), an acid anhydride (a mixed acid anhydride with phenyl carbonate, p-toluenesulfonic acid, isovaleric acid or the like or symmetric acid anhydride), an active ester (an ester which may be prepared using phenol which may be substituted with an electron attractive group such as nitro group, fluorine atom or the like, HOBt, HONSu or the like), a lower alkyl ester or the like may be used as the reactive derivative of carboxylic acid. Each of these reactive derivatives may be produced from the carboxylic acid using a reaction obvious to those skilled in the art.

The reaction may be carried out using the compound (1) and amine derivative (2) in equivalent amount or one of them in excess amount under cooling to heating, preferably at from −20° C. to 60° C., in a reaction inert solvent such as aromatic hydrocarbons, halogenated hydrocarbons, ethers, N,N-dimethylformamide (DMF), dimethyl sulfoxide (DMSO), ethyl acetate, acetonitrile, water or the like, or a mixed liquid thereof. In this connection, when a lower alkyl ester is used as the reactive derivative, it is desirable to carry out the reaction under room temperature to heating. Depending on the kind of the reactive derivative, it is sometimes advantageous for smoothly carrying out the reaction to undergo the reaction in the presence of a base (organic bases such as triethylamine, diisopropylethylamine, N-methylmorpholine, pyridine, 4-(N,N-dimethylamino)pyridine or the like or inorganic bases such as sodium bicarbonate or the like). Pyridine can also serve as the solvent.

(Second Production Method A)

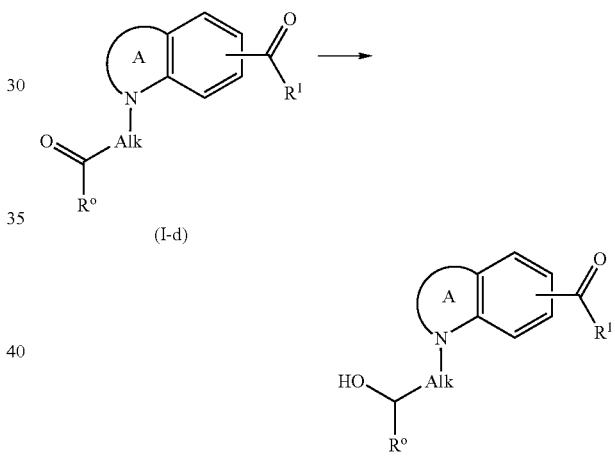

(In the formulae, Alk represents lower alkylene. The same shall apply hereinafter.)

Among the compound (I) of the present invention, a compound represented by the general formula (I-e) may be produced by subjecting a compound of the present invention represented by the general formula (I-d) to a reduction reaction.

The reaction is carried out by treating the compound (I-d) with an equivalent amount or excess amount of a reducing agent. As the reducing agent, a hydride-reducing agent such as sodium borohydride, diisobutylaluminum hydride or the like or the reducing agents described in "Comprehensive Organic Transformations" edited by Richard C. Larock (1989, VCH Publishers, Inc.) may be used. The reaction may be carried out under cooling to heating, preferably at from −20° C. to room temperature, in a reaction inert solvent such as aromatic hydrocarbons, ethers, DMF, DMSO, alcohols (methanol, ethanol and the like), water or the like, or in a mixed liquid thereof.

(Second Production Method B)

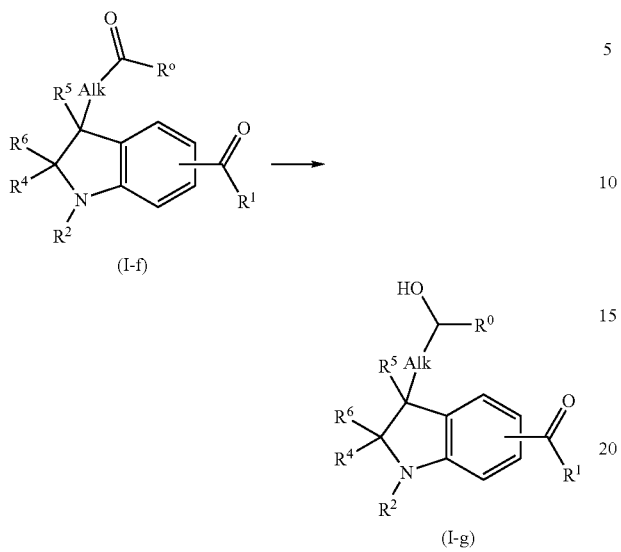

Among the compound (I) of the present invention, a compound represented by the general formula (I-g) may be produced by subjecting a compound of the present invention represented by the general formula (I-f) to a reduction reaction.

The reaction may be carried out in the same manner as in the second production method A.

(Third Production Method A)

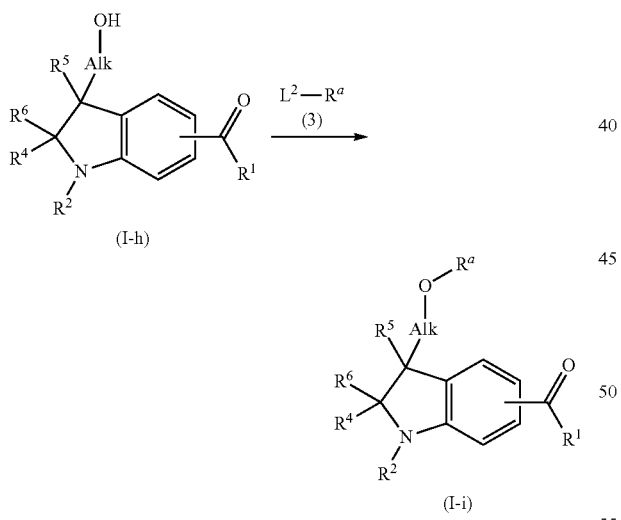

(In the formulae, $L^2$ represents a leaving group such as halogen, —O-methanesulfonyl, O-p-toluenesulfonyl or the like, and $R^a$ represents lower alkyl. The same shall apply hereinafter.)

Among the compound (I) of the present invention, a compound represented by the general formula (I-i) may be produced by allowing a compound of the present invention represented by the general formula (I-h) to react with various alkylating agents represented by the general formula (3) (e.g., an alkyl halide, an alkyl sulfonic acid ester or the like) in the presence of a base (e.g., potassium carbonate, potassium t-butoxide, sodium hydride, silver oxide or the like). Regarding the reaction, for example, the method described in "Jikken Kagaku Koza (Experimental Chemistry Course) (Maruzen)" edited by The Chemical Society of Japan (4th edition, vol. 20, 1992, 187) or the like may be employed.

(Third Production Method B)

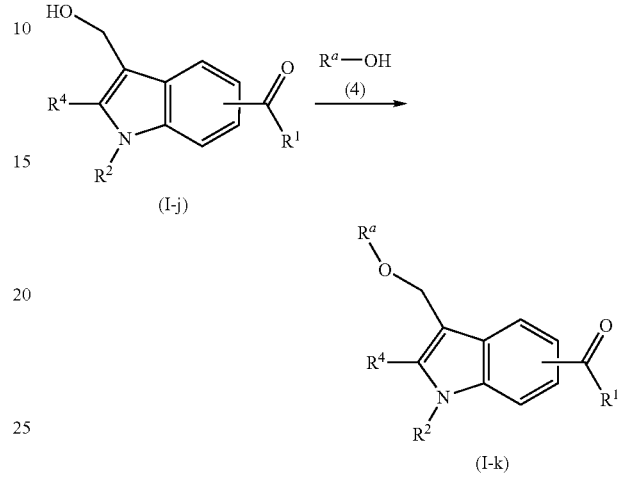

Among the compound (I) of the present invention, a compound represented by the general formula (I-k) may be produced by allowing a compound of the present invention represented by the general formula (I-j) to react with a compound represented by the general formula (4) in the presence of an acid (e.g., hydrochloric acid, sulfuric acid, trifluoroacetic acid, trifluoroborane, Lewis acid such as aluminum trichloride or the like).

The reaction is carried out using the compound (I-j) and compound (4) in equivalent amount or one of them in excess amount, and using a catalytically effective amount to excess amount of the acid. It may be carried out under cooling to heating in a reaction inert solvent such as aromatic hydrocarbons, halogenated hydrocarbons, ethers, DMF, DMSO, ethyl acetate, acetonitrile or the like, or in a mixed liquid thereof.

(Fourth Production Method A)

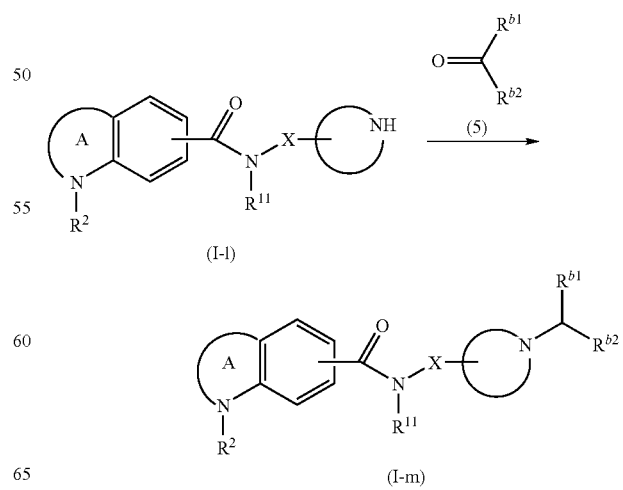

(In the formulae, X represents bond or lower alkylene, $R^{b1}$ and $R^{b2}$ represent —H, aryl, or lower alkyl which may be substituted with —$OR^0$, —$N(R^0)_2$, cycloalkyl, aryl, —O-aryl or heterocyclic group, and

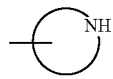

represents nitrogen-containing hetero ring. The same shall apply hereinafter.)

Among the compound (I) of the present invention, a compound represented by the general formula (I-m) may be produced by subjecting a compound of the present invention represented by the general formula (I-l) and a compound represented by the general formula (5) to a reductive amination reaction.

In the reaction, dehydration condensation is firstly carried out by using the compound (I-l) and compound (5) in equivalent amount or one of them in excess amount, and stirring them under cooling to heating in a reaction inert solvent such as aromatic hydrocarbons, halogenated hydrocarbons, ethers, ethyl acetate, acetonitrile or the like, or in a mixed liquid thereof. Next, a reduction reaction is carried out by adding a reducing agent (e.g., sodium cyano borohydride, sodium triacetoxy borohydride, sodium borohydride, formic acid or the like) to the reaction system and stirring under cooling to heating. It is sometimes advantageous for smoothly carrying out the reaction to undergo the reaction in the presence of an acid (e.g., a Lewis acid such as titanium tetraisopropoxide or the like, acetic acid, p-toluenesulfonic acid or the like). Regarding the above-mentioned reduction, it is also carried out by effecting catalytic hydrogen reduction in the aforementioned reaction inert solvent under an atmosphere of hydrogen or in the presence of a hydrogen donor (e.g., ammonium formate or the like), using a metal catalyst such as palladium (Pd), platinum (Pt) or the like.

Regarding the time of adding the reducing agent, it may be charged just after mixing of the compound (I-l) and compound (5) or may be charged at an interval.

Regarding the above reductive amination reaction, for example, this is described in detail in "Jikken Kagaku Koza (Maruzen)" edited by The Chemical Society of Japan (4$^{th}$ edition, vol. 20, 1992, p. 300), so that it may be carried out with reference to this.

(Fourth Production Method B)

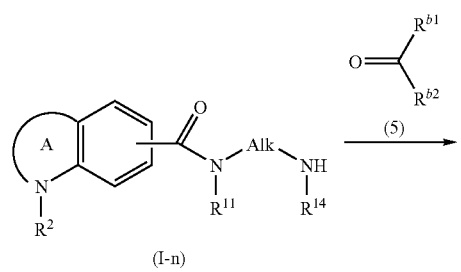

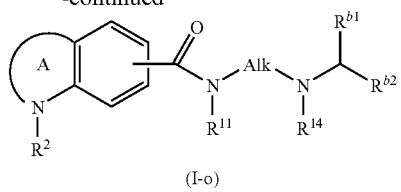

Among the compound (I) of the present invention, a compound represented by the general formula (I-o) may be produced by subjecting a compound represented by the general formula (I-n) and a compound represented by the general formula (5) to a reductive amination reaction.

The reaction may be carried out in the same manner as in the fourth production method A.

(Fifth Production Method Other Production Methods)

The compounds of the present invention having various functional groups such as amino group, carboxyl group, amido group, hydroxyl group, alkylamino group, alkoxy and the like may be easily synthesized making use of the methods which are obvious to those skilled in the art or modified methods thereof, using the compounds of the present invention having corresponding nitro group, ester group, carboxyl group, amino group, hydroxyl group and the like as the starting materials. For example, these may be produced by the following reactions.

5-a: Reduction (1)

A compound having amino group may be produced by reducing a compound having nitro group. For example, the reaction may be carried out using a hydrogenation reaction which uses palladium-carbon, Raney nickel or the like as the catalyst.

5-b: Reduction (2)

A compound having a hydroxyalkyl group may be produced by reducing a compound having an ester group. For example, the reaction may be carried out using lithium aluminum hydride, sodium borohydride or the like as the reducing agent.

5-c: Hydrolysis

A compound having carboxyl group may be produced by hydrolyzing a compound having an ester group. For example, it may be carried out in accordance with the deprotection reaction described in the aforementioned "Protective Groups in Organic Synthesis".

5-d: Amidation

A compound having amido group may be produced by the amidation of a compound having carboxyl group or amino group. It may be carried out in accordance with the aforementioned first production method.

5-e: N-alkylation

A compound having an alkylamino group may be produced by the alkylation of a compound having amino group. As the alkylation reaction, the reaction may be effected in the usual way using various alkylating agents (e.g., an alkyl halide, an alkyl sulfonate ester and the like). In addition, a compound having an alkylamino group may be produced by the reductive amination of a compound having amino group with a carbonyl compound. As the alkylation of amino group, for example, the method described in "Jikken Kagaku Koza (volume 20) Yuki Gosei 2 (Organic Synthesis 2)" edited by The Chemical Society of Japan (4$^{th}$ edition, Maruzen, 1992, p. 300) or the like may be employed.

5-f: O-alkylation

A compound having an alkoxy group may be produced by alkylating a compound having hydroxyl group. As the alkylation reaction, the reaction may be effected in the usual way using various alkylating agents (e.g., an alkyl halide, an alkyl sulfonate ester and the like). For example, it may be carried out by the methods described in the aforementioned third production method A and third production method B, and the method described in "Jikken Kagaku Koza (Maruzen)" edited by The Chemical Society of Japan (4$^{th}$ edition, vol. 20, 1992, p. 187) or the like.

[Production of Starting Compounds]

(Starting Material Synthesis 1)

The starting compounds to be used in the production of the compound (I) of the present invention may be produced for example using the following methods, known methods or modified methods thereof.

(Starting Material Synthesis 1)

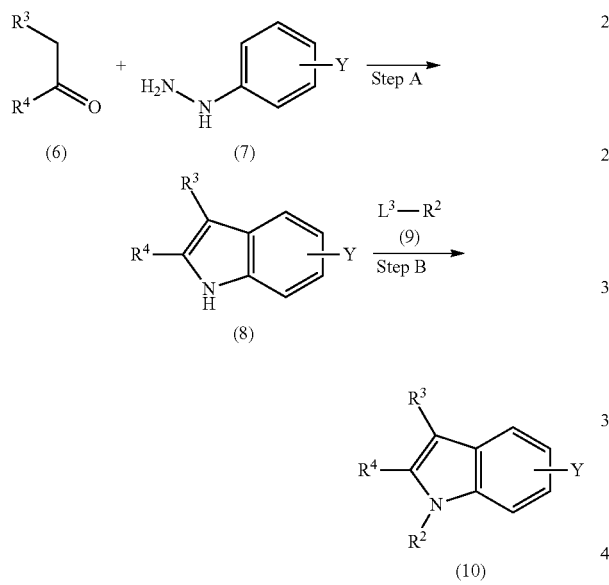

(In the formulae, L$^3$ represents —OH or a leaving group such as halogen, —O-methanesulfonyl, —O-p-toluenesulfonyl or the like, and Y represents a group which may be converted into —CO$_2$H (e.g., —CO$_2$R$^P$, ≡CN or the like), and R$^P$ represents a protecting group such as lower alkyl, benzyl or the like. The same shall apply hereinafter.)

The indole ring forming reaction of step A may be carried out, for example, by the method described in Chem. Rev., 63, 373-401 (1963) or the like. In addition, in carrying out the indole ring forming reaction, the indole ring forming reaction and esterification reaction can also be carried out simultaneously, by using alcohols as the solvent and, as the starting material, a compound in which Y of the compound (7) is —CO$_2$H. The N-alkylation reaction or N-arylation reaction of step B may be carried out, for example, by the method described in "Jikken Kagaku Koza (Maruzen)" edited by The Chemical Society of Japan (4$^{th}$ edition, vol. 20, 1992, p. 284) or the like. In addition, when L$^3$ is —OH in the N-alkylation reaction, it may be carried out using —(cyanomethylene)tributylphospholan or (cyanomethylene)trimethylphospholan under cooling to heating in a reaction inert solvent such as aromatic hydrocarbons, ethers or the like or in a mixed liquid thereof.

(Starting Material Synthesis 2)

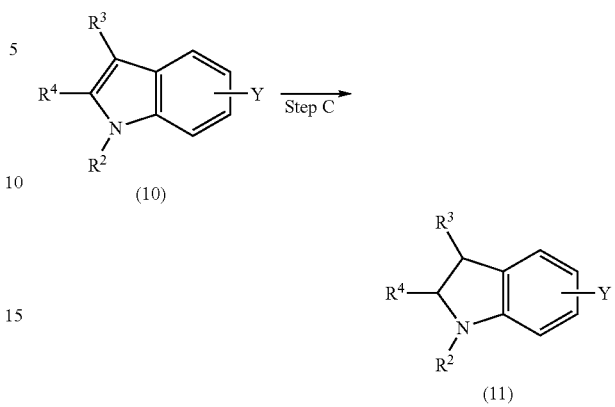

The indol ring reducing reaction of step C may be carried out, for example, by the method described in "Jikken Kagaku Koza (Maruzen)" edited by The Chemical Society of Japan (4$^{th}$ edition, vol. 26, 1992, p. 197) or the like.

(Starting Material Synthesis 3)

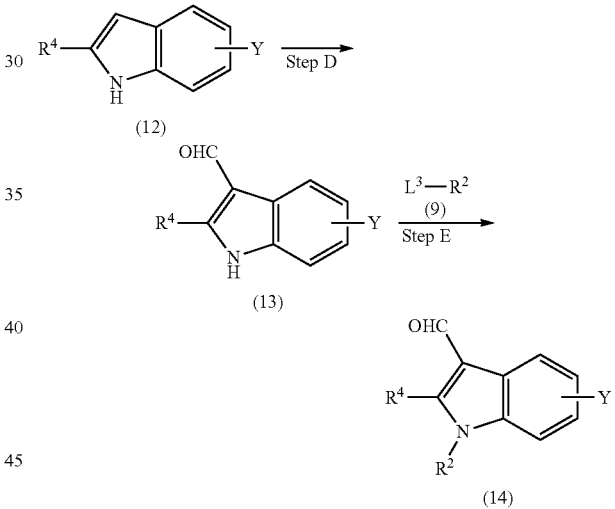

The formylation reaction of step D may be carried out, for example, by the method described in "Jikken Kagaku Koza (Maruzen)" edited by The Chemical Society of Japan (4$^{th}$ edition, vol. 21, 1991, p. 106) or the like. The N-alkylation or N-arylation reaction of step E may be carried out in accordance with the method of the starting material synthesis first step B.

(Starting Material Synthesis 4)

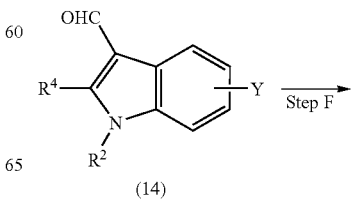

-continued

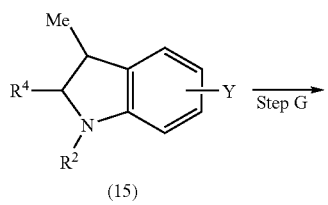

(15)

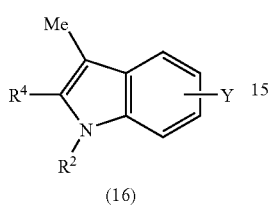

(16)

The reduction of indole ring and aldehyde of step F may be carried out in accordance with the starting material synthesis 2. The oxidation reaction of step G may be carried out, for example, by the method described in "Jikken Kagaku Koza (Maruzen)" edited by The Chemical Society of Japan ($4^{th}$ edition, vol. 23, 1991, p. 346) or the like.

(Starting Material Synthesis 5)

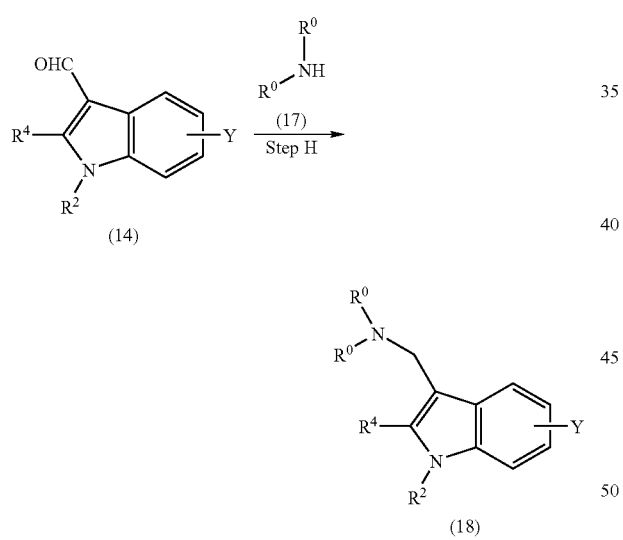

The reductive amination reaction of step H may be carried out in accordance with the fourth production method A.

(Starting Material Synthesis 6)

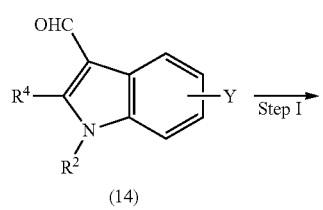

-continued

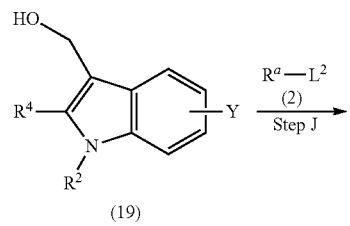

(19)

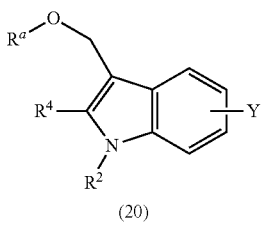

(20)

The aldehyde reducing reaction of step I may be carried out, for example, by the method described in "Jikken Kagaku Koza (Maruzen)" edited by The Chemical Society of Japan ($4^{th}$ edition, vol. 20, 1992, p. 1) or the like. The O-alkylation reaction of step J may be carried out, for example, by the method described in "Jikken Kagaku Koza (Maruzen)" edited by The Chemical Society of Japan ($4^{th}$ edition, vol. 20, 1992, p. 187) or the like.

(Starting Material Synthesis 7)

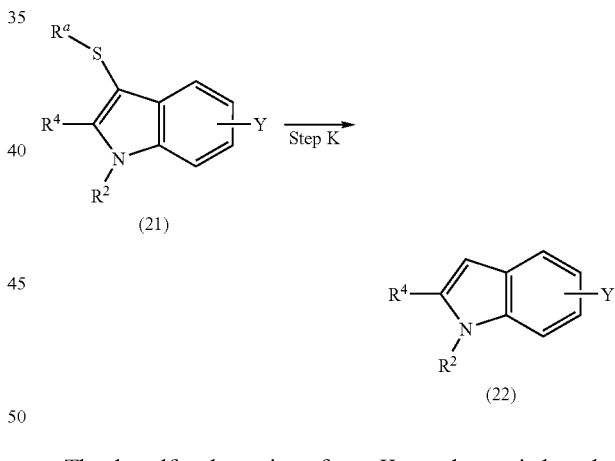

The de-sulfenyl reaction of step K may be carried out by the method described in J. Am. Chem. Soc., 95, 590-592 (1973), J. Org. Chem., 59 (21), 6372-6377 (1994) or the like.

(Starting Material Synthesis 8)

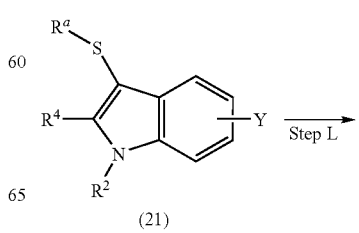

-continued

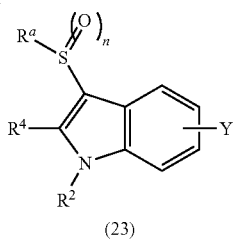

(23)

(In the formulae, n is 1 or 2. The same shall apply hereinafter.)

The sulfide oxidation reaction of step L may be carried out, for example, by the method described in "Jikken Kagaku Koza (Maruzen)" edited by The Chemical Society of Japan ($4^{th}$ edition, vol. 23, 1991, p. 276), "Jikken Kagaku Koza (Maruzen)" edited by The Chemical Society of Japan ($4^{th}$ edition, vol. 24, 1992, p. 350) or the like.

(Starting Material Synthesis 9)

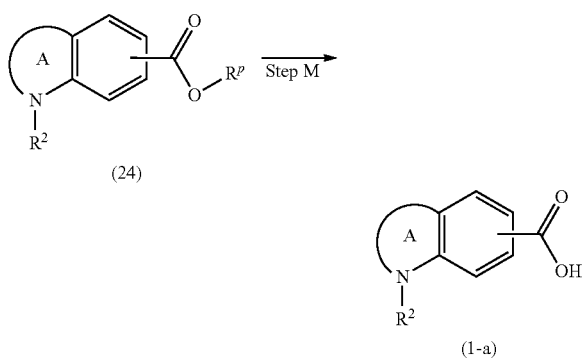

The deprotection reaction of step M may be carried out, for example, in accordance with the aforementioned method described in "Protective Groups in Organic Synthesis".

(Starting Material Synthesis 10)

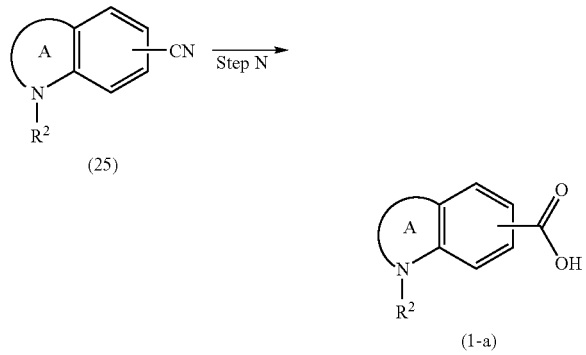

The cyano group hydrolyzing reaction of step N may be carried out using a cyano group hydrolyzing reaction generally used by those skilled in the art. For example, it may be hydrolyzed using sodium hydroxide, potassium hydroxide or the like, in a solvent such as an alcohol, water or the like.

The compound (I) produced in this manner may be isolated and purified as a free compound, a salt thereof or various solvates (e.g., hydrates or the like). Salts may be producing by subjecting to a general salt formation treatment. The isolation and purification are carried out by employing general chemical operations such as extraction, concentration, evaporation, crystallization, filtration, recrystallization, various types of chromatography, and the like.

Various types of isomers may be isolated in the usual way making use of the difference in the physicochemical properties between isomers. For example, optical isomers may be respectively separated and purified by technique such as the method in which racemic compounds are introduced into diastereomer salts with an optically active organic acid (e.g., tartaric acid or the like) and then subjected to fractional recrystallization, or by a chiral filler-aided column chromatography or the like. In addition, an optically active compound can also be produced using an appropriate optically active compound as the starting material. In this connection, a diastereomer mixture can also be separated by a fractional crystallization, chromatography or the like.

The pharmaceutical preparation which comprises one or two or more species of the compound of the present invention or a salt thereof as the active ingredient is prepared using carriers, fillers and other additive agents, which are generally used in preparing medicines.

The administration may be either oral administration by tablets, pills, capsules, granules, powders, solutions and the like, or parenteral administration by injections (e.g., intravenous, intramuscular and the like), suppositories, percutaneous preparations, transnasal preparations, inhalations and the like. The dose is optionally decided in response to each case by taking symptoms and age, sex and the like of the object to be administered into consideration, but is generally approximately from 0.001 mg/kg to 100 mg/kg per day per adult in the case of oral administration, and this is administered once or by dividing into 2 to 4 doses. Also, in the case of intravenous administration, it is administered generally once to >2 or more times a day within a range of from 0.0001 mg/kg to 10 mg/kg per once per adult. Also, in the case of transnasal administration, it is administered generally once to 2 or more times a day within a range of from 0.0001 mg/kg to 10 mg/kg per once per adult. In addition, in the case of inhalation, it is administered generally once to 2 or more times a day within a range of from 0.0001 mg/kg to 1 mg/kg per once per adult.

As the solid composition for oral administration by the present invention, tablets, powders, granules and the like are used. In such a solid composition, one or two more active substances are mixed with at least one inert filler such as lactose, mannitol, glucose, hydroxypropylcellulose, microcrystalline cellulose, starch, polyvinyl pyrrolidone, aluminum magnesium silicate or the like. In accordance with the usual way, the composition may contain inert additive agents lubricants (e.g., magnesium stearate and the like), disintegrators (e.g., carboxymethylstarch sodium and the like), and solubilizing agents. As occasion demands, the tablets or pills may be coated with a sugar coating or a gastric or enteric coating.

As the liquid composition for oral administration, pharmaceutically acceptable emulsions, solutions, suspensions, syrups, elixirs and the like are included, which contain a generally used inert solvent such as purified water or ethanol. In addition to the inert solvent, this composition may contain auxiliary agents (e.g., solubilizing agents, moistening agents, suspending agents and the like), sweeteners, correctives, aromatics and antiseptics.

As the injections for parenteral administration, sterile aqueous or non-aqueous solutions, suspensions and emulsions are included. As the aqueous solvent, for example, distilled water for injection and physiological saline are included. Examples of the non-aqueous solvent include propylene glycol, polyethylene glycol, plant oils (e.g., olive oil or the like), alcohols (e.g., ethanol or the like), polysorbate 80

(name in Pharmacopeia) and the like. Such a composition may further contain tonicity agents, antiseptics, moistening agents, emulsifying agents, dispersing agents, stabilizing agents and solubilizing agents. These are sterilized by, for example, filtration through a bacteria retaining filter, formulation of bactericides or irradiation. In addition, these can also be used by producing a sterile solid composition and dissolving or suspending it in sterile water or a sterile solvent for injection prior to use.

Transmucosal preparations such as inhalations, transnasal preparations and the like are used in a solid, liquid or semisolid form and may be produced in accordance with known methods. For example, excipients (e.g., lactose, starch or the like), as well as a pH adjusting agent, an antiseptic, a surfactant, a lubricant, a stabilizer, a thickener and the like, may be optionally added. An appropriate device for inhalation or blowing may be used for the administration. For example, using a known device such as an inhalation device with measured administration or the like or a sprayer, a compound may be administered alone or as a powder of a formulated mixture, or as a solution or suspension by a combination with a medicinally acceptable carrier. The dry powder inhaler or the like may be for single or multiple administration use, and a dry powder or a powder-containing capsule may be used. Alternatively, it may be in a form such as pressurized aerosol spray or the like which uses a suitable gas such as chlorofluproalkane, hydrofluoroalkane or carbon dioxide or the like.

(Test Methods)

Effects of the compound (I) of the present invention were verified by the following pharmacological tests.

Test Method (1) 5-$HT_{2B}$ Receptor Binding Test (i) Preparation of Membrane Sample Cultured human 5-$HT_{2B}$ receptor expressing HEK293-EBNA cells were washed with a phosphate buffer (PBS)(−). The cells were peeled off with a scraper in the presence of PBS(−), and the cells were recovered by centrifugation (1,000 rpm, 10 minutes, 4° C.). In the presence of 5 mM tris-hydrochloric acid (Tris-HCl) (pH 7.4) buffer, homogenized using a homogenizer (registered trademark: Polytron (PTA 10-TS)), and centrifugation-treated (40,000×g, 10 minutes, 4° C.). In the presence of 50 mM Tris-HCl (pH 7.4) buffer, suspended using Glass-Teflon (registered trademark) homogenizer. By carrying out centrifugation treatment (40,000×g, 10 minutes, 4° C.), suspended in 50 mM Tris-HCl (pH 7.4) and stored at −80° C.

(ii) Receptor Binding Test

A total volume of 500 µl containing 50 mM Tris-HCl, a 4 mM $CaCl_2$ (pH 7.4) buffer, a human 5-$HT_{2B}$ receptor expressing HEK293-EBNA cell membrane preparation and a radio-ligand [$^3$H] Mesulergine (3.1 TBq/mmol;) or [$^3$H] Serotonin (5-Hydroxytryptamine) (3.7 TBq/mmol;) was incubated at 25° C. for 1 hour. The compound was dissolved in 100% dimethyl sulfoxide (DMSO) and diluted to respective concentrations. Binding quantity in the presence of 1 µM ritanserin was regarded as the nonspecific binding, and a result of subtracting the nonspecific binding quantity from the total binding quantity was regarded as the specific binding quantity. After adding 4 ml of 50 mM Tris-HCl buffer (pH 7.4) and filtering under a reduced pressure using a GF/B glass filter, the filter was washed (4 ml×3) with the same buffer. By soaking the glass filter in 5 ml of a liquid scintillator (trade name: Aquasol-2), the radioactivity quantity was measured using a liquid scintillation counter. The concentration of compound which inhibits 50% of the receptor binding, $IC_{50}$ value, was calculated by nonlinear regression analysis using a statistical analysis software (registered trademark: SAS (ver. 6.11)), and the Ki value which shows affinity for the receptor was calculated using the formula of Cheng & Prussoff; Ki=$IC_{50}$/(1+[L]/[Kd]) ([L]: ligand concentration, [Kd]: dissociation constant). The results are shown in the following Table 1. Ex represents the Example compound number which is described later.

TABLE 1

| Ex | Ki (nM) |
|---|---|
| 10 | 2.7 |
| 24 | 0.24 |
| 102 | 0.12 |
| 103 | 0.12 |
| 104 | 0.088 |
| 156 | 3.4 |
| 226 | 0.19 |
| 236 | 0.29 |
| 237 | 0.22 |
| 238 | 0.24 |

Test Method (2) 5-$HT_7$ Receptor Binding Test (i) Preparation of Membrane Sample Cultured human 5-$HT_7$ receptor expressing CHO cells were washed with PBS(−). The cells were peeled off with a scraper in the presence of PBS(−), and the cells were recovered by centrifugation (1,000 rpm, 10 minutes, 4° C.). In the presence of 5 mM Tris-HCl (pH 7.4) buffer, homogenized using a homogenizer (registered trademark: Polytron (PTA 10-TS)), and centrifugation-treated (40,000×g, 10 minutes, 4° C.). In the presence of 50 mM Tris-HCl (pH 7.4) buffer, suspended using Glass-Teflon (registered trademark) homogenizer. By carrying out centrifugation treatment (40,000×g, 10 minutes, 4° C.), suspended in 50 mM Tris-HCl (pH 7.4) and stored at −80° C.

(ii) Receptor Binding Test

A total volume of 500 µl containing 50 mM Tris-HCl, a 4 mM $CaCl_2$ (pH 7.4) buffer, a human 5-$HT_7$ receptor expressing CHO cell membrane preparation and a radio-ligand [$^3$H] 5-HT (3.40 TBq/mmol) was incubated at 25° C. for 1 hour. The compound was dissolved in 100% DMSO and diluted to respective concentrations.

Binding quantity in the presence of 10 µM metergoline was regarded as the nonspecific binding, and a result of subtracting the nonspecific binding quantity from the total binding quantity was regarded as the specific binding quantity. After adding 4 ml of 50 mM Tris-HCl buffer (pH 7.4) and filtering under a reduced pressure using a GF/B glass filter, the filter was washed (4 ml×3) with the same buffer. By soaking the glass filter in 5 ml of a liquid scintillator (trade name: Aquasol-2), the radioactivity quantity was measured using a liquid scintillation counter. The concentration of compound which inhibits 50% of the receptor binding, $IC_{50}$ value, was calculated by nonlinear regression analysis using SAS (ver. 6.11)), and the Ki value which shows affinity for the receptor was calculated using the formula of Cheng & Prussoff; Ki=$IC_{50}$/(1+[L]/[Kd]) ([L]: ligand concentration, [Kd]: dissociation constant). The results are shown in the following Table 2.

TABLE 2

| Ex | Ki (nM) |
|---|---|
| 10 | 2.8 |
| 24 | 0.66 |
| 102 | 0.36 |
| 103 | 1.3 |
| 104 | 1.3 |
| 156 | 3.4 |
| 226 | 4.3 |

TABLE 2-continued

| Ex | Ki (nM) |
|---|---|
| 236 | 2.6 |
| 237 | 4.9 |
| 238 | 8.0 |

Test Method (3) Affinity for Other Receptors

Affinities for $5\text{-}HT_{1A}$, $5\text{-}HT_{1B}$, $5\text{-}HT_{2A}$, $5\text{-}HT_{2C}$, $5\text{-}HT_3$ $5\text{-}HT_4$, $5\text{-}HT_6$, $\alpha_1$, $M_1$ and $D_2$ receptors can be verified using a known method ("Journal of Neurochemistry" (England), 1986, vol. 47, p. 529-540; "Molecular Pharmacology", (USA), 1982, vol. 21, p. 301-314; "European Journal of Pharmacology", (Holland), 1985, vol. 106, p. 539-546; "The Journal of Pharmacology Experimental Therapeutics", (USA), 1992, vol. 263, p. 1127-1132; "British Journal of Pharmacology", (England), 1993, vol. 109, p. 618-624; "Molecular Pharmacology", (USA), 1993, vol. 43, p. 320-327; "Molecular Pharmacology", (USA), 1989, vol. 35, p. 324-330; "Cellular and Molecular Neurobiology", (Germany), 1988, vol. 8, p. 181-191; or "European Journal of Pharmacology", (Holland), 1988, vol. 173, p. 177-182).

In this connection, affinities of the RS-127445 (2-amino-4-(4-fluoronaphth-1-yl)-6-isopropylpyrimidine; see WO 97/44326 for its production method) and SB-269970 ((R)-3-(2-(2-(4-methylpiperidin-1-yl)ethyl)pyrrolidine-1-sulfonyl)phenol; see International Publication No. 97/48681 for its production method) described in the following test method (4) for respective receptors are known, and regarding the RS-127445, it has been reported for example in "British Journal of Pharmacology", (England), 1999, vol. 127, p. 1075-1082, that said compound has a pKi value of 9.5 for $5\text{-}HT_{2B}$ receptor and is $5\text{-}HT_{2B}$ receptor-selective by a factor of 1000 times or more for the receptors such as $5\text{-}HT_{1A}$, $5\text{-}HT_{1B}$, $5\text{-}HT_{2A}$, $5\text{-}HT_{2C}$, $5\text{-}HT_3$, $5\text{-}HT_6$, $5\text{-}HT_7$, $\alpha_1$, $M_1$, $D_2$ and the like. Also, regarding the SB-269970, it has been reported for example in "Journal of Medicinal Chemistry", (USA), 2000, vol. 43, p. 342-345, that said compound has a pKi value of 8.9 for $5\text{-}HT_{2B}$ receptor and is $5\text{-}HT_7$ receptor-selective by a factor of 250 times or more for the receptors such as $5\text{-}HT_{1A}$, $5\text{-}HT_{1B}$, $5\text{-}HT_{2A}$, $5\text{-}HT_{2B}$, $5\text{-}HT_{2C}$, $5\text{-}HT_4$, $5\text{-}HT_6$, $\alpha_1$, $D_2$ and the like.

Test Method (4) Defecation Suppressing Effect at the Time of Restraint Stress Loading The IBS-treating effect of the compound (I) of the present invention was evaluated using a test method in which the amount of excreted feces is measured by loading a restraint stress on rats (see "The Journal of Pharmacology Experimental Therapeutics", (USA), 1992, vol. 261, p. 297-303). This test is an animal model in which it is known that a $5\text{-}HT_3$ receptor antagonist as a diarrhea type IBS-treating agent shows its efficacy.

Test Method

The agent to be tested was administered to male Wistar rats (body weight 250 to 320 g, 10 animals for each group), and a restraint stress was loaded 30 minutes to 3 hours thereafter. A restraint cage (trade name: KN-468, 265 mm in width×95 mm in length×200 mm in height, Natsume Seisakusho, Tokyo) was used for the restraint stress loading, and the number of feces excreted during 1 hour after the stress loading was counted.

As shown in FIG. 1, the RS-127445 as a $5\text{-}HT_{2B}$-selective antagonistic compound did not show defecation-suppressing action even when a dose of 10 mg/kg was orally administered (p.o.) (the restraint stress was loaded 30 minutes after the administration).

Figure 2:
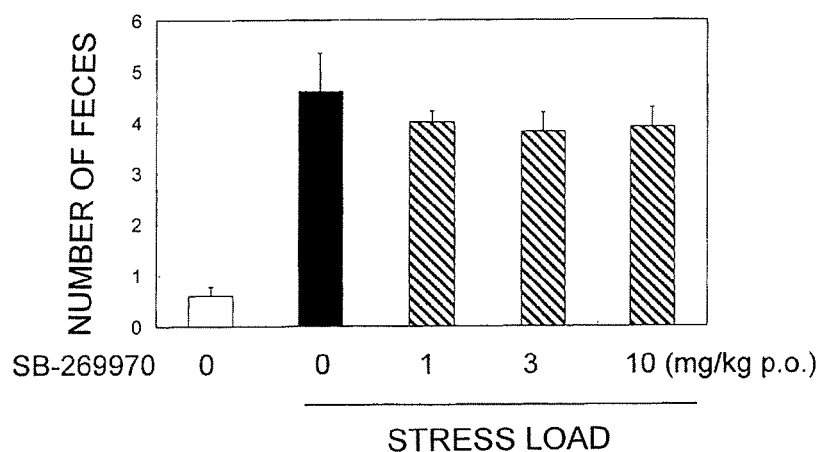
FIG. 2 is a graph showing a result of the measurement of the number of feces excreted at the time of SB-269970 administration, in the rat restraint stress defecation model of the test method (4). Significant difference was not found in the 1, 3 or 10 mg/kg administration group in comparison with the non-administration group (N=10).

In addition, as shown in FIG. 2, the SB-269970 as a $5\text{-}HT_7$-selective antagonistic compound also did not show the defecation-suppressing action even at a dose of 10 mg/kg (p.o.) (the restraint stress was loaded 30 minutes after the administration).

Figure 3:
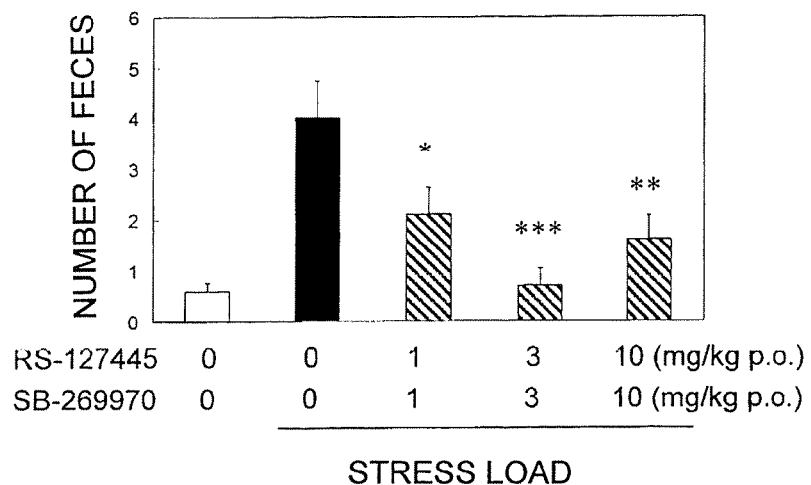
FIG. 3 is a graph showing a result of the measurement of the number of feces excreted at the time of the simultaneous administration of RS-127445 and SB-269970, in the rat restraint stress defecation model of the test method (4). The statistical test was carried out by the Dunnett's method, and * shows a level of significance of 5%, and  that of 1% and * that of 0.1% (N=10).

On the other hand, as shown in FIG. 3, it was found that a synergistic effect can be obtained when both of the compounds RS-127445 and SB-269970 are simultaneously administered. That is, as shown in FIG. 1 and FIG. 2, each of the RS-127445 and SB-269970 alone did not show the action even at 10 mg/kg (p.o.), but when both compounds were simultaneously administered, it was revealed that they show a significant suppressive action starting from a dose of 1 mg/kg (p.o.) (the restraint stress was loaded 30 minutes after the administration).

Based on the above results, it is expected that when the compound of the present invention possesses the $5\text{-}HT_{2B}$ receptor antagonism together with the $5\text{-}HT_7$ receptor antagonism, it will show a superior IBS morbid state-improving effect in comparison with the selective receptor antagonists against one of the receptors.

This effect was the same when a compound of the present invention having both of the $5\text{-}HT_{2B}$ receptor antagonism and $5\text{-}HT_7$ receptor antagonism was used.

Figure 4:
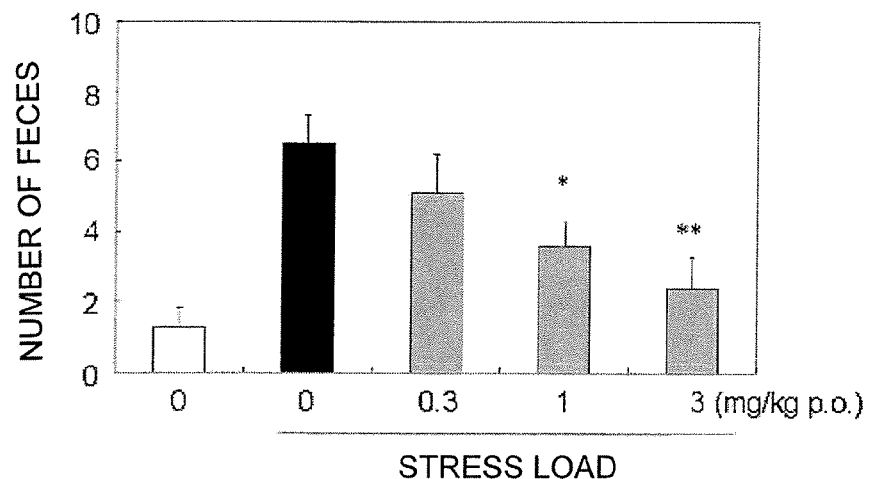
FIG. 4 is a graph showing a result of the measurement of the number of feces excreted at the time of the administration of the Example compound 226, in the rat restraint stress defecation model of the test method (4). The statistical test was carried out by the Dunnett's method, and * shows a level of significance of 5%, and ** that of 1% (N=10).

As shown in FIG. 4, when the Example compound 226 was administered, it showed a significant suppressing action starting from a dose of 1 mg/kg (p.o.) (the restraint stress was loaded 1 hour after the administration).

Figure 5:
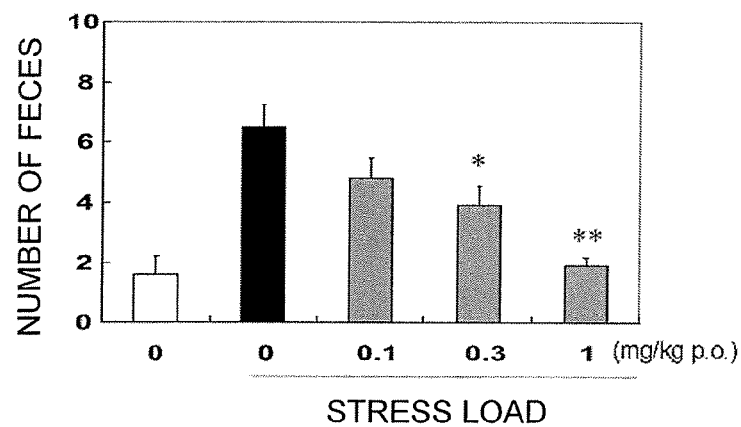
FIG. 5 is a graph showing a result of the measurement of the number of feces excreted at the time of the administration of the Example compound 236, in the rat restraint stress defecation model of the test method (4). The statistical test was carried out by the Dunnett's method, and * shows a level of significance of 5%, and ** that of 1% (N=10).

As shown in FIG. 5, when the Example compound 236 was administered, it showed a significant suppressing action starting from a dose of 0.3 mg/kg (p.o.) (the restraint stress was loaded 3 hours after the administration).

Figure 6:
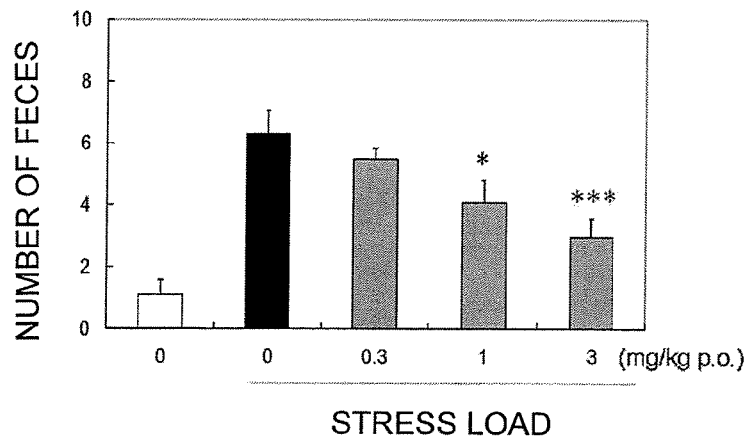
FIG. 6 is a graph showing a result of the measurement of the number of feces excreted at the time of the administration of the Example compound 103, in the rat restraint stress defecation model of the test method (4). The statistical test was carried out by the Dunnett's method, and * shows a level of significance of 5%, and *** that of 0.1% (N=10).

As shown in FIG. 6, when the Example compound 103 was administered, it showed a significant suppressing action starting from a dose of 1 mg/kg (p.o.) (the restraint stress was loaded 1 hour after the administration).

Figure 7:
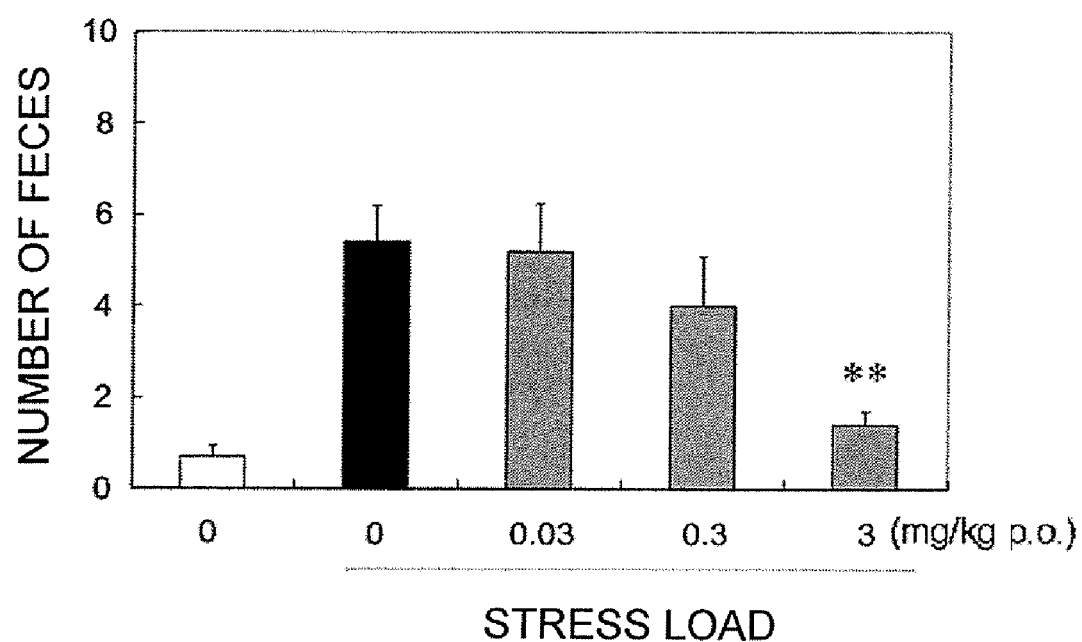
FIG. 7 is a graph showing a result of the measurement of the number of feces excreted at the time of the administration of the Example compound 244, in the rat restraint stress defecation model of the test method (4). The statistical test was carried out by the Dunnett's method, and ** shows a level of significance of 1% (N=10).

As shown in FIG. 7, when the Example compound 244 was administered, it showed a significant suppressing action starting from a dose of 3 mg/kg (p.o.) (the restraint stress was loaded 1 hour after the administration).

As a result of the aforementioned each test, it was confirmed that the compounds of the present invention are possessed of the $5\text{-}HT_{2B}$ receptor antagonism and $5\text{-}HT_7$ receptor antagonism. Based on this, it is evident that they are useful as an agent for treating IBS and a preventive agent for migraine.

EXAMPLES

The following illustratively describes production methods of the compounds of the present invention with reference to the production examples of the compounds of the present invention, but the present invention is not restricted by these examples. In this connection, since novel compounds are included in the starting compounds of the compounds of the present invention, production methods of these compounds are described as production examples.

In this connection, symbols in the production examples and Examples and in the tables which are described later represent the following meanings (the same shall apply hereinafter).

REx: production example number, Ex: Example number, Str: structural formula, Dat: physical data (FAB: FAB-MS (POS) (M$^+$+1 unless otherwise noted), ESI: ESI-MS (POS) (M$^+$+1 unless otherwise noted); NMR: δ(ppm) of characteristic peak in $^1$H-NMR), Sal: salt (a blank space or no description indicates that it is a free form, and the numeral before the acid component indicates molar ratio; for example, 2HCl is described, it shows that the compound is dihydrochloride), Me: methyl, Et: ethyl, nPr: normal propyl, iPr: isopropyl, iBu: isobutyl, tBu: tert-butyl, iPen: isopentyl, cPen: cyclopentyl, cHex: cyclohexyl, Ph: phenyl, Bn: benzyl, null: no substitution; the numeral before the substituent group indicates its substitution position, and for example, 5-F means 5-fluoro; and RSyn and Syn: production method (the numeral indicates that it was produced using the corresponding starting material similar to the case of compounds respectively having the numerals as the production example numbers or Example numbers, and when two or more numerals are described, it means that it was produced using successive corresponding production methods).

Production Example 1

A 5.00 g portion of 4-hydrazinobenzoic acid was suspended in 50 ml of ethanol, and 5.6 ml of 3-pentanone and 2.7 ml of sulfuric acid were added, followed by stirring at 85° C. for 24 hours. After evaporation of ethanol under a reduced pressure, water was added to the residue under ice-cooling, followed by stirring at the same temperature for 30 minutes. The resulting solid was collected by filtration and then washed with water to obtain 6.34 g of ethyl 2-ethyl-3-methyl-1H-indole-5-carboxylate as a light brown solid.

Production Example 2

A 500 mg portion of ethyl 2-ethyl-3-methyl-1H-indole-5-carboxylate was dissolved in 10 ml of N,N-dimethylformamide, and 113 mg of sodium hydride (55% dispersion in oil) was added under ice-cooling, followed by stirring at room temperature for 30 minutes. Then, 490 mg of 1-(bromomethyl)-4-fluorobenzene was added under ice-cooling, followed by stirring at room temperature for 2 hours. After evaporation of the solvent under a reduced pressure, the residue was diluted with ethyl acetate and washed with water and saturated brine. After drying the organic layer with anhydrous sodium sulfate, the solvent was evaporated under a reduced pressure, and the residue was purified by silica gel column chromatography (ethyl acetate:hexane=1:20 to 1:0) to obtain 587 mg of ethyl 2-ethyl-1-(4-fluorobenzyl)-3-methyl-1H-indole-5-carboxylate as a pale brown oily material.

Production Example 3

A 587 mg portion of ethyl 2-ethyl-1-(4-fluorobenzyl)-3-methyl-1H-indole-5-carboxylate was dissolved in 10.5 ml of ethanol, and 3.5 ml of a 1 M sodium hydroxide aqueous solution was added, followed by overnight stirring at 80° C. Under ice-cooling, 1 M hydrochloric acid and water were added thereto, followed by stirring at pH 1 for 1 hour. Then, the resulting solid was collected by filtration to obtain 498 mg of 2-ethyl-1-(4-fluorobenzyl)-3-methyl-1H-indole-5-carboxylic acid as a pale pink solid.

Production Example 4

A 500 mg portion of ethyl 2,3-dimethyl-1H-indole-5-carboxylate was dissolved in 24 ml of toluene, and 0.39 ml of 3-thienylmethanol and 1.00 g of cynomethylene tri-N-butylphospholan were added at room temperature, followed by overnight stirring at 110° C. A 0.39 ml portion of 3-thienylmethanol and 1.00 g of cyanomethylene tri-N-butylphospholan were added to the reaction liquid, followed by stirring at 110° C. for 8 hours. After evaporation of the solvent under a reduced pressure, the residue was purified by silica gel column chromatography (ethyl acetate:hexane=1:20 to 1:10) to obtain 378 mg of ethyl 2,3-dimethyl-1-(3-thienylmethyl)-1H-indole-5-carboxylate as a yellow solid.

Production Example 5

A 211 mg portion of ethyl 2,3-dimethyl-1H-indole-5-carboxylate was dissolved in 10 ml of toluene, and 0.232 ml of 2-phenylethanol and 224 mg of cyanomethylene trimethylphospholan were added at room temperature, followed by stirring at 100° C. for 17 hours. After evaporation of the solvent under a reduced pressure, the residue was purified by silica gel column chromatography (ethyl acetate:hexane=1:49 to 1:9) to obtain 107 mg of ethyl 2,3-dimethyl-1-(2-phenylethyl)-1H-indole-5-carboxylate as a colorless oily material.

Production Example 6

A 460 mg portion of ethyl 1-benzyl-2,3-dimethyl-1H-indole-5-carboxylate was dissolved in 15 ml of trifluoroacetic acid, and 1.19 ml of triethylsilane was added at room temperature, followed by stirring at 50° C. for 3 hours. After evaporation of the solvent, ethyl acetate was added, followed by washing with a 1 M sodium hydroxide aqueous solution and saturated brine and subsequent drying over anhydrous sodium sulfate. After evaporation of the solvent, the residue was purified by silica gel column chromatography (ethyl acetate:hexane=1:30 to 1:20) to obtain 437 mg of ethyl 1-benzyl-2,3-dimethylindoline-5-carboxylate as a pale yellow liquid.

Production Example 7

A 1.28 ml portion of phosphoryl chloride was added dropwise to 8 ml of N,N-dimethylformamide under ice-cooling, followed by stirring at room temperature for 15 minutes. An 8 ml portion of an N,N-dimethylformamide solution of 2.00 g of methyl 1H-indole-5-carboxylate was added dropwise to this solution under ice-cooling, followed by stirring at room temperature for 1.5 hours. Under ice-cooling, 50 ml of water was added thereto and potassium carbonate was further added until the pH became 12, and the resulting solid was collected by filtration, washed with water and then dried over heating under a reduced pressure to obtain 2.19 g of methyl 3-formyl-1H-indole-5-carboxylate as a pale light brown solid.

Production Example 8

A 234 mg portion of ethyl 2,3-dimethyl-1H-indole-5-carboxylate was dissolved in 1 ml of toluene, and 0.145 ml of iodobenzene and 10 mg of copper(I) iodide and 480 mg of tripotassium phosphate and 26 ml of trans-1,2-cyclohexanediamine were added at room temperature, followed by stirring at 100° C. for 24 hours. After evaporation of the solvent under a reduced pressure, the residue was purified by silica gel column chromatography (hexane-ethyl acetate:hexane=1:4) to obtain 79 mg of ethyl 2,3-dimethyl-1-phenyl-1H-indole-5-carboxylate as a colorless oily material.

Production Example 9

A 350 mg portion of methyl 3-formyl-1H-indole-5-carboxylate was suspended in 10 ml of methanol, and 90 mg of sodium borohydride was added at 0° C., followed by stirring at room temperature for 30 minutes. After evaporation of the solvent, ethyl acetate and water were added thereto, and the ethyl acetate layer was washed with water and saturated brine and then dried over anhydrous sodium sulfate. By evaporating the solvent under a reduced pressure, 337 mg of methyl 3-(hydroxymethyl)-1H-indole-5-carboxylate was obtained as a colorless solid.

Production Example 10

A 327 mg portion of methyl 3-(hydroxymethyl)-1H-indole-5-carboxylate was dissolved in 9 ml of acetonitrile, mixed with 385 mg of silver oxide and 3.6 ml of methyl iodide and stirred at 80° C. for 5 hours. A 385 mg portion of silver oxide was further added thereto and stirred overnight at 80° C. A 385 mg portion of silver oxide and 3.6 ml of methyl iodide were further added thereto and stirred at 80° C. for 9 hours. After cooling to room temperature, the insoluble matter was removed, the solvent was evaporated, and then the residue was purified by silica gel column chromatography (ethyl acetate:hexane=1:6 to 1:5 to 1:4) to obtain 143 mg of methyl 3-(methoxymethyl)-1H-indole-5-carboxylate as a pale yellow solid.

Production Example 11

A 500 mg portion of methyl 1-benzyl-3-formyl-1H-indole-5-carboxylate was dissolved in 17 ml of trifluoroacetic acid, and 2.70 ml of triethylsilane was added at 0° C., followed by stirring at room temperature for 3 hours. After evaporation of the solvent, ethyl acetate was added thereto, followed by washing with water, a saturated sodium bicarbonate aqueous solution and saturated brine and subsequent drying over anhydrous sodium sulfate. After evaporation of the solvent, the residue was purified by silica gel column chromatography (ethyl acetate:hexane=1:30 to 1:20) to obtain 433 mg of methyl 1-benzyl-3-methylindoline-5-carboxylate as a pale yellow liquid.

Production Example 12

This was carried out in accordance with the method described in J. Org. Chem., 61, 2594 (1996).

A 269 mg portion of methyl 1-benzyl-3-methylindoline-5-carboxylate was dissolved in 10 ml of tert-butyl methyl ether, and 235 mg of o-chloranil was added, followed by stirring at room temperature for 1 hour. After dilution with ethyl acetate and subsequent washing with a 1 M sodium hydroxide aqueous solution, it was dried over anhydrous sodium sulfate. After evaporation of the solvent, the residue was purified by silica gel column chromatography (ethyl acetate:hexane=1:30 to 1:20 to 1:10) to obtain 433 mg of methyl 1-benzyl-3-methyl-1H-indole-5-carboxylate as a colorless solid.

Production Example 13

A 500 mg portion of ethyl 1-benzyl-2-methyl-3-(methylthio)-1H-indole-5-carboxylate was added to 15 ml of a Raney nickel ethanol solution, followed by stirring at room temperature for 3 hours. The Raney nickel ethanol solution was added until the material disappeared. Raney nickel was removed, the solvent was evaporated and then the residue was purified by silica gel column chromatography (ethyl acetate:hexane=1:10 to 1:7 to 1:5) to obtain 426 mg of ethyl 1-benzyl-2-methyl-1H-indole-5-carboxylate as a colorless solid.

Production Example 14

A 400 mg portion of methyl 3-formyl-1H-indole-5-carboxylate was dissolved in 14 ml of dichloromethane, and 167 mg of dimethylamine hydrochloride, 0.29 ml of triethylamine and 0.16 ml of acetic acid were added in that order, followed by stirring at room temperature for 1 hour. A 1.45 g portion of sodium triacetoxy borohydride was added to this solution at 0° C., followed by overnight stirring at room temperature.

Water was added thereto at 0° C. and the pH was adjusted to 8 by further adding a 1 M sodium hydroxide aqueous solution, followed by the extraction with ethyl acetate, washing with water, a saturated sodium bicarbonate aqueous solution and saturated brine and subsequent drying over anhydrous sodium sulfate. After evaporation of the solvent, the residue was purified by silica gel column chromatography (Clomatorex (registered trademark), ethyl acetate:chloroform=1:30 to 1:20) to obtain 413 mg of methyl 1-benzyl-3-[(dimethylamino)methyl]-1H-indole-5-carboxylate as a pale yellow solid.

Production Example 15

A 300 mg portion of ethyl 1-(4-fluorobenzyl)-2-methyl-3-(methylthio)-1H-indole-5-carboxylate was dissolved in 3 ml of chloroform, and 203 mg of 3-chloroperbenzoic acid was added under ice-cooling, followed by stirring at the same temperature for 1 hour. A saturated sodium bicarbonate aqueous solution was added to the reaction liquid, followed by extraction with ethyl acetate. The organic layer was washed with saturated brine and then dried over anhydrous sodium sulfate. After evaporation of the solvent under a reduced pressure, the residue was purified by silica gel column chromatography (chloroform:methanol:hexane=1:0:1 to 1:0:0 to 100:1:0 to 50:1:0 to 30:1:0) to obtain 279 mg of ethyl 1-(4-fluorobenzyl)-2-methyl-3-(methylsulfinyl)-1H-indole-5-carboxylate as a colorless solid.

Production Example 16

A 300 mg portion of ethyl 1-(4-fluorobenzyl)-2-methyl-3-(methylthio)-1H-indole-5-carboxylate was dissolved in 3 ml of chloroform, and 483 mg of 3-chloroperbenzoic acid under ice-cooling was added, followed by stirring at the same temperature for 30 minutes and then at room temperature for 1 hour. A 10% sodium hydrogen sulfite aqueous solution was added to the reaction liquid, followed by extraction with ethyl acetate. The organic layer was washed with a saturated sodium bicarbonate aqueous solution and saturated brine and then dried over anhydrous sodium sulfate. After evaporation of the solvent under a reduced pressure, the residue was purified by silica gel column chromatography (ethyl acetate:hexane:chloroform=0.2:1:1 to 0.3:1:1 to 0.4:1:1) to obtain 285 mg of ethyl 1-(4-fluorobenzyl)-2-methyl-3-(methylsulfonyl)-1H-indole-5-carboxylate as a pale green solid.

Production Example 17

Under ice-cooling, 1.3 ml of phosphorus oxychloride was added to 7 ml of N,N-dimethylformamide at an inner temperature of from 10 to 20° C., followed by stirring at room temperature for 15 minutes. Under ice-cooling, 9 ml of an N,N-dimethylformamide solution of 2-methyl-1H-indole-5-carbonitrile was added to this solution at an inner temperature of from 10 to 20° C., followed by overnight stirring at room temperature. A 64 ml portion of water was added thereto at 0° C. and the pH was adjusted to 8 with potassium carbonate, followed by 2.5 hours of stirring at room temperature. The thus precipitated solid was collected by filtration, washed with water and then dried at 80° C. under a reduced pressure to obtain 1.73 g of 3-formyl-2-methyl-1H-indole-5-carbonitrile as a pale yellow solid.

Production Example 18

A 500 mg portion of 1-(4-fluorobenzyl)-3-(hydroxymethyl)-2-methyl-1H-indole-5-carbonitrile was suspended in 5 ml of methanol, and 1.3 ml of 4 M hydrogen chloride/1,4-dioxane was added, followed by overnight stirring at room temperature.
A 1.1 ml portion of an 8 M potassium hydroxide aqueous solution was added thereto, and the solvent was evaporated. The residue was dissolved in 32 ml of ethanol, 6.4 ml of an 8 M potassium hydroxide aqueous solution was added, followed by stirring at 100° C. for 24 hours. At 0° C., the pH was adjusted to 2 using 6 M hydrochloric acid and 1 M hydrochloric acid, followed by 1 hour of stirring at 0° C. The thus precipitated solid was collected by filtration, washed with water and then dried at 90° C. under a reduced pressure to obtain 607 mg of 1-(4-fluorobenzyl)-3-(methoxymethyl)-2-methyl-1H-indole-5-carboxylic acid as a pink solid Production Example 19

A 500 mg portion of 2-methyl-1H-indole-5-carbonitrile was dissolved in 5 ml of dichloromethane, and 27.0 ml of 1 M tin tetrachloride (a dichloromethane solution) was added dropwise thereto at 0° C., followed by stirring at 0° C. for 10 minutes. Then, 0.27 ml of acetyl chloride was added thereto at 0° C., followed by overnight stirring at room temperature. A 25 ml portion of a 2 M sodium hydroxide aqueous solution was added thereto at 0° C. to adjust the pH to 12, followed by stirring at 0° C. for 1 hour and extraction with a 20% methanol-chloroform mixed solvent. The organic layer was washed with saturated brine and dried over anhydrous sodium sulfate, and then the solvent was evaporated under a reduced pressure to obtain 607 mg of 3-acetyl-2-methyl-1H-indole-5-carbonitrile as a beige solid.

Production Example 20

A 1.33 g portion of methyl 1-(4-fluorobenzyl)-2-methyl-1H-benzimidazole-5-carboxylate was suspended in 30 ml of ethanol, and 15 ml of a 1 M sodium hydroxide aqueous solution was added, followed by stirring at room temperature for 16 hours.
After evaporation of the solvent under a reduced pressure, 15 ml of 1 M hydrochloric acid was added thereto, followed by stirring at room temperature for 30 minutes. The thus precipitated solid was collected by filtration to obtain 1.139 g of 1-(4-fluorobenzyl)-2-methyl-1H-benzimidazole-5-carboxylic acid as a colorless solid.
In the same manner as the methods of the above-mentioned production examples 1 to 20, the Production Example compounds 21 to 102 shown in Tables 3 to 14 which are described later were produced using respectively corresponding starting materials. Structures and physical data of the Production Example compounds are shown in the Tables 3 to 14 which are described later.

Example 1

A 134 mg portion of 2,3-dimethyl-1-(3-thienylmethyl)-1H-indole-5-carboxylic acid and 152 mg of 1,1'-carbonyldiimidazole were dissolved in 5 ml of N,N-dimethylformamide, followed by stirring at 50° C. for 1 hour. Then, 212 mg of guanidine carbonate was added, followed by stirring at room temperature for 4 days.

After evaporation of the solvent and subsequent addition of water, the thus precipitated solid was purified by silica gel column chromatography (Clomatorex (registered trademark), methanol:chloroform:water=100:1:0.1 to 50:1:0.1 to 30:1:0.1 to 20:1:0.1) to obtain 130 mg of N-(diaminomethylene)-2,3-dimethyl-1-(3-thienylmethyl)-1H-indole-5-carboxamide as a colorless solid. This product was suspended in 1.5 ml of ethanol, 0.15 ml of 4 M hydrogen chloride/ethyl acetate was added, followed by stirring at room temperature for 1 hour. The resulting solid was collected by filtration and then washed with ethanol to obtain 124 mg of N-(diaminomethylene)-2,3-dimethyl-1-(3-thienylmethyl)-1H-indole-5-carboxamide hydrochloride as a light brown solid.

Example 2

A 415 mg portion of 1-benzyl-N-(diaminomethylene)-3-formyl-1H-indole-5-carboxamide was suspended in 15 ml of methanol, 98 mg of sodium borohydride was added at 0° C., followed by stirring at room temperature for 1.5 hours. After evaporation of the solvent and subsequent addition of water, the thus precipitated solid was purified by silica gel column chromatography (Clomatorex (registered trademark), methanol:chloroform:water=50:1:0.1 to 30:1:0.1 to 20:1:0.1 to 10:1:0.1). The thus obtained product was crystallized from methanol/water to obtain 325 mg of 1-benzyl-N-(diaminomethylene)-3-hydroxymethyl-1H-indole-5-carboxamide as a pale pink solid.

Example 3

A 250 mg portion of 2-ethyl-1-(4-fluorobenzyl)-3-methyl-1H-indole-5-carboxylic acid, 231 mg of 1-ethyl-3-(3-dimethylaminopropyl)carbodiimide hydrochloride and 54 mg of 1-hydroxybenzotriazole were dissolved in 8 ml of N,N-dimethylformamide, and then 106 mg of N,N-dimethyl-1,2-ethanediamine was added, followed by overnight stirring at room temperature. The reaction liquid was diluted with chloroform and then washed with a 1 M sodium hydroxide aqueous solution and saturated brine, and dried over anhydrous sodium sulfate. After evaporation of the solvent under a reduced pressure, the residue was purified by silica gel column chromatography (chloroform:methanol:28% aqueous ammonia=100:1:0.1 to 50:1:0.1 to 30:1:0.1) to obtain 257 mg of N-[2-(dimethylamino)ethyl]-2-ethyl-1-(4-fluorobenzyl)-3-methyl-1H-indole-5-carboxamide as a colorless oily material. This product was dissolved in 2.5 ml of acetonitrile at 80° C., and 67 mg of oxalic acid was added, followed by stirring at 80° C. for 10 minutes and then stirring at room temperature for 2 hours. The resulting solid was collected by filtration and then washed with acetonitrile to obtain 236 mg of N-[2-(dimethylamino)ethyl]-2-ethyl-1-(4-fluorobenzyl)-3-methyl-1H-indole-5-carboxamide oxalate as a pale purple solid.

Example 4

A 219 mg portion of 1-benzyl-N-(diaminomethylene)-3-formyl-1H-indole-5-carboxamide was suspended in 10 ml of methanol, and 69 mg of sodium borohydride was added at 0° C., followed by stirring at room temperature for 1 hour. After evaporation of the solvent and subsequent addition of water, the thus precipitate solid was purified by silica gel column chromatography (Clomatorex (registered trademark), methanol:chloroform:water=50:1:0.1 to 30:1:0.1 to 20:1:0.1 to 10:1:0.1). The thus obtained product was suspended in 7 ml of ethanol, and 0.34 ml of 4 M hydrogen chloride/ethyl acetate was added, followed by stirring at room temperature for 1 hour. The resulting solid was collected by filtration and then washed with ethanol and dried under a reduced pressure. After dissolving this solid in 2 ml of an N,N-dimethylformamide and adjusting its pH to 9 with a 1 M sodium hydroxide aqueous solution, the solvent was evaporated, water was added thereto and the solid precipitated thereby was purified by silica gel column chromatography (Clomatorex (registered trademark), methanol:chloroform:water=100:1:0.1 to 50:1:0.1 to 30:1:0.1 to 20:1:0.1). The resulting product was crystallized with ethanol/water to obtain 213 mg of 1-benzyl-N-(diaminomethylene)-3-ethoxymethyl-1H-indole-5-carboxamide as a colorless solid.

Example 5

A 775 mg portion of tert-butyl 3-({[1-(4-fluorobenzyl)-2,3-dimethyl-1H-indol-5-yl]carbonyl}amino)pyrrolidine-1-carboxylate was dissolved in 3.2 ml of ethyl acetate, and 2.1 ml of 4 M hydrogen chloride/ethyl acetate was added, followed by stirring at room temperature for 15 minutes. Then, 2 ml of methanol was added, followed by overnight stirring at room temperature. The resulting solid was collected by filtration and washed with ethyl acetate/methanol (3/1) to obtain 479 mg of 1-(4-fluorobenzyl)-2,3-dimethyl-N-pyrrolidin-3-yl-1H-indole-5-carboxamide hydrochloride as a pale pink solid.

Example 6

A 317 mg portion of 1-(4-fluorobenzyl)-2,3-dimethyl-N-pyrrolidin-3-yl-1H-indole-5-carboxamide hydrochloride was suspended in 8 ml of dichloromethane, 0.11 ml of triethylamine and 0.13 ml of formaldehyde (a 37% aqueous solution) were added, and then 836 mg of sodium triacetoxy borohydride was added under ice-cooling, followed by stirring at room temperature for 1.5 hours. A 1 M sodium hydroxide aqueous solution was added to the reaction liquid, followed by extraction with chloroform. The organic layer was washed with saturated brine and dried over anhydrous sodium sulfate. After evaporation of the solvent under a reduced pressure, the residue was purified by silica gel column chromatography (chloroform:methanol:28% aqueous ammonia=100:1:0.1 to 50:1:0.1 to 30:1:0.1 to 20:1:0.1) to obtain 279 mg of 1-(4-fluorobenzyl)-2,3-dimethyl-N-(1-methylpyrrolidin-3-yl)-1H-indole-5-carboxamide as a colorless solid. This product was suspended in 2 ml of ethanol, and 0.27 ml of 4 M hydrogen chloride-ethyl acetate was added, followed by stirring at room temperature for 2 hours. After evaporation of the solvent under a reduced pressure, the residue was dissolved in 2 ml of acetone, followed by stirring at room temperature for 2 hours. The resulting solid was collected by filtration and then washed with acetone to obtain 261 mg of 1-(4-fluorobenzyl)-2,3-dimethyl-N-(1-methylpyrrolidin-3-yl)-1H-indole-5-carboxamide hydrochloride as a pale pink solid.

Example 7

A 403 mg portion of methyl 1-benzyl-3-[(dimethylamino)methyl]-1H-indole-5-carboxylate was dissolved in 7.5 ml of ethanol, and 2.5 ml of a 1 M sodium hydroxide aqueous solution was added, followed by overnight stirring at 80° C. After evaporation of ethanol under a reduced pressure, 2.5 ml of 1 M hydrochloric acid was added thereto under ice-cooling, and the solvent was evaporated under a reduced pressure. The residue was dissolved in 12 ml of N,N-dimethylformamide, and 405 mg of 1,1'-carbonyldiimidazole was added, followed by stirring at 50° C. for 1 hour. Then, 563 mg of guanidine carbonate was added, followed by overnight stirring at room temperature. The solvent was evaporated under a reduced pressure, and water was added thereto under ice-cooling, followed by stirring at the same temperature for 1 hour. The thus precipitated solid was collected by filtration and purified by silica gel column chromatography (Clomatorex (registered trademark), methanol:chloroform:water=50:1:0.1 to 30:1:0.1 to 20:1:0.1 to 10:1:0.1) to obtain 266 mg of 1-benzyl-N-(diaminomethylene)-3-[(dimethylamino)methyl]-1H-indole-5-carboxamide as a colorless solid. This product was suspended in 2.5 ml of ethanol, and 0.48 ml of 4 M hydrogen chloride/ethyl acetate was added, followed by stirring at room temperature for 30 minutes. Then, 7.5 ml of ethyl acetate was added thereto, followed by stirring at room temperature for 30 minutes. The thus precipitated solid was collected by filtration and washed with a mixed solution of ethyl acetate:methanol=3:1 to obtain 289 mg of 1-benzyl-N-(diaminomethylene)-3-[(dimethylamino)methyl]-1H-indole-5-carboxamide dihydrochloride as a pale pink solid.

Example 8

A 10.9 mg portion of ethyl 2,3-dimethyl-1H-indole-5-carboxylate was dissolved in 0.300 ml of N,N-dimethylformamide, and 2.0 mg of sodium hydride (60% dispersion in oil) was added, followed by stirring at room temperature for 30 minutes. Then, 6.3 mg of 1-(bromomethyl)-2-fluorobenzene was added, followed by overnight stirring at room temperature. A saturated sodium bicarbonate aqueous solution was added to the reaction liquid, followed by extraction with chloroform. The solvent of the organic layer was evaporated under a reduced pressure, and the residue was dissolved in a mixed solvent of 0.50 ml tetrahydrofuran and 0.50 ml methanol. Then, 0.50 ml of a 1 M sodium hydroxide aqueous solution was added, followed by overnight stirring at 60° C. At room temperature, a 1 M hydrochloric acid aqueous solution was added to the reaction liquid to acidify the water layer, followed by extraction with chloroform. The solvent of the organic layer was evaporated under a reduced pressure, and 0.60 ml an N,N-dimethylformamide solution of 12 mg of 1,1'-carbonylbis-1H-imidazole was added to the residue, followed by stirring at 50° C. for 2 hours. A solution prepared by adding 26 mg of guanidine hydrochloride to 0.400 ml of an N,N-dimethylformamide solution of 10 mg of sodium hydride (60% dispersion in oil) and stirring at room temperature for 30 minutes was added to this reaction liquid at room temperature, followed by overnight stirring at room temperature. Water was added to the reaction liquid, followed by extraction with chloroform. The solvent of the organic layer was evaporated under a reduced pressure, and the resulting residue was purified by a fractional high performance liquid chromatography (acetonitrile/a 0.1% trifluoroacetic acid aqueous solution) to obtain 9.5 mg of N-(diaminomethylene)-1-(2-fluorobenzyl)-2,3-dimethyl-1H-indole-5-carboxamide.

Example 9

A 8.9 mg portion of 1-(4-fluorobenzyl)-2,3-dimethyl-1H-indole-5-carboxylic acid, 3.1 mg of N,N-dimethylpropane-1,3-diamine, 4.1 mg of 1-hydroxybenzotriazole (HOBt) and 0.0083 ml of triethylamine were dissolved in 1.0 ml of N,N-dimethylformamide, and 100 mg of PS-Carbodiimide (Argonaut Technologies, Inc., USA) was added, followed by overnight stirring at room temperature. Then, 50 mg of MP-Carbodiimide (Argonaut Technologies, Inc., USA) and 50 mg of PS-Isocyanate (Argonaut Technologies, Inc., USA) was added to the reaction liquid at room temperature, followed by stirring for 4 hours. Then, the reaction liquid was filtered. By concentrating the filtrate under a reduced pressure, 9.5 mg of N-[3-(dimethylamino)propyl]-(4-fluorobenzyl)-2,3-dimethyl-1H-indole-5-carboxamide was obtained.

Example 10

A 200 mg portion of 1-(4-fluorobenzyl)-2-methoxy-1H-benzimidazole-5-carboxylic acid and 130 mg of 1,1'-carbonyldiimidazole were dissolved in 5 ml of N,N-dimethylformamide, followed by stirring at 50° C. for 1 hour. Then, 144 mg of guanidine carbonate was added, followed by stirring at 50° C. for 5 hours. After evaporation of the solvent, water was added thereto and the thus precipitated solid was suspended in 5 ml of ethyl acetate. A 5 ml portion of 4 M hydrogen chloride/ethyl acetate was added thereto under ice-cooling, followed by stirring at room temperature for 1 hour. Then, the solvent was evaporated under a reduced pressure and the residue was recrystallized from 2-propanol/water to obtain 126 mg of N-[1-(4-fluoro-benzyl)-2-oxo-2,3-dihydro-1H-benzimidazole-5-carbonyl]-guanidine hydrochloride as a colorless solid.

In the same manner as the methods of the above-mentioned Examples 1 to 10, the Example compounds 11 to 252 shown in the following Tables 15 to 41 were produced using respectively corresponding starting materials. Structures and physical data of the Example compounds are shown in the following Tables 15 to 41.

TABLE 3

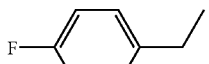

| REx | RSyn | R² | R | Dat |
|---|---|---|---|---|
| 21 | 4 | iPr | Et | FAB: 260 |
| 22 | 3 | | H | FAB: 232 |
| 23 | 2 | tBuC(O)CH₂— | Et | FAB: 316 |
| 24 | 3 | | H | FAB: 288 |
| 8 | 8 | Ph | Et | ESI: 293 |
| 25 | 3 | | H | FAB: 266 |
| 26 | 2 | 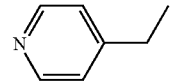 | Et | ESI: 326 |
| 27 | 3 | | H | ESI: 298 |
| 28 | 2 | 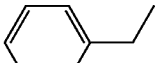 | Et | FAB: 309 |
| 29 | 3 | | H | FAB: 281 |
| 30 | 2 | 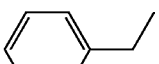 | Et | FAB: 309 |
| 31 | 3 | | H | FAB: 281 |
| 32 | 2 | 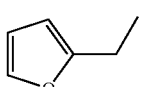 | Et | FAB: 309 |
| 33 | 3 | | H | FAB: 281 |
| 34 | 4 | 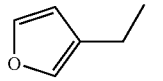 | Et | FAB: 298 |
| 35 | 3 | | H | FAB: 270 |

TABLE 3-continued

| REx | RSyn | R² | R | Dat |
|---|---|---|---|---|
| 36 | 4 | 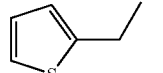 | Et | FAB: 298 |
| 37 | 3 | | H | FAB: 270 |
| 38 | 4 | 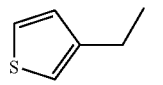 | Et | FAB: 314 |
| 39 | 3 | | H | FAB: 286 |
| 4 | 4 | 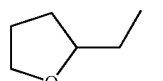 | Et | FAB: 314 |
| 40 | 3 | | H | FAB: 286 |
| 41 | 4 | cHexCH₂— | Et | FAB: 314 |
| 42 | 3 | | H | FAB: 286 |
| 43 | 2 | 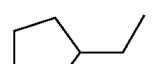 | Et | FAB: 302 |
| 44 | 3 | | H | FAB: 274 |
| 45 | 4 | 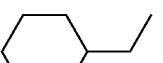 | Et | FAB: 302 |
| 46 | 3 | | H | FAB: 274 |
| 47 | 2 |  | Et | FAB: 316 |
| 48 | 3 | | H | FAB: 288 |

TABLE 4

| REx | RSyn | R² | R | Dat |
|---|---|---|---|---|
| 49 | 4 | 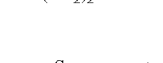 | Et | FAB: 302 |
| 50 | 3 | | H | FAB: 274 |
| 5 | 5 | Ph—(CH₂)₂— | Et | FAB: 322 |
| 51 | 3 | | H | FAB: 294 |
| 52 | 2 | 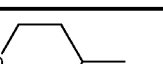 | Et | FAB: 348 |
| 53 | 3 | | H | FAB: 320 |

TABLE 5

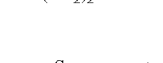

| REx | RSyn | R³ | R⁴ | R | Dat |
|---|---|---|---|---|---|
| 7 | 7 | HC(O)— | H | Me | FAB: 204 |
| 1 | 1 | Me | Et | Et | FAB: 232 |

TABLE 6

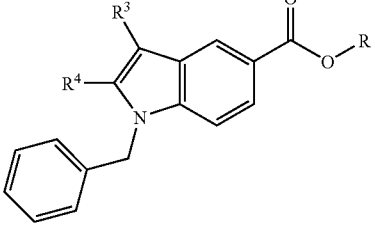

| REx | RSyn | R³ | R⁴ | R | Dat |
|---|---|---|---|---|---|
| 54 | 2 | HC(O)— | H | Me | FAB: 294 |
| 55 | 3 |  |  | H | ESI: 280 |
| 9 | 9 | HOCH₂— | H | Me | FAB(M⁺): 295 |
| 10 | 10 | MeOCH₂— | H | Me | FAB(M⁺): 309 |
| 56 | 3 |  |  | H | FAB(M⁺): 295 |
| 12 | 12 | Me | H | Me | FAB: 280 |
| 57 | 3 |  |  | H | FAB: 266 |
| 14 | 14 | Me₂NCH₂— | H | Me | FAB: 323 |
| 58 | 2 | MeS— | Me | Et | FAB: 340 |
| 59 | 3 |  |  | H | FAB: 312 |
| 13 | 13 | H | Me | Et | FAB: 294 |
| 60 | 3 |  |  | H | FAB: 266 |

TABLE 7

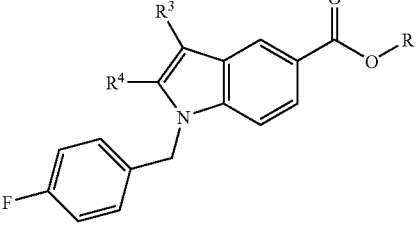

| REx | RSyn | R³ | R⁴ | R | Dat |
|---|---|---|---|---|---|
| 61 | 2 | MeS— | Me | Et | ESI: 358 |
| 62 | 3 |  |  | H | FAB: 330 |
| 15 | 15 | MeS(O)— | Me | Et | FAB: 374 |
| 63 | 3 |  |  | H | FAB(M⁺): 345 |
| 16 | 16 | MeS(O)₂— | Me | Et | FAB(M⁺): 389 |
| 64 | 3 |  |  | H | FAB(M⁺): 361 |
| 65 | 2 | Et | Me | Et | FAB: 340 |
| 66 | 3 |  |  | H | FAB: 312 |
| 67 | 2 | nPr | Me | Et | FAB: 354 |
| 68 | 3 |  |  | H | FAB: 326 |
| 69 | 1, 2 | iPr | Me | Et | FAB: 354 |
| 70 | 3 |  |  | H | FAB: 326 |
| 2 | 2 | Me | Me | Et | FAB: 340 |
| 3 | 3 |  |  | H | FAB: 312 |
| 71 | 1, 2 | Me | nPr | Et | FAB: 354 |
| 72 | 3 |  |  | H | FAB: 326 |
| 73 | 1, 2 | Et | Et | Et | FAB: 354 |
| 74 | 3 |  |  | H | FAB: 326 |
| 18 | 18 | MeOCH₂— | Me | H | FAB(M⁺): 327 |
| 75 | 18 | MeC(O)— | Me | H | FAB: 326 |

TABLE 8

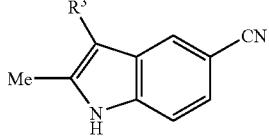

| REx | RSyn | R³ | Dat |
|---|---|---|---|
| 17 | 17 | H | ESI: 184 |
| 19 | 19 | H(O)C— | ESI: 198 |

TABLE 9

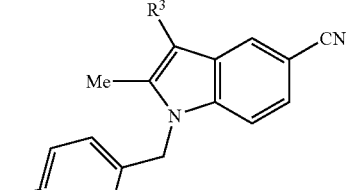

| REx | RSyn | R³ | Dat |
|---|---|---|---|
| 76 | 2 | H(O)C— | FAB: 293 |
| 77 | 9 | HOCH₂— | FAB: 295 |
| 78 | 2 | MeC(O)— | FAB: 307 |

TABLE 10

| REx | RSyn | Str | Dat |
|---|---|---|---|
| 11 | 11 | 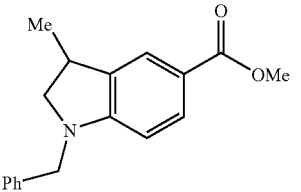 | FAB: 282 |
| 79 | 1 | 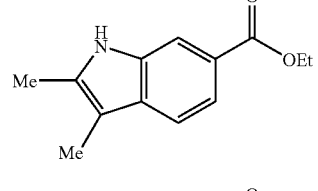 | FAB: 218 |
| 80 | 2 | 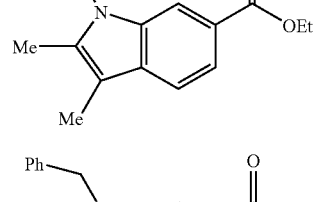 | FAB: 308 |
| 81 | 3 |  | FAB(M⁺): 279 |

TABLE 10-continued

| REx | RSyn | Str | Dat |
|---|---|---|---|
| 6 | 6 | [1-benzyl-2,3-dimethylindoline-5-carboxylic acid ethyl ester] | FAB: 310 |
| 82 | 3 | [1-benzyl-2,3-dimethylindoline-5-carboxylic acid] | FAB: 282 |
| 83 | 3 | [1-benzyl-3-methylindoline-5-carboxylic acid] | FAB: 268 |

TABLE 11

[Structure: 1-(4-fluorobenzyl)-2-$R^7$-benzimidazole-5-carboxylic acid ester -O-R]

| REx | RSyn | $R^7$ | R | Dat |
|---|---|---|---|---|
| 84 | 2 | Me | Me | ESI: 299 |
| 20 | 20 |  | H | ESI: 285 |
| 85 | 2 | H | Me | ESI: 285 |
| 86 | 20 |  | H | ESI: 271 |
| 87 | 2 | MeO— | Me | ESI: 315 |
| 88 | 20 |  | H | ESI: 301 |
| 89 | 2 | F$_3$C— | Me | ESI: 353 |
| 90 | 20 |  | H | ESI: 339 |

TABLE 12

[Structure: 1-(4-fluorobenzyl)-2-$R^7$-benzimidazole-6-carboxylic acid ester -O-R]

| REx | RSyn | $R^7$ | R | Dat |
|---|---|---|---|---|
| 91 | 2 | Me | Me | ESI: 299 |
| 92 | 20 |  | H | ESI: 285 |

TABLE 12-continued

| REx | RSyn | $R^7$ | R | Dat |
|---|---|---|---|---|
| 93 | 2 | H | Me | ESI: 285 |
| 94 | 20 |  | H | ESI: 271 |
| 95 | 2 | MeO— | Me | ESI: 315 |
| 96 | 20 |  | H | ESI: 301 |

TABLE 13

[Structure: 1-$R^2$-1,2,3,4-tetrahydroquinoline-6-carboxylic acid ester -O-R]

| REx | RSyn | $R^2$ | R | Dat |
|---|---|---|---|---|
| 97 | 2 | Bn | Me | ESI: 282 |
| 98 | 20 |  | H | ESI: 268 |
| 99 | 2 | 4-fluorobenzyl | Me | ESI: 300 |
| 100 | 20 | | H | ESI: 286 |

TABLE 14

[Structure: 4-(4-fluorobenzyl)-3,4-dihydro-2H-1,4-benzoxazine-7-carboxylic acid ester -O-R]

| REx | RSyn | R | Dat |
|---|---|---|---|
| 101 | 2 | Me | ESI: 302 |
| 102 | 20 | H | ESI: 288 |

TABLE 15

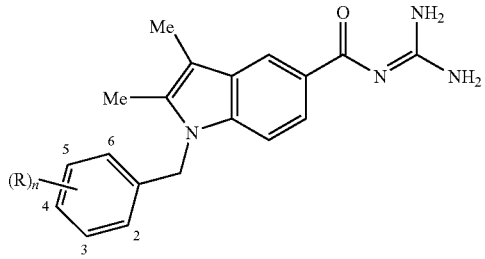

| Ex | Syn | (R)ₙ— | Sal | Dat |
|---|---|---|---|---|
| 11 | 1 | null | HCl | FAB: 321 |
| 8 | 8 | 2-F | | ESI: 339 |
| 12 | 8 | 2-Cl | | ESI: 355 |
| 13 | 8 | 2-Br | | ESI: 399 |
| 14 | 8 | 2-CF₃ | | ESI: 389 |
| 15 | 8 | 2-Me | | ESI: 335 |
| 16 | 8 | 3-F | | ESI: 339 |
| 17 | 8 | 3-Cl | | ESI: 355 |
| 18 | 8 | 3-Br | | ESI: 399 |
| 19 | 8 | 3-CF₃ | | ESI: 389 |
| 20 | 8 | 3-Me | | ESI: 335 |
| 21 | 8 | 3-OMe | | ESI: 351 |
| 22 | 8 | 3-NO₂ | | ESI: 366 |
| 23 | 8 | 3-Ph | | ESI: 397 |
| 24 | 1 | 4-F | HCl | FAB: 339 NMR: 2.29 (3 H, s), 2.30 (3 H, s), 5.46 (2 H, s), 7.00-7.06 (2 H, m), 7.10-7.16 (2 H, m), 7.57 (1 H, d, J = 8.4 Hz), 7.83-7.86 (1 H, m), 8.45 (2 H, brs), 8.54 (1 H, d, J = 1.6 Hz), 8.87 (2 H, brs), 11.93 (1 H, s) |
| 25 | 8 | 4-Cl | | ESI: 355 |
| 26 | 8 | 4-Br | | ESI: 399 |
| 27 | 8 | 4-CF₃ | | ESI: 389 |
| 28 | 8 | 4-Me | | ESI: 335 |
| 29 | 8 | 4-iPr | | ESI: 363 |
| 30 | 8 | 4-NO₂ | | ESI: 366 |
| 31 | 8 | 4-S(O)₂Me | | ESI: 399 |
| 32 | 8 | 4-Ph | | ESI: 397 |
| 33 | 8 | 3,4-diF | | ESI: 357 |
| 34 | 8 | 2,4-diF | | ESI: 357 |
| 35 | 8 | 2,5-diF | | ESI: 357 |
| 36 | 8 | 3,5-diF | | ESI: 357 |
| 37 | 8 | 2,6-diF | | ESI: 357 |

TABLE 16

| 38 | 8 | 2,3-diF | ESI: 357 |
|---|---|---|---|
| 39 | 8 | 2-F-3-Cl | ESI: 373 |
| 40 | 8 | 2-Br-5-F | ESI: 417 |
| 41 | 8 | 2-F-3-Me | ESI: 353 |
| 42 | 8 | 3,4-diCl | ESI: 389 |
| 43 | 8 | 3-Cl-5-F | ESI: 373 |
| 44 | 8 | 3-Me-4-F | ESI: 353 |
| 45 | 8 | 3-Cl-4-F | ESI: 373 |

TABLE 17

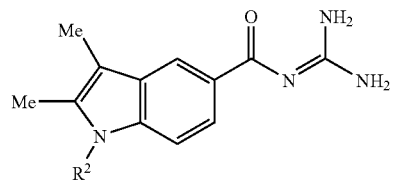

| Ex | Syn | R² | Sal | Dat |
|---|---|---|---|---|
| 46 | 1 | H | HCl | ESI: 231 |
| 47 | 1 | iPr | HCl | FAB: 273 |
| 48 | 8 | Et | | ESI: 259 |
| 49 | 8 | iBu | | ESI: 287 |
| 50 | 8 | iPen | | ESI: 301 |
| 51 | 1 | Ph | HCl | FAB: 307 |
| 52 | 1 | 4-methyltetrahydropyranyl | HCl | FAB: 315 |
| 53 | 1 | cHex-CH₂— | HCl | FAB: 327 |
| 54 | 1 | 4-pyridyl-CH₂— | 2HCl | FAB: 322 |
| 55 | 1 | 3-pyridyl-CH₂— | 2HCl | ESI: 322 |
| 56 | 1 | 2-pyridyl-CH₂— | 2HCl | ESI: 322 |
| 57 | 1 | 2-furyl-CH₂— | HCl | FAB: 311 |
| 58 | 1 | 3-furyl-CH₂— | HCl | FAB: 311 |
| 59 | 1 | 2-thienyl-CH₂— | HCl | FAB: 327 |
| 1 | 1 | 3-thienyl-CH₂— | HCl | FAB: 327 |
| 60 | 1 | 2-tetrahydrofuryl-CH₂— | HCl | FAB: 315 |
| 61 | 1 | 3-tetrahydrofuryl-CH₂— | HCl | FAB: 315 |
| 62 | 1 | 2-tetrahydropyranyl-CH₂— | HCl | FAB: 329 |

TABLE 17-continued

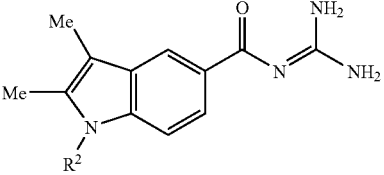

| Ex | Syn | R² | Sal | Dat |
|---|---|---|---|---|
| 63 | 8 | (2-naphthylethyl) | | ESI: 371 |

TABLE 18

| 64 | 8 | (4-(pyrrol-1-yl)phenylethyl) | | ESI: 386 |
| 65 | 8 | (5-chlorobenzothiophen-3-ylethyl) | | ESI: 411 |
| 66 | 8 | (quinolin-8-ylethyl) | | ESI: 372 |
| 67 | 8 | (benzothiazol-2-ylethyl) | | ESI: 378 |
| 68 | 8 | (5-trifluoromethylfuran-2-ylethyl) | | ESI: 379 |
| 69 | 8 | (5-methylisoxazol-3-ylethyl) | | ESI: 326 |
| 70 | 8 | (benzisoxazol-3-ylethyl) | | ESI: 362 |
| 71 | 8 | (3,5-dimethylisoxazol-4-ylethyl) | | ESI: 340 |

TABLE 18-continued

| 72 | 8 | (5-cyclopropyl-1,3,4-thiadiazol-2-ylethyl) | | ESI: 369 |
| 73 | 8 | (5-trifluoromethyl-1,2,4-oxadiazol-3-ylethyl) | | ESI: 369 |
| 74 | 8 | Ph₂CH— | | ESI: 397 |
| 75 | 8 | PhCH(Me)- | | ESI: 335 |
| 76 | 2 | tBuCH(OH)CH₂— | HCl | FAB: 331 |
| 77 | 1 | tBuC(O)CH₂— | HCl | FAB: 329 |
| 78 | 8 | PhC(O)C(Me)₂- | | ESI: 377 |

TABLE 19

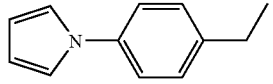

| Ex | Syn | R²¹ | n | Sal | Dat |
|---|---|---|---|---|---|
| 79 | 8 | cHex | 2 | | ESI: 341 |
| 80 | 8 | Me₂N— | 2 | | ESI: 302 |
| 81 | 8 | Et₂N— | 2 | | ESI: 330 |
| 82 | 8 | Ph₂CH— | 2 | | ESI: 425 |
| 83 | 1 | Ph | 2 | HCl | FAB: 335 |
| 84 | 8 |  | 3 | | ESI: 349 |
| 85 | 8 |  | 4 | | ESI: 363 |
| 86 | 8 |  | 5 | | ESI: 377 |
| 87 | 8 | PhO— | 2 | | ESI: 351 |
| 88 | 8 |  | 3 | | ESI: 365 |
| 89 | 8 | (4-fluorophenoxy) | 2 | | ESI: 369 |
| 90 | 8 | (2-methoxyphenoxy) | 4 | | ESI: 409 |
| 91 | 8 | (4-methoxyphenoxy) | 4 | | ESI: 409 |
| 92 | 8 | (pyrrolidin-1-yl) | 2 | | ESI: 328 |
| 93 | 8 | (pyrrol-1-yl) | 3 | | ESI: 338 |
| 94 | 8 | (piperidin-1-yl) | 2 | | ESI: 342 |
| 95 | 8 | (piperidin-1-yl) | 3 | | ESI: 356 |
| 96 | 8 | (morpholin-4-yl) | 2 | | ESI: 344 |

TABLE 20

| Ex | Syn | R | R³ | R⁴ | Sal | Dat |
|---|---|---|---|---|---|---|
| 97 | 1 | H | HC(O)— | H | HCl | FAB: 321 |
| 2 | 2 | H | HOCH₂— | H | — | FAB: 323 |
| 98 | 1 | H | MeOCH₂— | H | | FAB: 337 |
| 4 | 4 | H | EtOCH₂— | H | — | FAB: 351 |
| 99 | 1 | H | Me | H | HCl | FAB: 307 |
| 7 | 7 | H | Me₂NCH₂— | H | 2HCl | FAB: 350 |
| 100 | 1 | H | H | Me | HCl | FAB: 307 |
| 101 | 1 | H | MeS— | Me | HCl | FAB: 353 |
| 102 | 1 | F | MeS(O)₂— | Me | HCl | FAB: 403 NMR: 2.70 (3 H, s), 3.29 (3 H, s), 5.63 (2 H, s), 7.12-7.20 (4 H, s), 7.82 (1 H, d, J = 8.8 Hz), 8.01-8.03 (1 H, m), 8.48 (2 H, brs), 8.58 (1 H, d, J = 1.6 Hz), 8.72 (2 H, brs), 11.98 (1 H, s) |
| 103 | 1 | F | Et | Me | HCl | FAB: 353 |
| 104 | 1 | F | MeC(O)— | Me | (CO₂H)₂ | FAB: 367 |

TABLE 21

| Ex | Syn | Str | Sal | Dat |
|---|---|---|---|---|
| 105 | 1 | (1-benzyl-2,3-dimethyl-1H-indole-6-carboxamide guanidine) | HCl | FAB: 321 |
| 106 | 1 | (1-benzyl-2,3-dimethyl-indoline-5-carboxamide guanidine) | HCl | FAB: 323 |
| 107 | 1 | (1-benzyl-3-methyl-indoline-5-carboxamide guanidine) | HCl | FAB: 309 |

TABLE 22

[Structure: 1-(4-fluorobenzyl)-2,3-dimethyl-1H-indole-5-carboxamide with N-H-R¹² group]

| Ex | Syn | R¹² | Sal | Dat |
|----|-----|-----|-----|-----|
| 108 | 3 | —CH₂C(Me)₂NMe₂ | (CO₂H)₂ | FAB: 396 |
| 109 | 9 | —CH₂C(Me)₂CH₂NMe₂ | | ESI: 410 |
| 110 | 9 | —CH₂CH(Ph)NMe₂ | | ESI: 444 |
| 111 | 5 | azetidine-NH | HCl | FAB: 352 |
| 112 | 3 | azetidine-N-Me | (CO₂H)₂ | FAB: 366 |
| 5 | 5 | pyrrolidine-NH | HCl | FAB: 366 |
| 6 | 6 | pyrrolidine-N-Me | HCl | FAB: 380 |
| 113 | 9 | pyrrolidine-N-Bn | | ESI: 456 |
| 114 | 3 | (S)-pyrrolidine-N-Me | HCl | FAB: 380<br>NMR: 2.01-2.35 (7 H, m), 2.44-2.53 (1 H, m), 2.86 (3 H, s), 3.03-3.09 (1 H, m), 3.24-3.36 (1 H, m), 3.54-3.57 (1 H, m), 3.72-3.87 (1 H, m), 4.55-4.72 (1 H, m), 5.42 (2 H, s), 6.98-7.01 (2 H, m), 7.09-7.14 (2 H, m), 7.41-7.43 (1 H, m), 7.61-7.67 (1 H, m), 8.07-8.16 (1 H, m), 8.65-8.71 (1 H, m), 10.77-10.91 (1 H, m) |
| 115 | 3 | (S)-pyrrolidine-N-Et | (CO₂H)₂ | FAB: 394 |
| 116 | 3 | (S)-pyrrolidine-N-iPr | HCl | FAB: 408 |

TABLE 23
| 117 | 9 | 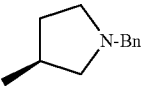 | | ESI: 456 |
|---|---|---|---|---|
| 118 | 3 | 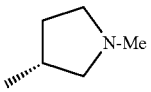 | HCl | FAB: 380<br>NMR: 2.04-2.17 (1 H, m), 2.26 (3 H, s), 2.28 (3 H, s), 2.43-2.53 (1 H, m), 2.84-2.88 (3 H, m), 3.04-3.09 (1 H, m), 3.24-3.37 (1 H, m), 3.54-3.57 (1 H, m), 3.68-3.89 (1 H, m), 4.54-4.76 (1 H, m), 5.41 (2 H, s), 6.97-7.01 (2 H, m), 7.09-7.14 (2 H, m), 7.41-7.44 (1 H, m), 7.61-7.67 (1 H, m), 8.07-8.16 (1 H, m), 8.66-8.72 (1 H, m), 10.77-11.01 (1 H, m) |
| 119 | 3 | 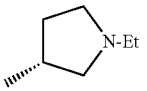 | (CO$_2$H)$_2$ | FAB: 394 |
| 120 | 3 | 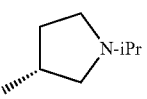 | HCl | FAB: 408 |
| 121 | 9 | 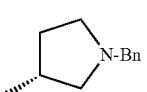 | | ESI: 456 |
| 122 | 5 | 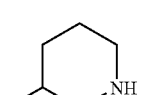 | HCl | FAB: 380 |
| 123 | 6 | 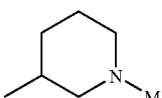 | HCl | FAB: 394 |
| 124 | 9 | 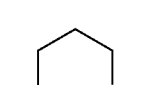 | | ESI: 408 |
| 125 | 9 | 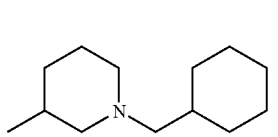 | | ESI: 476 |
| 126 | 9 | 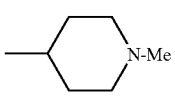 | | ESI: 394 |
| 127 | 9 | 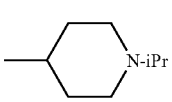 | | ESI: 422 |

TABLE 24

| | | | | |
|---|---|---|---|---|
| 128 | 3 | (quinuclidine with methyl, wedge down) | (CO₂H)₂ | FAB: 406 |
| 129 | 3 | (quinuclidine with methyl, wedge up) | (CO₂H)₂ | FAB: 406 |
| 130 | 9 | 2-ethyl-1-iPr-pyrrolidine | | ESI: 422 |
| 131 | 9 | 2-ethyl-1-Me-piperidine | | ESI: 408 |
| 132 | 9 | 2-ethyl-4-Bn-morpholine | | ESI: 486 |
| 133 | 3 | (S)-2-ethyl-1-Me-pyrrolidine | (CO₂H)₂ | FAB: 394<br>NMR: 1.77-1.88 (2 H, m), 1.91-2.01 (1 H, m), 2.09-2.17 (1 H, m), 2.25 (3 H, s), 2.28 (3 H, m), 2.87 (3 H, m), 3.00-3.07 (1 H, m), 3.47-3.55 (2 H, m), 3.60-3.69 (2 H, m), 5.42 (2 H, s), 6.97-7.01 (2 H, m), 7.09-7.14 (2 H, m), 7.43 (1 H, d, J = 8.6 Hz), 7.61-7.64 (1 H, m), 8.07 (1 H, s), 8.73-8.76 (1 H, m) |
| 134 | 9 | (S)-2-ethyl-1-Et-pyrrolidine | | ESI: 408 |

TABLE 25

| | | | | |
|---|---|---|---|---|
| 135 | 3 | (R)-2-ethyl-1-Me-pyrrolidine | (CO₂H)₂ | FAB: 394<br>NMR: 1.78-1.89 (2 H, m), 1.92-2.02 (1 H, m), 2.09-2.17 (1 H, m), 2.25 (3 H, s), 2.28 (3 H, s), 2.87 (3 H, s), 3.01-3.08 (1 H, m), 3.50-3.56 (2 H, m), 3.61-3.70 (2 H, m), 5.42 (2 H, s), 6.98-7.01 (2 H, m), 7.09-7.14 (2 H, m), 7.43 (1 H, d, J = 8.6 Hz), 7.62-7.64 (1 H, m), 8.07 (1 H, s), 8.74-8.77 (1 H, m) |
| 136 | 9 | (R)-2-ethyl-1-Et-pyrrolidine | | ESI: 408 |
| 137 | 3 | 1-ethyl-1-NMe₂-cyclopropane | (CO₂H)₂ | FAB: 394 |

TABLE 25-continued
| | | | | |
|---|---|---|---|---|
| 138 | 3 | 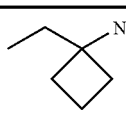 | HCl | FAB: 408 |
| 139 | 3 | 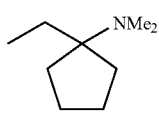 | HCl | FAB: 422 |
| 140 | 3 | 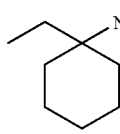 | (CO$_2$H)$_2$ | FAB: 436 |
| 141 | 3 | 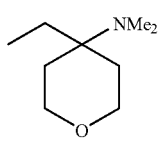 | (CO$_2$H)$_2$ | FAB: 438 |
| 142 | 3 | 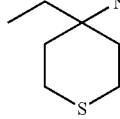 | HCl | FAB: 454 |
| 143 | 9 | 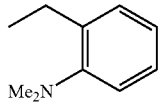 | | ESI: 430 |
| 144 | 9 | 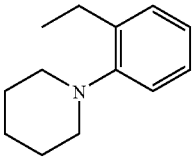 | | ESI: 470 |
TABLE 26
| | | | |
|---|---|---|---|
| 145 | 9 | 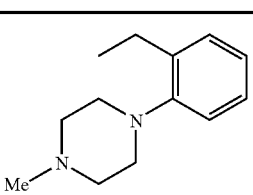 | ESI: 485 |
| 146 | 9 | 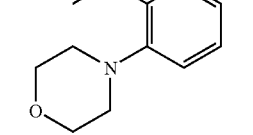 | ESI: 472 |
TABLE 26-continued
| | | | |
|---|---|---|---|
| 147 | 9 | 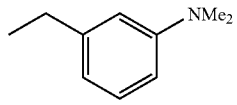 | ESI: 430 |
| 148 | 9 | 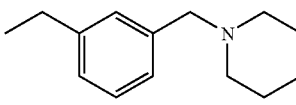 | ESI: 498 |
| 149 | 9 | 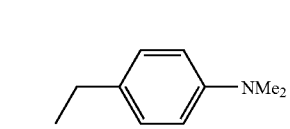 | ESI: 430 |

TABLE 26-continued
| Ex | Syn | Structure | Dat |
|---|---|---|---|
| 150 | 9 | 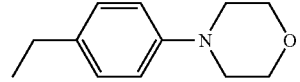 | ESI: 472 |
| 151 | 9 | 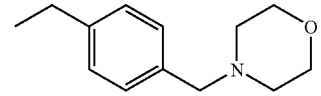 | ESI: 486 |
| 152 | 9 | 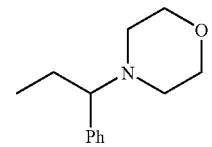 | ESI: 486 |
| 153 | 9 | 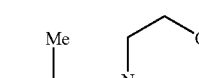 | ESI: 424 |
| 154 | 9 | 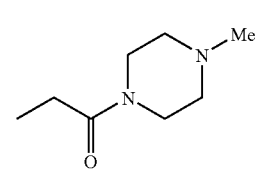 | ESI: 437 |
| 155 | 9 | 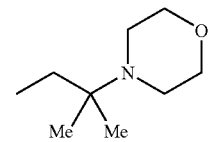 | ESI: 438 |
TABLE 27
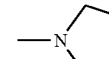
| Ex | Syn | n | —N(R$^{14}$)$_2$ | Sal | Dat |
|---|---|---|---|---|---|
| 156 | 3 | 2 | —NMe$_2$ | (CO$_2$H)$_2$ | FAB: 368<br>NMR 2.25 (3 H, s), 2.28 (3 H, s), 2.80 (6 H, s), 320 (2 H, t, J = 6.0 Hz), 3.52-3.66 (2 H, m), 5.42 (2 H, s), 6.94-7.03 (2 H, m), 7.07-7.16 (2 H, m), 7.43 (1 H, d, J = 8.8 Hz), 7.61 (1 H, dd, J = 8.8, 1.2 Hz), 8.05 (1 H, d, J = 1.2 Hz), 8.56 (1 H, t, J = 5.2 Hz) |
| 9 | 9 | 3 | | | ESI: 382 |
| 157 | 9 | 2 | —NEt$_2$ | | ESI: 396 |
| 158 | 9 | 3 | | | ESI: 410 |
| 159 | 9 | 3 | —N(nBu)$_2$ | | ESI: 466 |
| 160 | 9 | 3 | —N(—CH$_2$CH$_2$OH)$_2$ | | ESI: 442 |
| 161 | 9 | 3 | —N(Me)Ph | | ESI: 444 |
TABLE 28
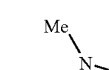
| Ex | Syn | n | R | Dat |
|---|---|---|---|---|
| 162 | 9 | 2 | 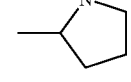 | ESI: 394 |
| 163 | 9 | 3 | | ESI: 408 |
| 164 | 9 | 4 | | ESI: 422 |
| 165 | 9 | 2 | 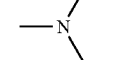 | ESI: 408 |
| 166 | 9 | 2 | 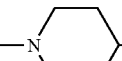 | ESI: 408 |
| 167 | 9 | 2 | 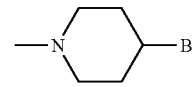 | ESI: 498 |
| 168 | 9 | 2 | 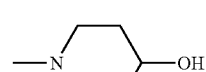 | ESI: 424 |

TABLE 28-continued

Structure: 1-(4-fluorobenzyl)-2,3-dimethyl-1H-indole-5-carboxamide with –NH–(CH₂)ₙ–R

| Ex | Syn | n | R | Dat |
|---|---|---|---|---|
| 169 | 9 | 2 | morpholin-4-yl | ESI: 410 |
| 170 | 9 | 3 | morpholin-4-yl | ESI: 424 |
| 171 | 9 | 2 | 4-methylpiperazin-1-yl | ESI: 423 |
| 172 | 9 | 3 | 4-methylpiperazin-1-yl | ESI: 437 |
| 173 | 9 | 2 | 4-benzylpiperazin-1-yl | ESI: 499 |
| 174 | 9 | 2 | (2R,6S)-2,6-dimethylmorpholin-4-yl | ESI: 438 |
| 175 | 9 | 3 | 2-methylpiperidin-1-yl | ESI: 436 |
| 176 | 9 | 3 | azepan-1-yl | ESI: 436 |

TABLE 29

Structure: 1-(4-fluorobenzyl)-2,3-dimethyl-1H-indole-5-carboxamide with N(Me)(R¹²)

| Ex | Syn | R¹² | Sal | Dat |
|---|---|---|---|---|
| 177 | 6 | 1-methylazetidin-3-yl | (CO₂H)₂ | FAB: 380 |
| 178 | 9 | 1-methylpyrrolidin-3-yl | | ESI: 394 |
| 179 | 9 | 1-benzyl-3-methylpyrrolidin-3-yl | | ESI: 470 |
| 180 | 9 | 2-ethyl-1-methylpyrrolidin-2-yl | | ESI: 408 |
| 181 | 9 | 2-ethyl-1-methylpiperidin-2-yl | | ESI: 422 |

TABLE 30

Structure: 1-(4-fluorobenzyl)-2,3-dimethyl-1H-indole-5-carboxamide with N(R¹¹)–(CH₂)ₙ–N(R¹⁴)₂

| Ex | Syn | R¹¹ | n | —N(R¹⁴)₂ | Dat |
|---|---|---|---|---|---|
| 182 | 9 | Me | 2 | —NMe₂ | ESI: 382 |
| 183 | 9 | Me | 3 | —NMe₂ | ESI: 396 |
| 184 | 9 | Bn | 2 | —NMe₂ | ESI: 458 |
| 185 | 9 | Me | 2 | —NEt₂ | ESI: 410 |
| 186 | 9 | Me | 2 | —N(iPr)₂ | ESI: 424 |

TABLE 31

Structure: 1-(4-fluorobenzyl)-2,3-dimethyl-1H-indole-5-carbonyl-piperazine with N-R

| Ex | Syn | R | Dat |
|---|---|---|---|
| 187 | 9 | Me | ESI: 380 |
| 188 | 9 | Et | ESI: 394 |
| 189 | 9 | iPr | ESI: 408 |
| 190 | 9 | iBu | ESI: 422 |
| 181 | 9 | cPen | ESI: 434 |

TABLE 31-continued
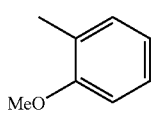
| Ex | Syn | R | Dat |
|---|---|---|---|
| 192 | 9 | cHex | ESI: 448 |
| 193 | 9 | —(CH₂)₂—NMe₂ | ESI: 437 |
| 194 | 9 | Ph | ESI: 442 |
| 195 | 9 | 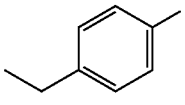 | ESI: 472 |
| 196 | 9 | 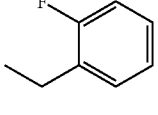 | ESI: 474 |
| 197 | 9 | 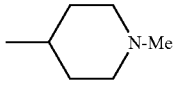 | ESI: 474 |
| 198 | 9 | —(CH₂)₂Ph | ESI: 470 |
| 199 | 9 | —(CH₂)₃Ph | ESI: 484 |
| 200 | 9 | —(CH₂)₄Ph | ESI: 498 |
| 201 | 9 | —(CH₂)₂OPh | ESI: 486 |
| 202 | 9 | —(CH₂)₃OPh | ESI: 500 |
| 203 | 9 | —(CH₂)₄OPh | ESI: 514 |
| 204 | 9 | —CH(Ph)₂ | ESI: 532 |
| 205 | 9 | 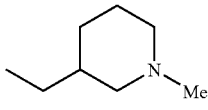 | ESI: 463 |
| 206 | 9 | 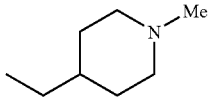 | ESI: 477 |
| 207 | 9 |  | ESI: 477 |
TABLE 32
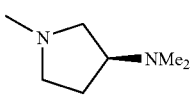
| Ex | Syn | R¹³ | Dat |
|---|---|---|---|
| 208 | 9 | 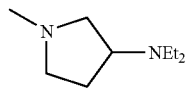 | ESI: 394 |
| 209 | 9 | 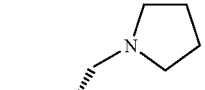 | ESI: 394 |
| 210 | 9 | 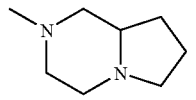 | ESI: 422 |
| 211 | 9 | 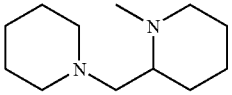 | ESI: 434 |
| 212 | 9 | 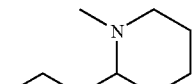 | ESI: 406 |
| 213 | 9 | | ESI: 420 |
| 214 | 9 | | ESI: 406 |
| 215 | 9 | | ESI: 462 |
| 216 | 9 | | ESI: 462 |

TABLE 33
| | | | |
|---|---|---|---|
| 217 | 9 | 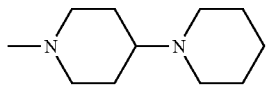 | ESI: 448 |
| 218 | 9 | 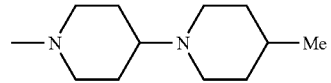 | ESI: 462 |
| 219 | 9 | 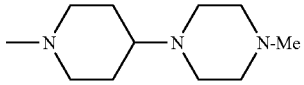 | ESI: 463 |
| 220 | 9 | 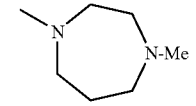 | ESI: 394 |
| 221 | 9 | 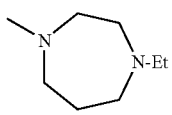 | ESI: 408 |
| 222 | 9 | 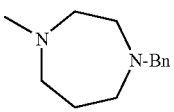 | ESI: 470 |
TABLE 34
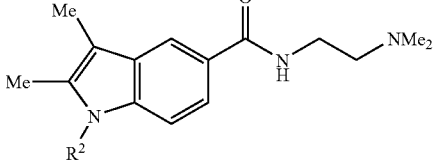
| Ex | Syn | $R^2$ | Sal | Dat |
|---|---|---|---|---|
| 223 | 3 | 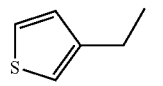 | $(CO_2H)_2$ | FAB: 356 |
| 224 | 3 | 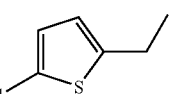 | $(CO_2H)_2$ | FAB: 390 |
| 225 | 3 | 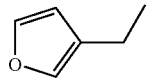 | $(CO_2H)_2$ | FAB: 340 |
TABLE 35
| Ex | Syn | $R^3$ | $R^4$ | Sal | Dat |
|---|---|---|---|---|---|
| 226 | 1 | Et | Me | $(CO_2H)_2$ | FAB: 382<br>NMR: 1.18 (3 H, t, J = 7.6 Hz), 2.73 (2 H, q, J = 7.6 Hz), 2.79 (6 H, s), 3.20 (2 H, t, J = 6.0 Hz), 3.61 (2 H, q, J = 6.0 Hz), 5.41 (2 H, s), 6.97-7.00 (2 H, m), 7.10-7.14 (2 H, m), 7.43 (1 H, d, J = 8.4 Hz), 7.60-7.62 (1 H, m), 8.09 (1 H, d, J = 1.2 Hz), 8.59 (1 H, t, J = 5.6 Hz) |
| 227 | 3 | nPr | Me | $(CO_2H)_2$ | FAB: 396 |
| 228 | 3 | iPr | Me | $(CO_2H)_2$ | FAB: 396 |
| 229 | 3 | MeS— | Me | $(CO_2H)_2$ | FAB: 400 |
| 230 | 3 | MeS(O)— | Me | $(CO_2H)_2$ | FAB: 416 |
| 231 | 3 | MeS(O)$_2$— | Me | $(CO_2H)_2$ | FAB: 432 |
| 3 | 3 | Me | Et | $(CO_2H)_2$ | FAB: 382 |
| 232 | 3 | Me | nPr | $(CO_2H)_2$ | FAB: 396 |
| 233 | 3 | Et | Et | $(CO_2H)_2$ | FAB: 396 |
| 234 | 9 | MeO—CH$_2$— | Me | | ESI: 398 |
| 235 | 9 | MeC(O)— | Me | $(CO_2H)_2$ | FAB: 396 |

TABLE 36

[Structure: indole with 3-Et, 2-R⁴, 1-(4-fluorobenzyl), 5-C(=O)NH-R¹²]

| Ex | Syn | R⁴ | R¹² | Sal | Dat |
|---|---|---|---|---|---|
| 236 | 3 | Me | (S)-3-methyl-N-methylpyrrolidin-1-yl (N-Me pyrrolidine with 3-Me) | (CO₂H)₂ | FAB: 394<br>NMR: 1.18 (3 H, t, J = 7.6 Hz), 2.05-2.13 (1 H, m), 2.29 (3 H, s), 2.34-2.43 (1 H, m), 2.74 (2 H, q, J = 7.6 Hz), 2.83 (3 H, s), 3.23-3.32 (2 H, m), 3.46-3.56 (2 H, m), 4.60-4.68 (1 H, m), 5.41 (2 H, s), 6.97-7.01 (2 H, m), 7.09-7.15 (2 H, m), 7.42 (1 H, d, J = 8.8 Hz), 7.60-7.63 (1 H, m), 8.09 (1 H, d, J = 1.6 Hz), 8.63 (1 H, d, J = 6.4 Hz) |
| 237 | 3 | Et | | | FAB: 408<br>NMR: 1.04 (3 H, t, J = 7.5 Hz), 1.22 (3 H, t, J = 7.5Hz), 1.75-1.83 (1 H, m), 2.11-2.20 (1 H, m), 2.26 (3 H, s), 2.37-2.45 (2 H, m), 2.57-2.63 (1 H, m), 2.67-2.77 (5 H, m), 4.38-4.47 (1 H, m), 5.42 (2 H, s), 6.93-6.96 (2 H, m), 7.08-7.13 (2 H, m), 7.31 (1 H, d, J = 8.6 Hz), 7.58-7.60 (1 H, m), 8.10 (1 H, s), 8.25-8.27 (1 H, m) |
| 238 | 3 | Me | (S)-3-methyl-N-methylpyrrolidinyl | | FAB: 394<br>NMR: 1.16-120 (3 H, m), 1.75-1.83 (1 H, m), 2.11-2.20 (1 H, m), 2.26 (3 H, s), 2.28 (3 H, s), 2.38-2.46 (2 H, m), 2.57-2.63 (1 H, m), 2.68-2.76 (3 H, m), 4.38-4.47 (1 H, m), 5.40 (2 H, s), 6.97-7.01 (2 H, m), 7.09-7.14 (2 H, m), 7.38 (1 H, d, J = 8.6 Hz), 7.59-7.61 (1 H, m), 8.09 (1 H, d, J = 1.2 Hz), 8.26 (1 H, d, J = 7.1 Hz) |

TABLE 37

| Ex | Syn | R¹² | Sal | Dat |
|---|---|---|---|---|
| 239 | 9 | [Structure: 3-acetyl-2-methyl-1-(4-fluorobenzyl)indole-5-carboxamide with N-(N-methylpyrrolidin-3-yl)] | (CO₂H)₂ | ESI: 408 |
| 240 | 3 | [Structure: 3-ethyl-2-methyl-1-(4-fluorobenzyl)indole-5-carboxamide with N-(N-methylpyrrolidin-3-yl)] | | FAB: 394<br>NMR: 1.18 (3 H, t, J = 7.5 Hz), 1.75-1.83 (1 H, m), 2.12-2.21 (1 H, m), 2.26 (3 H, s), 2.28 (3 H, s), 2.38-2.46 (2 H, m), 2.58-2.64 (1 H, m), 2.69-2.76 (3 H, m), 4.39-4.47 (1 H, m), 5.40 (2 H, s), 6.97-7.01 (2 H, m), 7.08-7.14 (2 H, m), 7.38 (1 H, d, J = 8.7 Hz), 7.59-7.61 (1 H, m), 8.09 (1 H, s), 8.27 (1 H, d, J = 7.1 Hz) |

TABLE 38

| Ex | Syn | R² | R¹ | Sal | Dat |
|---|---|---|---|---|---|
| 241 | 1 | Bn | methylguanidine (N-methyl, NH₂, NH₂) | HCl | FAB: 309 |
| 242 | 1 | 4-F-C₆H₄-CH₂CH₂- | methylguanidine (N-methyl, NH₂, NH₂) | HCl | ESI: 327 |
| 243 | 9 | Bn | —NH—(CH₂)₂—NMe₂ | HCl | FAB: 338 |

TABLE 39

| Ex | Syn | R⁷ | Sal | Dat |
|---|---|---|---|---|
| 244 | 1 | Me | 2HCl | FAB: 326<br>NMR: 2.86 (3 H, s), 5.73 (2 H, s), 7.19-7.25 (2 H, m), 7.40-7.43 (2 H, m), 7.95 (1 H, d, J = 8.7 Hz), 825-8.27 (1 H, m), 8.67 (1 H, d, J = 1.3 Hz), 8.72 (2 H, s), 8.89 (2 H, s) |
| 245 | 1 | H | 2HCl | FAB: 312 |
| 246 | 1 | MeO— | | FAB: 342 |
| 247 | 1 | F₃C— | | ESI: 380 |

TABLE 40

| Ex | Syn | R⁷ | Sal | Dat |
|---|---|---|---|---|
| 248 | 1 | Me | 2HCl | FAB: 326 |
| 249 | 1 | H | 2HCl | FAB: 312 |
| 250 | 1 | MeO— | | FAB: 342 |

TABLE 41

| Ex | Syn | Structure | Sal | Dat |
|---|---|---|---|---|
| 251 | 1 | 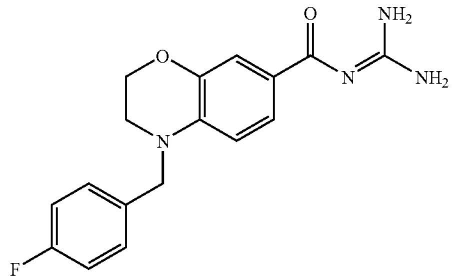 | 2HCl | ESI: 329 |
| 10 | 10 | 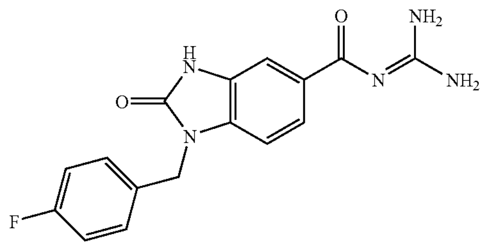 | HCl | FAB: 328 |
| 252 | 10 | 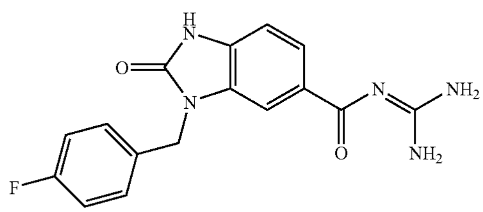 | HCl | FAB: 328 |

INDUSTRIAL APPLICABILITY

Since the compound of the present invention has excellent antagonistic activity for both of the 5-HT$_{2B}$ and 5-HT$_7$ receptors, it is useful as a pharmaceutical, particularly as an agent for treating IBS.

The invention claimed is:

1. A compound represented by the following formula (I-b) or a pharmaceutically acceptable salt thereof

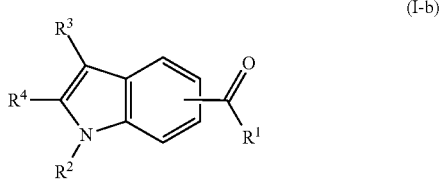

(I-b)

wherein [symbols in the formula have the following meanings;

$R^1$: —N=C(NH$_2$)$_2$, —N(R$^0$)-(nitrogen-containing saturated heterocyclic group which may be substituted), —N(R$^0$)-lower alkylene-N(lower alkyl)$_2$, —N(R$^0$)-lower alkylene-(nitrogen-containing saturated heterocyclic group which may be substituted), —N(R$^0$)-lower alkylene-(heterocyclic group substituted with —N(lower alkyl)$_2$) or —N(R$^0$)-lower alkylene-(cycloalkyl substituted with —N(lower alkyl)$_2$), $R^0$: each independently —H or lower alkyl, wherein (I) when $R^1$ is —N=C(NH$_2$)$_2$, then

[$R^2$: —H, lower alkyl, halogeno-lower alkyl, cycloalkyl, aryl, heterocyclic group, —CH(aryl)$_2$ or lower alkylene-R$^{21}$, wherein the aryl and heterocyclic group in $R^2$ may be respectively substituted, $R^{21}$: —OR$^0$, —O-aryl, —N(R$^0$)$_2$, —CH(OH)R$^0$, —C(O)R$^0$, —C(O)-aryl, —CO$_2$R$^0$, —C(O)N(R$^0$)$_2$, cycloalkyl, aryl, heterocyclic group or CH(aryl)$_2$, wherein the aryl and heterocyclic group in $R^{21}$ may be respectively substituted, $R^3$ and $R^4$: —H, lower alkyl, halogeno-lower alkyl, lower alkylene-OR$^0$, lower alkylene-N(R$^0$)$_2$, —O-lower alkyl, —S-lower alkyl, —S(O)-lower alkyl, —S(O)$_2$-lower alkyl, —C(O)R$^0$, —CO$_2$R$^0$ or —C(O)N(R$^0$)$_2$, and the substituting position of —C(O)R$^1$ may be any position on the benzene ring, with the proviso that, $R^2$ is —H, methyl, isopropyl or unsubstituted benzyl, at least one of $R^3$ and $R^4$ is not —H], and (II) when $R^1$ is —N(R$^0$)-(nitrogen-containing saturated heterocyclic group which may be substituted), —N(R$^0$)-lower alkylene-N(lower alkyl)$_2$,) —N(R$^0$)-lower alkylene-(nitrogen-containing saturated heterocyclic group which may be substituted), —N(R$^0$)-lower alkylene-(heterocyclic group substituted with -N(lower alkyl)$_2$) or —N(R$^0$)-lower alkylene-(cycloalkyl substituted with —N(lower alkyl)$_2$), then

[$R^2$: lower alkylene-aryl or lower alkylene-heterocyclic group, wherein the aryl and heterocyclic group in $R^2$ may be respectively substituted, $R^3$ and $R^4$: lower alkyl, lower alkylene-OR$^0$, —C(O)R$^0$, —S-lower alkyl, —S(O)-lower alkyl or —S(O)$_2$-lower alkyl, and the substituting position of —C(O)R$^1$ is at the para-position of N(R$^2$)], with the proviso that 1-benzyl-N-[2-(dimethylamino)ethyl]-2,3-dimethyl-1H-indole-5-carboxamide is excluded].

2. The compound described in claim 1, wherein the substituting position of —C(O)R$^1$ is at the para-position of N(R$^2$); R$^2$ is lower alkylene-(aryl which may be substituted) or lower alkylene-(heterocyclic group which may be substituted); R$^3$ is lower alkyl or —C(O)R$^0$; and R$^4$ is lower alkyl.

3. The compound described in claim 2, wherein R$^2$ is lower alkylene-(phenyl which may be substituted with halogen).

4. The compound described in claim 3, wherein R$^1$ is —N═C(NH$_2$)$_2$, —N(R$^0$)-(nitrogen-containing saturated heterocyclic group which may be substituted with lower alkyl), —N(R$^0$)-lower alkylene-N(lower alkyl)$_2$ or —N(R$^0$)-lower alkylene-(nitrogen-containing saturated heterocyclic group which may be substituted with lower alkyl).

5. The compound described in claim 4, wherein R$^1$ is —N═C(NH$_2$)$_2$ or —NH-(nitrogen-containing saturated heterocyclic group which may be substituted with lower alkyl).

6. A compound described in claim 1, which is selected from the group consisting of:
- 3-ethyl-1-(4-fluorobenzyl)-2-methyl-N-[(3S)-1-methylpyrrolidin-3-yl]-1H-indole-5-carboxamide,
- N-(diaminomethylene)-3-ethyl-1-(4-fluorobenzyl)-2-methyl-1H-indole-5-carboxamide, and
- 3-acetyl-N-(diaminomethylene)-1-(4-fluorobenzyl)-2-methyl-1H-indole-5-carboxamide, or a pharmaceutically acceptable salt thereof.

7. A pharmaceutical composition comprising the compound desribed in claim 1 or a salt thereof, and a pharmaceutically acceptable carrier.

8. A method for treating irritable bowel syndrome, which comprises administering to a patient a therapeutically effective amount of the compound described in claim 1 or a salt thereof.

* * * * *

UNITED STATES PATENT AND TRADEMARK OFFICE
CERTIFICATE OF CORRECTION

PATENT NO. : 7,985,764 B2
APPLICATION NO. : 12/279221
DATED : July 26, 2011
INVENTOR(S) : Hidetaka Kaku et al.

It is certified that error appears in the above-identified patent and that said Letters Patent is hereby corrected as shown below:

TITLE PAGE, ITEM (56) FOREIGN PRIORITY DOCUMENTS
"JP 2005162657 A * 6/2005" should read be deleted (duplicate).

COLUMN 6:
Line 49, "has" should read --have--.

COLUMN 12:
Line 58, "atoms." should read --atoms. For example,--; and
Line 59, "¶For Example," should be deleted.

COLUMN 13:
Line 46, "—S(O)" should read -- —S(O)$_2$--;
Line 47, "$_2$-lower" should read --lower--; and
Line 55, "ring," should read --ring;--.

COLUMN 15:
Line 37, "thyl-1H-indole-5-carboxamide and" should read
-- thyl-1H-indole-5-carboxamide; and --.

COLUMN 27:
Line 65, "producing" should read --produced--.

COLUMN 28:
Line 33, "to>2" should read --to 2--.

COLUMN 30:
Line 40, "concentrations." should read --concentrations. Binding--; and
Line 41, "¶Binding" should be deleted.

COLUMN 33:
Line 61, "cynomethylene" should read --cyanomethylene--.

Signed and Sealed this
Twenty-ninth Day of November, 2011

David J. Kappos
*Director of the United States Patent and Trademark Office*

COLUMN 36:

Line 5, "temperature." should read --temperature. Water--; and

Line 6, "¶Water" should be deleted.

COLUMN 37:

Line 22, "solid" should read --solid.--;

Line 46, "hours." should read --hours. After--; and

Line 47, "¶After" should be deleted.

COLUMN 38:

Line 59, "precipitate" should read --precipitated--.

COLUMN 40:

Line 38, "0.60 ml" should read --0.60 ml of--;

Line 57, "A 8.9" should read --An 8.9--; and

Line 66, "was" should read --were--.

COLUMN 64:

Line 66, "181" should read --191--.

COLUMN 74:

Line 41, "-C(0)N(R$^0$)$_2$," should read -- —C(O)N(R$^0$)$_2$,--.